United States Patent
Anderson et al.

(12)

(10) Patent No.: US 6,686,184 B1
(45) Date of Patent: Feb. 3, 2004

(54) PATTERNING OF SURFACES UTILIZING MICROFLUIDIC STAMPS INCLUDING THREE-DIMENSIONALLY ARRAYED CHANNEL NETWORKS

(75) Inventors: Janelle R. Anderson, Cambridge, MA (US); Daniel T. Chiu, Seattle, WA (US); Noo-Li Jeon, Cambridge, MA (US); Sui Huang, Boston, MA (US); Ravi Kane, Cambridge, MA (US); Insung S. Choi, Cambridge, MA (US); Donald E. Ingber, Boston, MA (US); George M. Whitesides, Newton, MA (US)

(73) Assignees: President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/578,562

(22) Filed: May 25, 2000

(51) Int. Cl.$^7$ .......................... C12N 11/00; C12N 11/02; C12M 1/00; C07K 17/00; C07K 17/02

(52) U.S. Cl. ....................... 435/174; 435/176; 435/177; 435/180; 435/283.1; 536/810; 536/811; 536/812; 536/815

(58) Field of Search .................................. 435/174, 176, 435/177, 180, 283.1; 264/259; 530/810, 811, 812, 815

(56) References Cited

U.S. PATENT DOCUMENTS

| | | | |
|---|---|---|---|
| 5,512,131 A | 4/1996 | Kumar et al. ............. | 156/655.1 |
| 5,776,748 A | 7/1998 | Singhvi et al. | |
| 5,928,880 A | 7/1999 | Wilding et al. | |
| 5,955,029 A | 9/1999 | Wilding et al. | |
| 5,976,826 A | 11/1999 | Singhvi et al. | |
| 6,103,479 A | 8/2000 | Taylor ......................... | 435/7.2 |
| 6,167,910 B1 | 1/2001 | Chow | |
| 6,184,029 B1 | 2/2001 | Wilding et al. | |
| 6,321,791 B1 | 11/2001 | Chow | |
| 6,334,301 B1 | 1/2002 | Otsap et al. | |
| 6,355,198 B1 | 3/2002 | Kim et al. .................. | 264/259 |
| 6,368,838 B1 | 4/2002 | Singhvi et al. | |

FOREIGN PATENT DOCUMENTS

| | | |
|---|---|---|
| WO | WO 97/33737 | 9/1997 |
| WO | WO 99/54786 | 10/1999 |
| WO | WO 01/03208 A1 | 1/2001 |
| WO | WO 01/89787 A2 | 11/2001 |
| WO | WO 01/89788 A2 | 11/2001 |

OTHER PUBLICATIONS

Kenis, et. al, Science, vol. 285, Jul. 2, 1999, pp 83–85.*
Takayama, et. al., Proc. Natl. Acad. Sci USA, vol. 96, May 1999, pp. 5545–5548.*
Bergveld, "The Challenge of Developing μTAS," Micro Total Analysis Systems, Proceedings of the μTAS '94 Workshop, Nov. 21–22, 1994, Kluwer Academic Publishers, pp. 1–4, 1995.
Fluitman et al., "Micromechanical Components for μTAS," Micro Total Analysis Systems, Proceedings of the μTAS '94 Workshop, Nov. 21–22, 1994, Kluwer Academic Publishers, pp. 73–83, 1995.
Mensinger et al., "Microreactor with Integrated Static Mixer and Analysis System," Micro Total Analysis Systems, Proceedings of the μTAS '94 Workshop, Nov. 21–22, 1994, Kluwer Academic Publishers, pp. 237–243, 1995.
Schomburg et al., "Components for Microfluidic Handling Modules," Micro Total Analysis Systems, Proceedings of the μTAS '94 Workshop, Nov. 21–22, 1994, Kluwer Academic Publishers, pp. 1–4, 1995.
Duffy et al., "Rapid Prototyping of Microfluidic Systems in Poly(dimethylsiloxane)," Analytical Chemistry, vol. 70, No. 23, pp. 4974–4985, 1998.
Chiu et al., "Patterned deposition of cells and proteins onto surfaces by using three–dimensional microfluidic systems," Proc. Natl. Acad. Sci., published on the Internet Feb. 2000; published in print vol. 97, No. 6, pp. 2408–2413, Mar. 2000.
Jo et al., "Three–Dimensional Micro–Channel Fabrication in Polydimethylsiloxane (PDMS) Elastomer," Journal of Microelectromechanical Systems, vol. 9, No. 1, pp. 76–81, Mar. 2000.
Jo & Beebe, "Fabrication of Three–Dimensional Microfluidic Systems by Stacking Molded Polydimethylsiloxane (PDMS) Layers," SPIE Conference on Microfluidic Devices and Systems II, SPIE, vol. 3877, pp. 222–229, Sep. 1999.
Lammerink et al., "Modular Concept for Fluid Handling Systems, A demonstrator Micro Analysis System," IEEE, pp. 389–394, 1996.
Blankenstein & Larsen, "Modular concept of a laboratory on a chip for chemical and biochemical analysis," Biosensors & Bioelectronics, vol. 13, No. 3–4, pp. 427–438, 1998.

(List continued on next page.)

*Primary Examiner*—David M. Naff
(74) *Attorney, Agent, or Firm*—Wolf, Greenfield & Sacks, P.C.

(57) ABSTRACT

Microfluidic systems and methods are provided for fabricating complex patterns of materials, such as proteins, inorganic materials or cells, on surfaces. Complex, discontinuous patterns on surfaces can be formed incorporating or depositing multiple materials. A stamp structure has a flow path containing a series of interconnected channels. The channels include a first channel within an interior of the stamp structure, a second channel within a stamping surface of the structure defining a pattern, and a channel fluidically interconnecting the first and second channels. After contacting the stamp with a surface, a fluid is introduced into the flow path so that the fluid contacts the surface to form a pattern. In another embodiment, the stamp structure has two non-fluidically interconnected first and second flow paths defining first and second patterns of channels to produce non-continuous first and second patterns on a surface.

25 Claims, 25 Drawing Sheets-

OTHER PUBLICATIONS

Jackman et al., "Design and Fabrication of Topologically Complex, Three–Dimensional Microstructures," Science, vol. 280, pp. 2089–2091, Jun. 1998.

González et al., "MicroJoinery: concept, definition, and application to microsystem development," Sensors and Actuators A, vol. 66, pp. 315–332, 1998.

Verpoorte et al., "Three–dimensional micro flow manifolds for miniaturized chemical analysis systems," J. Micromech. Microeng., vol. 4, pp. 246–256, 1994.

Fettinger et al., "Stacked modules for micro flow systems in chemical analysis: concept and studies using an enlarged model," Sensors and Actuators B, vol. 17, pp. 19–25, 1993.

Ikuta et al., "Three Dimensional Micro Integrated Fluid Systems (MIFS) Fabricated by Stereo Lithography," IEEE, pp. 1–6, 1994.

Bloomstein & Ehrlich, "Laser–Chemical Three–Dimensional Writing of Multimaterial Structures for Microelectromechanics," IEEE, pp. 202–203, 1991.

Kunz et al., "Applications of lasers in microelectronics and micromechanics," Applied Surface Science, vol. 79/80, pp. 12–24, 1994.

Nassuphis et al., "Three–dimensional laser direct writing: Applications to multichip modules," J. Vac. Sci. Technol. B, vol. 12, No. 6, pp. 3294–3299, Nov./Dec. 1994.

Bloomstein & Ehrlich, "Laser–Chemical 3–D Micromachining," Mat. Res. Soc. Symp. Proc., vol. 282, pp. 165–171, 1993.

Bloomstein & Ehrlich, "Laser–chemical three–dimensional writing for microelectromechanics and application to standard–cell microfluidics," J. Vac. Sci. Tehcnolo. B, vol. 10, No. 6, pp. 2671–2674, Nov./Dec. 1992.

Larsson et al., "Silicon Based Replication Technology of 3D–Microstructures by Conventional CD–Injection Molding Techniques," 1997 International Conference on Solid–State Sensors and Actuators, Jun. 16–19, 1997, IEEE, pp. 1415–1418, 1997.

Poplawski et al., "A Simple Package Process for Chemical Sensors," Solid–State Sensor and Actuator Workshop, Jun. 13–16, 1994, TRF, pp. 25–28, 1994.

Guérin et al., "Simple and Low Cost Fabrication of Embedded Micro–Channels by Using a New Thick–Film Photoplastic," 1997 International Conference on Solid–State Sensors and Actuators, Jun. 18–19, 1997, IEEE, pp. 1419–1422, 1997.

Kumar & Whitesides, "Features of gold having micrometer to centimeter dimensions can be formed through a combination of stamping with an elastomeric stamp and an alkanethiol "ink" followed by chemical etching," Appl. Phys. Lett., vol. 63, No. 14, pp. 2002–2004, Oct. 1993.

Internet web site: "SU–8: A Thick Photo–Resist for MEMS", http://aveclafaux.freeservers.com/SU–8 html, printed Mar. 31, 2000.

Internet web site: "SU–8 Technologies at EPFL: Introduction", http://dmtwww.epfl.ch/ims/micsys/projects/su8/, printed Mar. 31, 2000.

Internet web site: "Applications in Microfluidics," http://dmtwww.epfl.ch/ims/micsys/projects/su8/eponp3.html, printed Mar. 31, 2000.

Inernet web site: http://dmtwww.epfl.ch/ims/micsys/projects/su8/eponp5.html, printed on Mar. 31, 2000.

C. Gonzalez et al., "MicroJoinery: concept, definition, and application to microsystem development," Sensors and Actuators A, vol. 66, pp. 315–332, 1998.

* cited by examiner

PATTERNING OF SURFACES UTILIZING MICROFLUIDIC STAMPS INCLUDING THREE-DIMENSIONALLY ARRAYED CHANNEL NETWORKS

GOVERNMENT FUNDING

This invention was made with government support: Grant Nos. GM51559; GM30367 from the National Institutes of Health, and Grant No. ECS9729405 from the National Science Foundation. The government has certain rights to the invention.

FIELD OF INVENTION

The present invention involves microfluidic network structures comprising microfluidic stamps and methods for using such stamps for forming patterns on surfaces.

BACKGROUND OF THE INVENTION

The need for complexity in microfluidic systems is increasing rapidly as sophisticated functions—chemical reactions and analyses, bioassays, high-throughput screens, and sensors—are being integrated into single microfluidic devices. Complex systems of channels require more complex connectivity than can be generated in conventional two-dimensional microfluidic systems having a single level of channels, since such typical single-level designs do not allow two channels to cross without fluidically connecting. Most methods for fabricating microfluidic channels are based on photolithographic procedures, and yield such two-dimensional systems. There are a number of more specialized procedures, such as stereolithography (see for example, K. Ikuta, K. Hirowatari, T. Ogata, *Proc. IEEE MEMS '94*, Oiso, Japan, Jan. 25–28, 1994, pp. 1–6), laser-chemical three-dimensional writing (see for example, T. M. Bloomstein, D. J. Ehrlich, *J. Vac. Sci. Technol.* B, Vol. 10, pp. 2671–2674, 1992), and modular assembly (see for example, C. Gonzalez, R. L. Smith, D. G. Howitt, S. D. Collins, *Sens. Actuators A*, Vol. 66, pp. 315–332, 1998), that yield three-dimensional structures, but these methods are typically time consuming, difficult to perform, and expensive, and are thus not well suited for either prototyping or manufacturing, and are also not capable of making certain types of structures. Better methods for generating complex three-dimensional microfluidic systems are needed to accelerate the development of microfluidic technology. The present invention, in some embodiments, provides such improved methods for generating complex three-dimensional microfluidic systems.

It is known to use a stamp or mold to transfer patterns to a surface of a substrate (see for example, R. S. Kane, S. Takayama, E. Ostuni, D. E. Ingber, G. M. Whitesides, *Biomaterials*, Vol. 20, pp. 2363–2376, 1999; and Y. Xia, G. M. Whitesides, *Angew. Chem. Int. Ed. Engl.*, Vol. 37, pp. 551–575, 1998; U.S. Pat. No. 5,512,131; International Pat. Publication No. WO 97/33737, published Sep. 18, 1997). Most conventional soft lithographic techniques, for example, microcontact printing ($\mu$CP) (see for example, C. S. Chen, M. Mrksich, S. Huang, G. M. Whitesides, D. E. Ingber, *Science*, Vol. 276, pp. 1425–1428, 1997; A. Bernard, E. Delamarche, H. Schmid, B. Michel, H. R. Bosshard, H. Biebuyck, *Langmuir*, Vol. 14, pp. 2225–2229, 1998) and micromolding in capillaries (MIMIC) (see for example, N. L. Jeon, I. S. Choi, B. Xu, G. M. Whitesides, *Adv. Mat.*, Vol. 11, pp. 946–949, 1999; E. Delamarche, A. Bernard, H. Schmid, B Michel, H. Biebuyck, *Science*, Vol. 276, pp. 779–781, 1997; E. Delamarche, A. Bernard, H. Schmid, A. Bietsch, B. Michel, h. Biebuyck, *J. Am. Chem. Soc.*, Vol. 120, pp. 500–508, 1998; A. Folch, A. Ayon, O. Hurtado, M. A. Schmidt, M. Toner, *J. Biomech. Eng.*, Vol. 121, pp. 28–34, 1999; A. Folch, M. Toner, *Biotech. Prog.*, Vol. 14, pp. 388–392, 1998), have been limited to procedures that pattern one substance at a time, or to relatively simple, continuous patterns. These constraints are both topological and practical. The surface of a stamp in $\mu$CP, or of a channel system in MIMIC, is effectively a two-dimensional structure. In $\mu$CP, this two-dimensionality of the stamp limits the types of patterns that can be transferred to those comprising a single "color" of ink in the absence of a way of selectively "inking" different regions of the stamp with different materials. Patterning of multiple "inks" using conventional methods requires multiple steps of registration and stamping. In MIMIC, the two-dimensional channel system limits patterning to relatively simple, continuous structures or requires multiple patterning steps.

There remains a general need in the art for improved methods for forming patterns on surfaces with soft lithographic techniques, and for providing techniques able to pattern onto a surface arbitrary two-dimensional patterns and able to form complex patterns comprised of multiple regions, where different regions of the pattern can comprise different materials, on a surface without the need for multiple steps of registration or stamping and without the need to selectively "ink" different regions of the stamp with different materials. The present invention, in some embodiments, provides such improved methods for forming patterns on surfaces with soft lithographic techniques.

SUMMARY OF THE INVENTION

The present invention involves, in certain embodiments, improved microfluidic systems and procedures for fabricating improved microfluidic systems, which contain one or more levels of microfluidic channels. The inventive methods can provide a convenient route to topologically complex and improved microfluidic systems. The present invention also, in some embodiments, involves microfluidic systems and methods for fabricating complex patterns of materials, such as biological materials and cells, on surfaces. In such embodiments, the invention involves microfluidic surface patterning systems and methods for fabricating complex, discontinuous patterns on surfaces that can incorporate or deposit multiple materials onto a surface. The present invention, in some embodiments, can provide improved stamps for microcontact surface patterning able to pattern onto a surface arbitrary two-dimensional patterns and able to pattern multiple substances onto a surface without the need for multiple steps of registration or stamping during patterning and without the need to selectively "ink" different regions of the stamp with different materials.

According to one embodiment of the invention, a microfluidic network is disclosed. The microfluidic network comprises a polymeric structure including therein at least a first and a second non-fluidically interconnected fluid flow paths. At least the first flow path comprises a series of interconnected channels within the polymeric structure. The series of interconnected channels includes at least one first channel disposed within a first level of the structure, at least one second channel disposed within a second level of the structure, and at least one connecting channel fluidically interconnecting the first channel and the second channel. At least one channel within the structure has a cross-sectional dimension not exceeding about 500 $\mu$m. The structure includes at least one channel disposed within the first level of the structure that is non-parallel to at least one channel disposed within the second level of the structure.

In another embodiment of the invention, a microfluidic network is disclosed. The microfluidic network comprises an elastomeric structure including therein at least one fluid flow path. The flow path comprises a series of interconnected channels within the structure. The series of interconnected channels includes at least one first channel disposed within a first level of the structure, at least one second channel disposed within a second level of the structure, and at least one connecting channel fluidically interconnecting the first channel and the second channel. At least one channel within the structure has a cross-sectional dimension not exceeding about 500 μm, and the structure includes at least one channel disposed within the first level of the structure that is non-parallel to at least one channel disposed within the second level of the structure.

In yet another embodiment, a polymeric membrane is disclosed. The polymeric membrane comprises a first surface including at least one channel disposed therein, a second surface including at least one channel disposed therein, and a polymeric region intermediate the first surface and the second surface. The intermediate region includes at least one connecting channel therethrough fluidically interconnecting the channel disposed in the first surface and the channel disposed in the second surface of the membrane. At least one channel has a cross-sectional dimension not exceeding about 500 μm.

In another embodiment of the invention, a method for forming a microfluidic network structure is disclosed. The method comprises providing at least one mold substrate, forming at least one topological feature on a surface of the mold substrate to form a first mold master, contacting the surface with a first hardenable liquid, hardening the liquid thereby creating a first molded replica of the surface, removing the first molded replica from the first mold master, and assembling the first molded replica into a structure comprising a microfluidic network. The assembled microfluidic network structure has at least one fluid flow path comprising a series of interconnected channels within the structure. The series of interconnected channels includes at least one first channel disposed within a first level of the structure, at least one second channel disposed within a second level of the structure, and at least one connecting channel fluidically interconnecting the first channel and the second channel. At least one of the channels within the structure has a cross-sectional dimension not exceeding about 500 μm. The structure includes at least one channel disposed within the first level of the structure that is non-parallel to at least one channel disposed within the second level of the structure.

In yet another embodiment, a method for forming a molded structure is disclosed. The method comprises providing at least one mold substrate and forming at least one two-level topological feature having at least one lateral dimension not exceeding 500 μm on a surface of the substrate to form a mold master. The two-level topological feature is characterized by a first portion having a first depth or height with respect to a region of the surface adjacent to the feature, and a second portion integrally connected with the first portion having a second depth or height with respect to the region of the surface adjacent to the feature that is greater than the first depth or height. The method further comprises contacting the surface with a hardenable liquid, hardening the liquid thereby creating a molded replica of the surface, and removing the molded replica from the mold master.

In another embodiment of the invention, a method for forming topological features on a surface of a material is disclosed. The method comprises exposing portions of a surface of a first layer of photoresist to radiation in a first pattern, coating the surface of the first layer of photoresist with a second layer of photoresist, exposing portions of a surface of the second layer of photoresist to radiation in a second pattern different from the first pattern, and developing the first and second photoresist layers with a developing agent. The developing step yields a positive relief pattern in photoresist that includes at least one two-level topological feature having at least one cross-sectional dimension not exceeding 500 μm. The two-level topological feature is characterized by a first portion having a first height with respect to the surface of the material and a second portion, integrally connected to the first portion, having a second height with respect to the surface of the material.

In yet another embodiment, a method for forming a molded structure is disclosed. The method involves providing a first mold master having a surface formed of an elastomeric material and including at least one topological feature with at least one cross-sectional dimension not exceeding about 500 μm thereon. The method further comprises providing a second mold master having a surface including at least one topological feature with at least one cross-sectional dimension not exceeding about 500 μm thereon. The method further comprises placing a hardenable liquid in contact with the surface of at least one of the first and second mold master, bringing the surface of the first mold master into at least partial contact with the surface of the second mold master, hardening the liquid thereby creating a molded replica of the surface of the first mold master and the surface of the second mold master, and removing the molded replica from at least one of the mold masters.

In another embodiment of the invention, a method for forming a molded structure is disclosed. The method involves providing a first mold master having a surface including at least a first topological feature with at least one cross-sectional dimension not exceeding about 500 μm thereon and at least a second topological feature comprising a first alignment element. The method further comprises providing a second mold master having a surface including at least a first topological feature with at least one cross-sectional dimension not exceeding about 500 μm thereon and at least a second topological feature comprising a second alignment element having a shape that is mateable to the shape of the first alignment element. The method further comprises placing a hardenable liquid in contact with the surface of at least one of the first and second mold master, bringing the surface of the first mold master into at least partial contact with the surface of the second mold master, aligning the first topological features of the first and second mold masters with respect to each other by adjusting a position of the first mold master with respect to a position of the second mold master until the first alignment element matingly engages and interdigitates with the second alignment element, hardening the liquid thereby creating a molded replica of the surface of the first mold master and the surface of the second mold master, and removing the molded replica from at least one of the mold masters.

In yet another embodiment of the invention, a method for aligning and sealing together surfaces is disclosed. The method comprises disposing two surfaces, at least one of which is oxidized, adjacent to each other such that they are separated from each other by a continuous layer of a liquid that is essentially non-reactive with the surfaces, aligning the surfaces with respect to each other, and removing the liquid from between the surfaces, thereby sealing the surfaces together via a chemical reaction between the surfaces.

In another embodiment of the invention, a method for molding an article is disclosed. The method comprises providing a first mold master having a surface with a first set of surface properties and providing a second mold master having a surface with a second set of surface properties. At least one of the first and second mold masters has a surface including at least one topological feature with at least one cross-sectional dimension not exceeding about 500 μm thereon. The method further comprises placing a hardenable liquid in contact with the surface of at least one of the first and second mold masters, bringing the surface of the first mold master into at least partial contact with the surface of the second mold master, hardening the liquid thereby creating a molded replica of the surface of the first mold master and the surface of the second mold master, separating the mold masters from each other, and removing the molded replica from the surface of the first mold master while leaving the molded replica in contact with and supported by the surface of the second mold master.

In yet another embodiment, a microfluidic network is disclosed. The microfluidic network comprises a polymeric structure including therein at least a first and a second non-fluidically interconnected fluid flow paths. The first flow path comprises at least two non-colinear interconnected channels disposed within a first plane, and the second flow path comprises at least one channel disposed within a second plane that is non-parallel with the first plane. At least one channel within the structure has a cross-sectional dimension not exceeding about 500 μm.

In another embodiment of the invention, a microfluidic network is disclosed. The microfluidic network comprises a polymeric structure including therein at least one fluid flow path. The fluid flow path is formed of at least one channel and has a longitudinal axis defined by the direction of bulk fluid flow within the flow path. The longitudinal axis of the flow path is not disposed within any single plane.

In another embodiment of the invention, a method of patterning a material surface is disclosed. The method comprises providing a stamp having a structure including at least one flow path comprising a series of interconnected channels within the structure. The series of interconnected channels includes at least one first channel disposed within an interior region of the structure, at least one second channel disposed within a stamping surface of the structure defining a first pattern therein, and at least one connecting channel fluidically interconnecting the first channel and the second channel. The method further comprises contacting the stamping surface with a portion of the material surface, and, while maintaining the stamping surface in contact with the portion of the material surface, at least partially filling the flow path with a fluid so that at least a portion of the fluid contacts the material surface.

In yet another embodiment, a method of patterning a material surface is disclosed. The method comprises providing a stamp having a structure including at least two non-fluidically interconnected flow paths therein including a first fluid flow path defining a first pattern of channels disposed within a stamping surface of the structure and a second fluid flow path defining a second pattern of channels disposed within the stamping surface of the structure. Each of the first and second patterns of channels is non-continuous, and the channels defining the first pattern are non-intersecting with the channels defining the second pattern. The method further comprises contacting the stamping surface with a portion of the material surface, while maintaining the stamping surface in contact with the portion of the material surface, at least partially filling the first flow path with a first fluid so that at least a portion of the first fluid contacts the material surface and at least partially filling the second flow path with a second fluid so that at least a portion of the second fluid contacts the material surface, and removing the stamping surface to provide a pattern on the material surface according to the first pattern, which is formed by contact of the material surface with the first fluid, and according to the second pattern, which is formed by contact of the material surface with the second fluid.

In another embodiment, a method of patterning a material surface is disclosed the method involves providing a stamp having a structure including at least one non-linear fluid flow path therein in fluid communication with a stamping surface of the structure. The method further involves contacting the stamping surface with a portion of the material surface and, while maintaining the stamping surface in contact with the portion of the material surface, at least partially filling the flow path with a fluid so that at least a portion of the fluid contacts the material surface.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

FIG. 1b is a two-dimensional projection of the microfluidic network structure of FIG. 1a;

FIG. 2b is a two-dimensional projection of the microfluidic network structure of FIG. 2a;

FIG. 3b is a two-dimensional projection of the microfluidic network structure of FIG. 3a;

FIG. 4b is a two-dimensional projection of the microfluidic network structure of FIG. 4a;

FIG. 14b is a schematic illustration of the fluid flow path layout of the microfluidic stamp illustrated in FIG. 14a;

FIG. 14c is a photocopy of a photomicrograph of a patterned surface produced using the microfluidic stamp illustrated in FIG. 14a;

FIG. 15b is a photocopy of photomicrograph of a stamped pattern on a material surface produced using a microfluidic stamp having the microfluidic network structure illustrated in FIG. 15a;

FIGS. 16b–16d are photocopies of photomicrographs of patterned cells on a material surface deposited using a microfluidic stamp having the microfluidic network configuration illustrated in FIG. 16a;

FIGS. 17b–17e are photocopies of photomicrographs of patterned cells on a material surface deposited using a microfluidic stamp having the microfluidic network configuration illustrated in FIG. 17a.

DETAILED DESCRIPTION

Figure 1A:
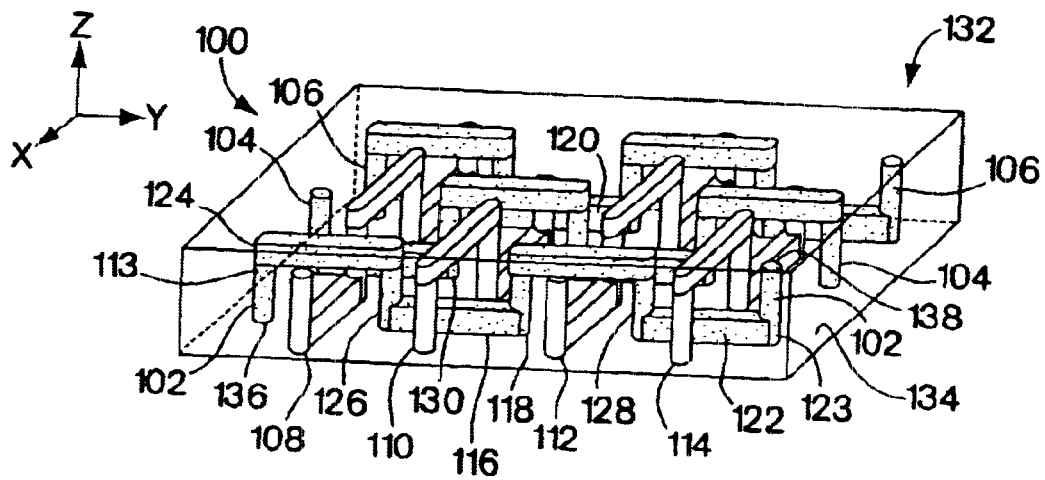
FIG. 1a is a perspective view of a schematic illustration of a microfluidic network structure having a series of interconnected channels arranged in a "basketweave" configuration.

The present invention is directed to fabrication methods for producing three-dimensional microfluidic network structures, polymeric microfluidic network structures having a three-dimensional array of channels included therein, and various uses for the microfluidic networks, for example as a template for forming and depositing complex patterns on substrates. A "three-dimensional microfluidic network," "three-dimensional microfluidic network structure," or "three-dimensional microfluidic stamp" as used herein refers to a structure capable of containing a fluid and/or providing fluid flow therethrough, which includes at least three channels therein, and may contain many more; furthermore, the structure includes at least three channels that are arranged with respect to each other such that there exists no plane, or curved planar surface, which contains disposed therein the longitudinal axes of the three channels. The microfluidic networks provided according to the invention, because of their three-dimensionality of structure, are able, for example, to provide channels within the structure having longitudinal axes (defined as the axial centerline of the channel aligned parallel to the direction of bulk fluid flow within the channel) aligned along each of the x, y, and z directional components of space. The ability to produce microfluidic structures having channels arranged in a three-dimensional network enables the systems provided according to the invention to include therein a plurality of channels providing one or more independent fluid flow paths, where the channels and flow paths can be arrayed in arbitrarily complex geometric networks since the channels of the structures have the capability of crossing over and/or under each other within the structure.

One way to analogize the capabilities of the microfluidic networks, and methods for producing the microfluidic networks, according to the invention, is to compare the channel systems of the microfluidic networks to a knot in three-dimensional space. The microfluidic networks provided according to the invention have the ability to fabricate the physical realization of knots, and thus can include channel systems of arbitrary topological complexity. In mathematical terms, a knot is a closed, non-intersecting, curved line in three dimensions. Knots are typically described in mathematics in terms by their projections onto a plane. For non trivial knots, these projections contain "double points", which are points where the projected curve crosses itself. A knot can always be slightly perturbed in three dimensions so that, in projection, it has no triple or higher order points: that is, points where the projected curve crosses itself three or more times. Hence, knots can be described completely by giving such a two-dimensional projection, together with information about which piece of the curve crosses over or under the another piece at each double point.

The microfluidic networks provided according to the invention, because of their three-dimensional channel network structure, are able to provide a physical realization of the above-mentioned double point. In other words, the structures enable one channel, comprising a flow path or a segment of a flow path, to cross over or under another channel providing another flow path, a segment of another flow path, or providing another segment of the same flow path. Thus, the inventive microfluidic networks can provide a physical realization of essentially any topological knot system. Likewise, the inventive networks can provide a physical realization of essentially any arrangement of interlinked knots and of arbitrarily complex three-dimensional networks of interconnected channels whose projections onto a plane or surface, as explained in more detail below, can contain any arbitrary number of crossings. As shown and explained in more detail below, in order for the inventive microfluidic networks to avoid intersection of channels at their points of crossing in the planar projection, there typically are provided at least three identifiable "levels" within the structure: a "lower" level that contains a channel disposed therein that crosses "under" an "upper" level that contains disposed therein a channel that crosses "over" the channel contained in the bottom level, and an intermediate level that isolates the channels of the lower and upper levels and contains connecting channels penetrating therethrough that fluidically connect the channels in the lower level and the channels on the upper level in order to form a fluid flow path comprised of a series of interconnected channels. It should be understood that the terms "lower" and "upper" in the present context are intended to suggest only the relative positions of the various levels of the structure and are not meant to imply any particular orientation of the structure in space. For example the structure can be flipped, rotated in space, etc. so that the "lower" level is positioned above the "upper" level or the levels can be positioned side by side, etc. In yet other embodiments involving flexible structures, the structure can be twisted or bent thereby deforming planar levels into curved surfaces in space such that the "upper" and "lower" levels of the structure may be positioned differently with respect to each other at different locations in the overall structure. In order to produce microfluidic networks with arbitrarily complex channel networks, no additional levels are typically needed because triple, or higher order points in the projection are not necessary to allow the channels within the structure to cross over or under each other and thus cross each other in space without physical intersection of the "crossing" channels within the structure.

FIG. 1a illustrates one exemplary embodiment of an essentially infinite number of microfluidic network structures that can be produced according to the invention. Microfluidic network structure 100 includes a series of interconnected channels providing seven non-fluidically interconnected fluid flow paths. The channels are arranged in a "basket weave" arrangement. Channel system 100, as illustrated, includes three non-fluidically interconnected fluid flow paths, 102, 104, and 106 arrayed within planes parallel to the y-z coordinate plane, and four non-fluidically interconnected flow paths 108, 110, 112, and 114 arrayed within planes parallel to the x-z coordinate plane. Each fluid flow path of the structure comprises a series of interconnected channels (e.g. fluid flow path 102 comprises interconnected channels 113, 124, 126, 116, 118, 120, 128, 122 and 123 within structure 100).

Flow path 102, for example, includes two channels 116 and 122 disposed within the first, lower level of structure 100 and two channels 120 and 124 disposed within the second, upper level of the structure. Flow path 102 also includes a number of connecting channels, e.g. 118, 126, and 128 traversing a third, intermediate level of the structure and interconnecting channels contained in the first, lower level and second, upper level of the structure. The microfluidic network provided by structure 100 is truly three-dimensional because it cannot be produced by a two-dimensional structure comprising a series of interconnected channels disposed within a single plane or any stack or array of such structures. In other words, network 100 includes channels disposed within the first, lower level of the structure that are non-parallel to channels disposed within the second, upper level of the structure (e.g. channel 116 of fluid flow path 102 and channel 130 of fluid flow path 110). Another way to describe the three-dimensionality of network 100, and distinguish the network from those realizable in two-dimensional system, is to point out, that, for example, flow path 102 comprises a series of non-colinear interconnected channels disposed within a first plane of the structure, which is parallel to the y-z coordinate plane, and a second fluid flow path, for example, fluid flow path 108, is disposed within a second plane (parallel to the x-z coordinate plane as shown) that is not parallel with the first plane. Yet another way in which the microfluidic networks provided according to the invention differ from those realizable with two-dimensional systems is that the inventive microfluidic systems can include a fluid flow path therein having a longitudinal axis, defining a direction of bulk fluid flow within the flow path, that is not disposed within any single plane in space, nor is disposed within any a surface that is parallel to any surface (such as surface 132 or 134) of the microfluidic structure.

A "level" of a structure, as used herein, refers to a plane or curved surface within the structure, typically parallel to a top surface and a bottom surface of the structure, which can have a channel or series of channels disposed therein and/or penetrating therethrough. It should be understood that in the discussion and figures illustrated below, the microfluidic network structures are generally shown as having planar surfaces (e.g. surfaces 132 and 134), such that the levels within the structure are planar; however, many of the structures, as described in more detail below, are fabricated from flexible and/or elastomeric materials that are capable of being bent, twisted, or distorted from the illustrated planar configurations. For such embodiments, the "levels" within the structure will comprise curved surfaces that are parallel to the distorted planar surfaces of the structure, and any discussion herein with regard to "levels" of the structures should be understood to encompass such curved surfaces as well as the planar surfaces illustrated. "Parallel," when used in the context of comparing the topology of two surfaces in space, has its common mathematical meaning referring to the two surfaces being everywhere spaced apart from each other equidistantly.

"Non-fluidically interconnected" fluid flow paths, as used herein, refers to fluid flow paths each comprising one channel or multiple, fluidically interconnected channels, where the channels of different flow paths do not intersect and are physically isolated from each other within the structure so that they can not communicate fluid between each other through bulk mixing of fluid streams. A "fluid flow path" as used herein refers to one channel or a series of two or more interconnected channels providing a space within the microfluidic structure able to contain fluid or through which fluid can continuously flow. Each fluid flow path of the structure includes at least one opening thereto able to be placed in fluid communication with the environment external to the microfluidic structure and some preferred embodiments of fluid flow paths include at least two openings able to be placed in fluid communication with the environment external to the microfluidic structure, thus providing an inlet and an outlet. A "channel" as used herein refers to a flow path or continuous segment of a flow path, which is disposed within one or more levels of the microfluidic network structure and/or penetrates through one or more levels of the microfluidic network structure. "Interconnected channels," as used herein, refers to two or more channels within the structure that are able to communicate fluid between and through each other. A "non-linear" flow path and/or channel, as used herein, refers to such flow path or channel having a longitudinal axis that deviates from a straight line along its length by more than an amount equal to the minimum cross-sectional dimension of the channel or flow path. A "longitudinal axis" of a channel or flow path as used herein refers to an axis disposed along the entire length of such channel or flow path, which is coextensive with and defined by the geometric centerline of the direction of any bulk fluid which would flow through the channel or flow path should such channel or flow path be configured for fluid flow therethrough. For example, a linear or "straight" channel would tend to have a longitudinal axis that is essentially linear, while a fluid flow path comprising a series of such straight channels that are fluidically interconnected can have a longitudinal axis, comprising the interconnected longitudinal axes of the individual interconnected channels forming the fluid flow path, which is "non-linear." A channel which is "disposed within," "disposed in," "contained within," or "contained in" a level or multiple levels of the structure refers herein to such channel having a longitudinal axis that is coplanar with or, in the case of a level defined by a curved surface, is lying along a contour of the surface, of the level(s) in which it is disposed or contained. A channel that "penetrates," "penetrates through," or "traverses" a level or multiple levels of the structure refers herein to such channel having a longitudinal axis that is non-coplanar with or, in the case of a level defined by a curved surface, is not lying along a contour of the surface of the level(s) such that the longitudinal axis of such channel is non-parallel with any line that can be disposed within the level.

Fluid flow path 102 of microfluidic network 100 communicates with the external environment through an inlet opening 136 in fluid communication with bottom surface 134 and an outlet opening 138 in fluid communication with upper surface 132. The other fluid flow paths of the network have similar inlet and outlet openings, as illustrated.

The channels of the microfluidic networks provided according to the invention have at least one cross-sectional dimension that does not exceed about 500 μm, in other embodiments does not exceed about 250 μm, in yet other embodiments does not exceed about 100 μm, in other embodiments does not exceed about 50 μm, and in yet other embodiments does not exceed about 20 μm. A "cross-sectional dimension," when used in the above context, refers to the smallest cross-sectional dimension for a cross-section of a channel taken perpendicular to the longitudinal axis of the channel. While the channels of network 100 have cross-sectional dimensions that are essentially equal to each other, in other embodiments, the channels can have unequal cross-sectional dimensions, and some channels can have depths within the structure sufficiently great so that they are disposed in two or all three levels of the structure, instead of being disposed in only a single level, as illustrated. In addition, while in network 100 the channels are straight and linear, in other embodiments the channels can be curved within the level(s) in which they are disposed.

Figure 1B:
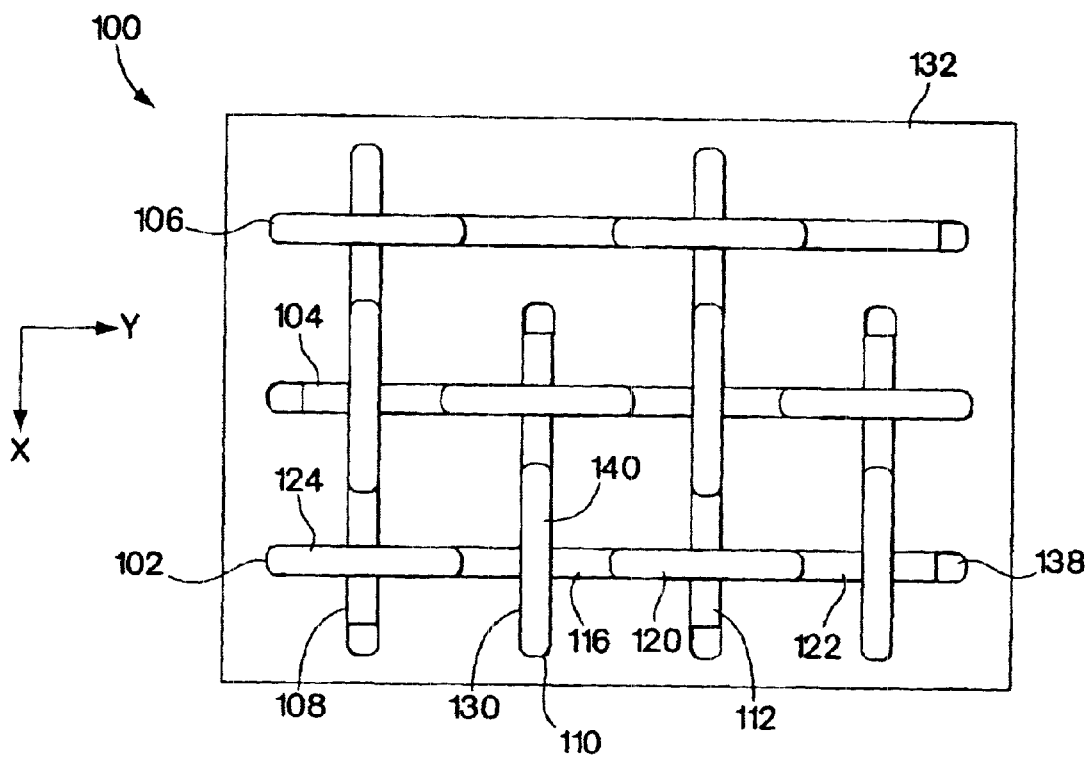

The double points formed where the channels of the fluid flow paths of network 100 cross over each other are more clearly seen in the two-dimensional perpendicular projection shown in FIG. 1b. FIG. 1b shows microfluidic network 100 as projected onto the y-x plane as viewed in the negative z-axis direction. Crossover double point 140, for example, represents the double point defining the cross over of channel 130 of fluid flow path 110 and channel 116 of fluid flow path 102. In general, microfluidic networks provided according to the invention having fluid flow paths including channels that "cross over" each other refers to structures including channel networks wherein a perpendicular projection of the channels onto a surface defining a level of the structure, in which either of the channels are disposed, at least partially overlap each other. A "perpendicular projection" refers to a projection in a direction that is perpendicular or normal to the surface being projected upon. "At least partially overlap" or "at least partially overlapping," as used herein when referring to projections of channels which cross over each other, refers to the two-dimensional projection of the channels intersecting each other, as shown by point 140 in FIG. 1b, or, if, for example, the channels are arranged in a parallel direction with respect to each other within the network structure, to their being at least partially superimposed upon each other in the two-dimensional projection.

While the three-dimensional microfluidic network structures described herein could potentially be fabricated via conventional photolithography, microassembly, or micromachining methods, for example, stereolithography methods, laser chemical three-dimensional writing methods, or modular assembly methods, as described in more detail below, the invention also provides improved fabrication methods for producing the inventive structures involving replica molding techniques for producing individual layers which comprise one or more of the levels of the structures, as discussed above. As described in more detail below, such layers are preferably molded utilizing mold masters having various features on their surface(s) for producing channels of the structure. In some preferred embodiments, the features are formed via a photolithography method, or can themselves comprise a molded replica of such a surface.

The microfluidic network structures produced by the inventive methods described herein can potentially be formed from any material comprising a solid material that comprises a solidified form of a hardenable liquid, and, in some embodiments, the structures can be injection molded or cast molded. As will be described in more detail below, preferred hardenable liquids comprise polymers or precursors of polymers, which harden upon, or can be induced to harden during, molding to produce polymeric structures. For reasons described in more detail below, particularly preferred polymeric materials for forming the microfluidic networks according to the invention comprise elastomeric materials.

For structures produced according to the preferred methods described herein, the microfluidic networks provided according to the invention will typically be comprised of at least one discrete layer of polymeric material, and other embodiments will be comprised of at least two discrete layers of polymeric material, and in yet other embodiments will be comprised of three or more discrete layers of polymeric material. A "discrete layer" of material as used herein refers to a separately formed subcomponent structure of the overall microfluidic structure, which layer can comprise and/or contain one, two, or three, or more levels of the overall channel network of the microfluidic structure. As described and illustrated in more detail below, the discrete layers of the structure can be stacked together to form a three-dimensional network, or multiple three-dimensional networks, if desired, and can also be, in some embodiments, placed between one or more support layers or substrate layers in order to enclose and fluidically seal channels of the lower and upper levels of the microfluidic structure.

As described in more detail below, the methods for producing microfluidic network structures provided by the invention can, in some embodiments, produce discrete layers comprising a single level of the overall structure, wherein the three-dimensional network structure is formed by forming a first layer including a series of channels disposed therein, forming a second layer including a second series of channels disposed therein, and forming a third layer having connecting channels traversing the layer, and subsequently stacking the third layer between above-mentioned first and second layers and aligning the layers with respect to each other to achieve the overall desired three-dimensional network structure. In another embodiment, the microfluidic network structure includes two channel-containing layers: a first discrete layer containing both a first level, including a series of channels disposed therein, and a third, intermediate level of the structure including the connecting channels traversing the level; and a second discrete layer including the second level of the structure, having a second series of channels disposed therein. In such a method the first discrete layer and the second discrete layer are stacked and aligned with respect to each other to produce the overall desired three-dimensional microfluidic network structure. And in yet a third embodiment, all three levels of the microfluidic network structure can be produced in a single discrete layer, the layer comprising a three-level microfluidic membrane structure.

Figure 2A:
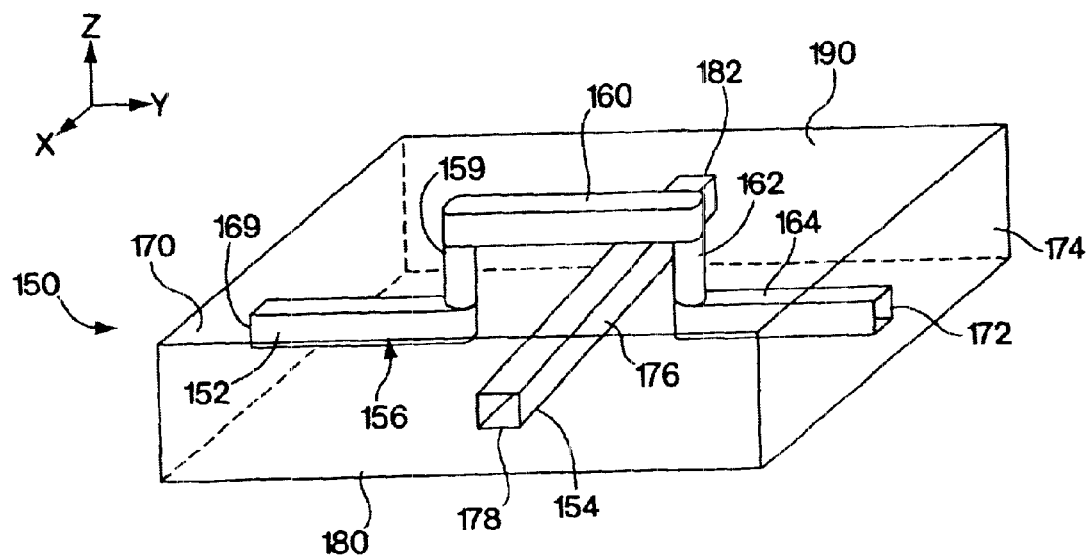
FIG. 2a is a perspective view of microfluidic network structure.
Figure 2B:
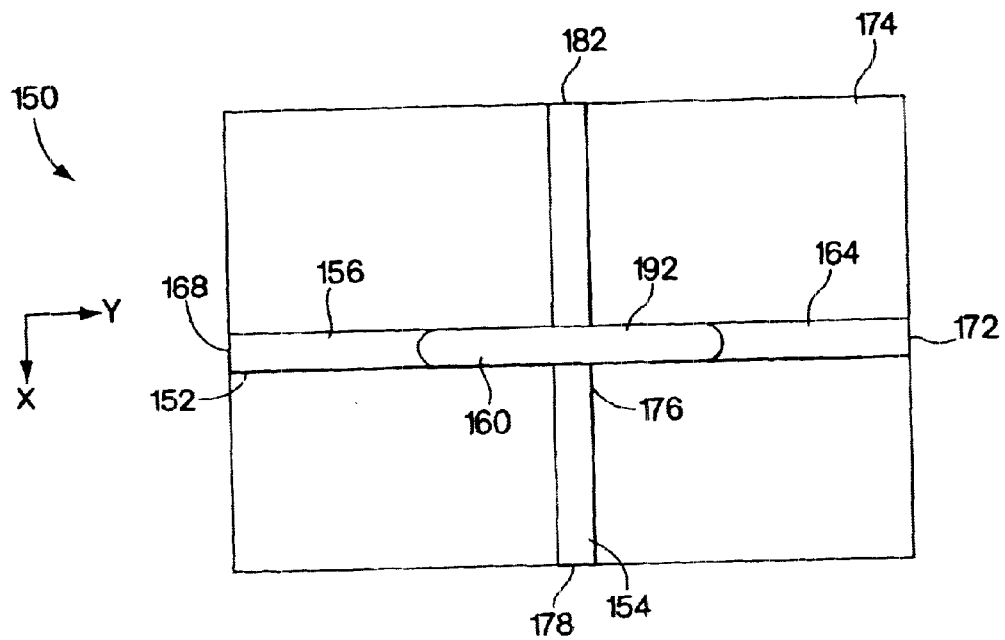

FIGS. 2a and 2b illustrate a microfluidic structure 150 having an alternative three-dimensional arrangement of channels therein. Microfluidic network 150 includes two non-fluidically interconnected flow paths 152 and 154. Fluid flow path 152 comprises a series of interconnected channels 156, 158, 160, 162 and 164, which are non-linear and which define a plane parallel to the y-z coordinate plane. Channels 156 and 164 are disposed within a first, lower level of the structure, and channel 160 is disposed within a second, upper level of the structure. Connecting channel 158 traverses a third, intermediate level of the structure from the first, lower level to the second, upper level and fluidically interconnects channel 156 to channel 160. Similarly, connecting channel 162 traverses the third, intermediate level of the structure connecting channel 164 and channel 160. Flow path 152 is connected in fluid communication with the external environment via inlet opening 168 in side wall 170 an outlet opening 172 in side wall 174. Fluid flow path 154 comprises a single channel 176 disposed within the first, lower level of the structure, and is interconnected to the environment via inlet opening 178 in side wall 180 an outlet opening 182 in side wall 190. The perpendicular projection of the microfluidic channel network, onto the first, lower level of the structure is illustrated in FIG. 2b. FIG. 2b shows double point 192 where channel 160 of fluid flow path 152 crosses over channel 176 of fluid flow path 154.

Figure 3A:
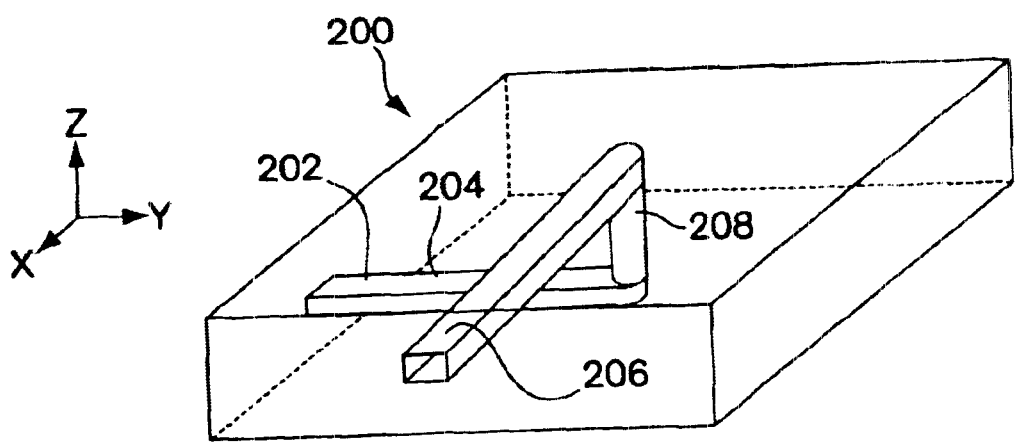
FIG. 3a is a perspective view of a schematic illustration of a third embodiment of a microfluidic network structure.
Figure 3B:
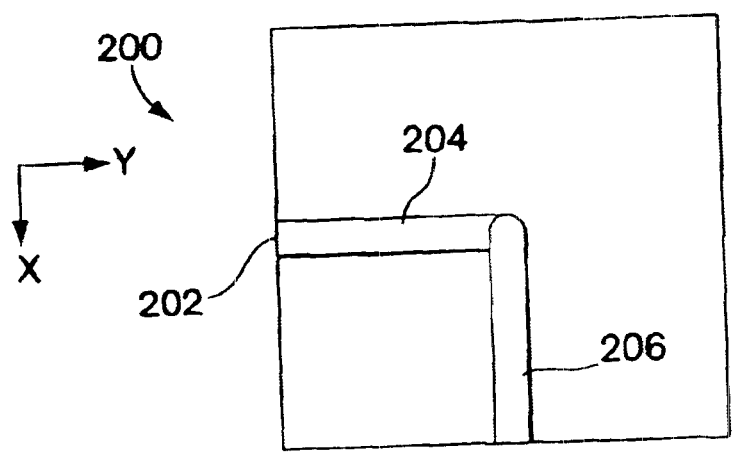

FIGS. 3a and 3b illustrate yet another simple microfluidic network provided according to the invention but not achievable with a conventional two-dimensional microfluidic network structure. Microfluidic network 200 includes a single fluid flow path 202. Fluid flow path 202 is comprised of a first channel 204 disposed within a first, lower level of the structure; a second channel 206 disposed within a second, upper level of the structure; and a connecting channel 208 traversing a third, intermediate level of the structure and fluidically interconnecting channels 204 and 206. Channel 204 disposed within the first level of the structure and channel 206 disposed within the second level of the structure are non parallel to each other and, in the illustrated embodiment, happen to be perpendicular to each other. FIG. 3b illustrates the perpendicular projection of microfluidic network 200 onto the first, lower level structure along the negative z-axis direction. As illustrated, microfluidic network 200 does not include any crossover points in the projection.

As previously discussed, a microfluidic network need only include three levels therein (a first and a second level including channels disposed therein such that their longitudinal axes are coplanar with a surface defining the level and a third intermediate level having one or more connecting channels passing therethrough fluidically connecting the channels of the first level and the second level) in order to provide any arbitrarily complex network of channels that pass over and under one another. However, certain potentially desirable geometric configurations of channels may require more than the three levels contained within the structures discussed and illustrated above. For example, if it is desired to produce a microfluidic network having channels disposed within three or more non-coplanar levels of the structure, additional levels are needed. In general, the number of levels required for microfluidic structures produced according to the invention required to produce n levels, each level having channels disposed therein such that their longitudinal axis are coplanar with the level, requires a total of 2n-1 total levels in the structure. Thus, for the previously illustrated embodiments having two levels therein in which channels are disposed, each structure requires a total of three levels to form the overall network structure (an upper and lower level in which the channels are disposed and an intermediate level through which the connecting channels pass).

Figure 4A:
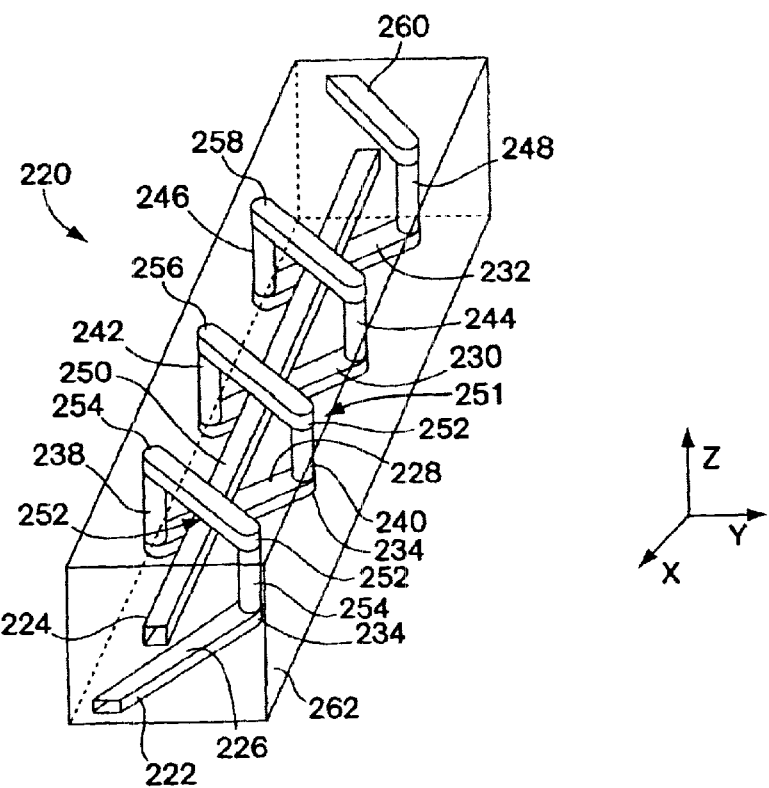
FIG. 4a is a perspective view of a schematic illustration of a five-level microfluidic network comprising a centrally disposed straight channel surrounded by a coiled fluid flow path.
Figure 4B:
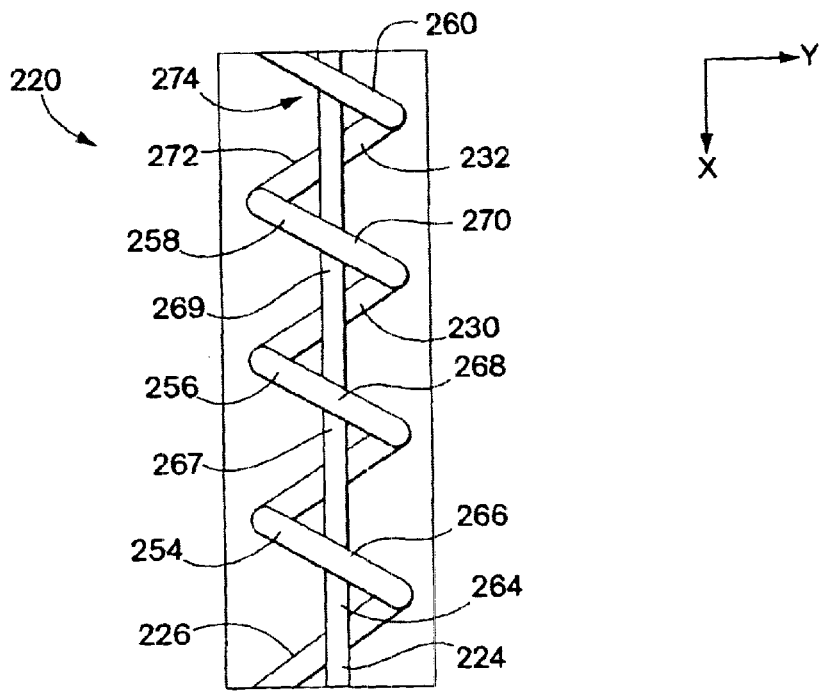

FIGS. 4a and 4b illustrate one embodiment of a microfluidic structure, producible according to the methods of the invention described below, including therein three levels having channels disposed therein such that their longitudinal axes are coplanar with each of the levels, and a total of five levels overall. Structure 220 includes a microfluidic network comprising a fluid flow path 222 arranged as a coil surrounding a second fluid flow path 224. Such an arrangement may be especially useful for particular microfluidic applications involving, for example, heat transfer or mass transfer between components contained within fluid flow paths 222 and 224, or for embodiments where electrical, magnetic, optical or other environmental interaction between materials in the respective flow paths is desired.

The first, lower level of structure 220 includes disposed therein channels 226, 228, 230, and 232 of coil flow path 222. The second level from the bottom of structure 220 includes disposed therethrough the lowermost region 234 of connecting channels 236, 238, 240, 242, 244, 246, and 248 of fluid flow path 222. The third level from the bottom of structure 220 includes channel 250 of fluid flow path 224 disposed therein and also includes intermediate region 251 of the connecting channels. The fourth level from the bottom of structure 220 includes, traversing therethrough, upper regions 252 of the connecting channels, and the uppermost level of structure 220 includes disposed therein channels 254, 256, 258 and 260 of flow path 222.

FIG. 4b illustrates the perpendicular projection of microfluidic network 220 onto a surface coplanar with the first, lowermost level of the structure that is parallel to the y-x coordinate plane, as viewed in the negative z direction. As illustrated, structure 220 includes 8 double point crossovers 264, 266, 267, 268, 269, 270, 272, and 274 where either flow path 224 crosses over a channel of flow path 222 (e.g. crossover points 264, 267, 269, and 272), or where channel 250 of flow path 224 crosses under a channel of fluid flow path 222, (for example, crossover point 266, 268, 270, and 274.) It should be evident that the five level structure illustrated by structure 220, in alternative embodiments, can have flow paths therein comprising a series of interconnected channels arranged so as to yield higher order crossover points than the double points illustrated. For example, in other embodiments, a five level structure can have channels disposed therein including triple point crossovers wherein a perpendicular projection onto a surface coplanar with a level of the structure includes points where three levels of channels intersect (i.e., where a channel disposed in the lowermost level, a channel disposed in the third, intermediate level, and a channel disposed in the uppermost level overlap and/or intersect each other in the two-dimensional projection).

As discussed above, the present invention also provides a variety of methods providing relatively simple and low cost fabrication techniques for producing the inventive microfluidic structures described herein. The preferred methods provided according to the invention and described below are based upon utilizing a hardenable liquid to create replica molded structures that comprise, or are assembled with other replica molded structures to form, the three-dimensional microfluidic network structures provided by the invention.

Figure 5A:
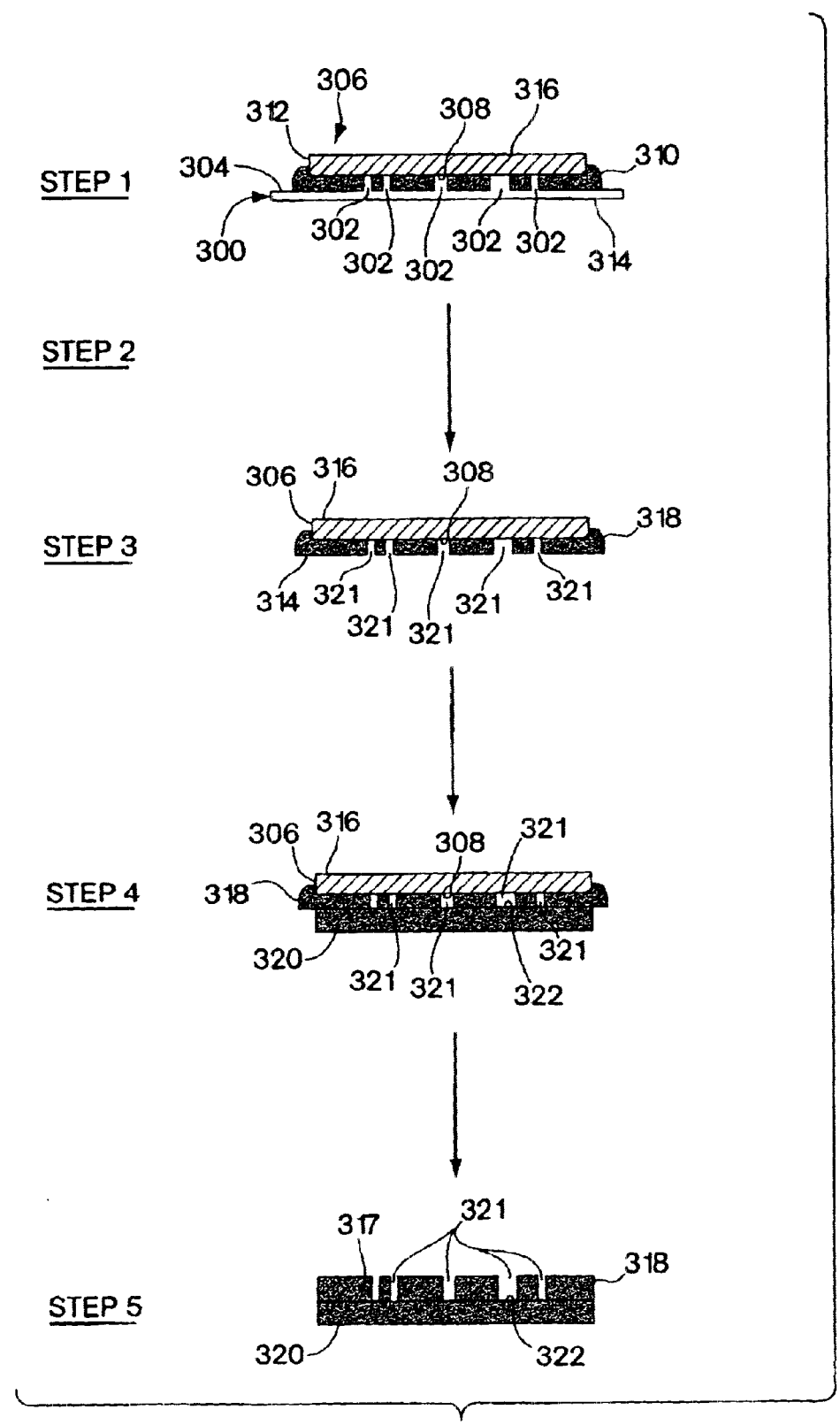
FIGS. 5a–5c are schematic illustrations of one embodiment of the fabrication method for forming a microfluidic network structure according to one embodiment of the invention.
Figure 5B:
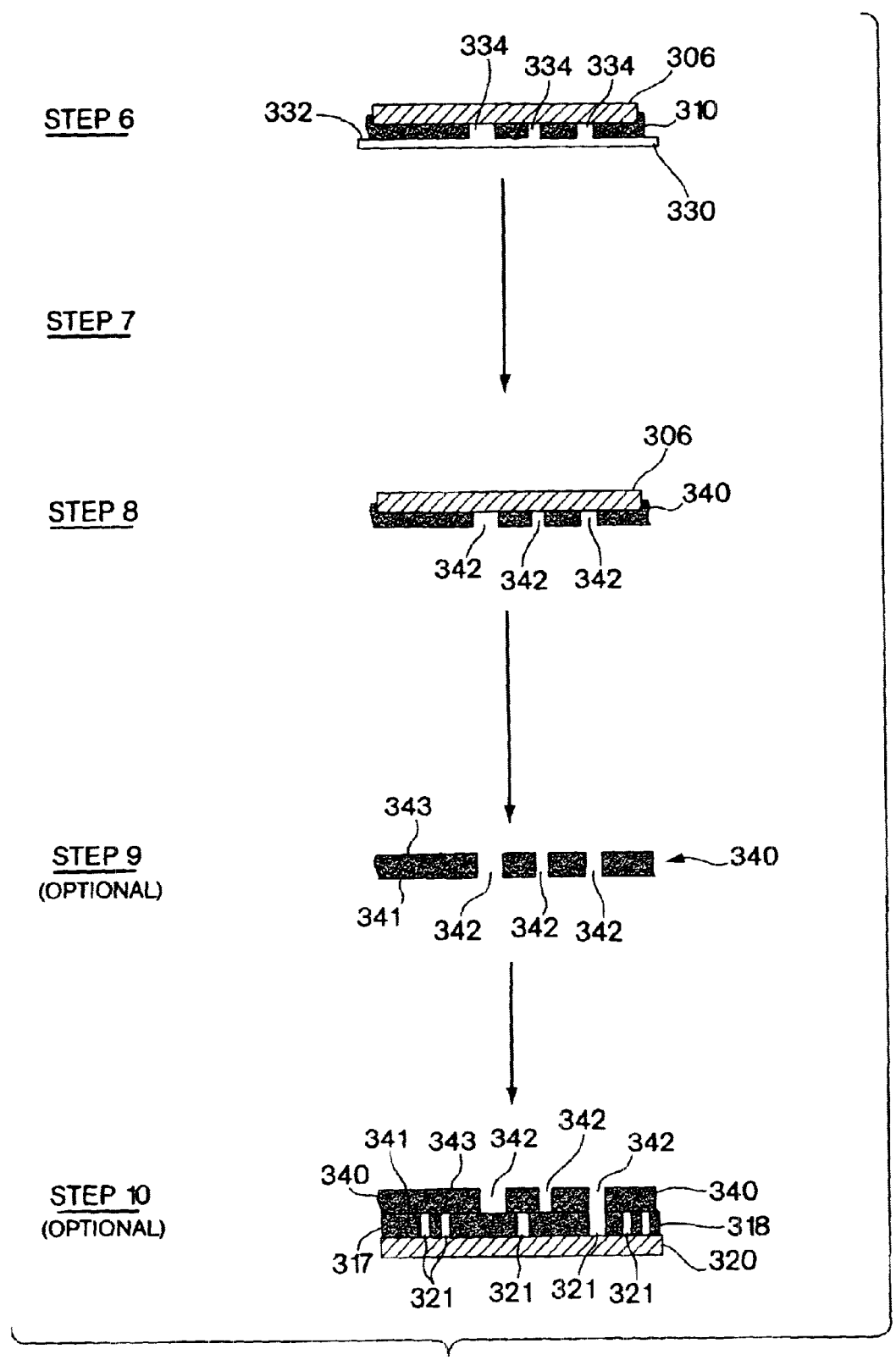
Figure 5C:
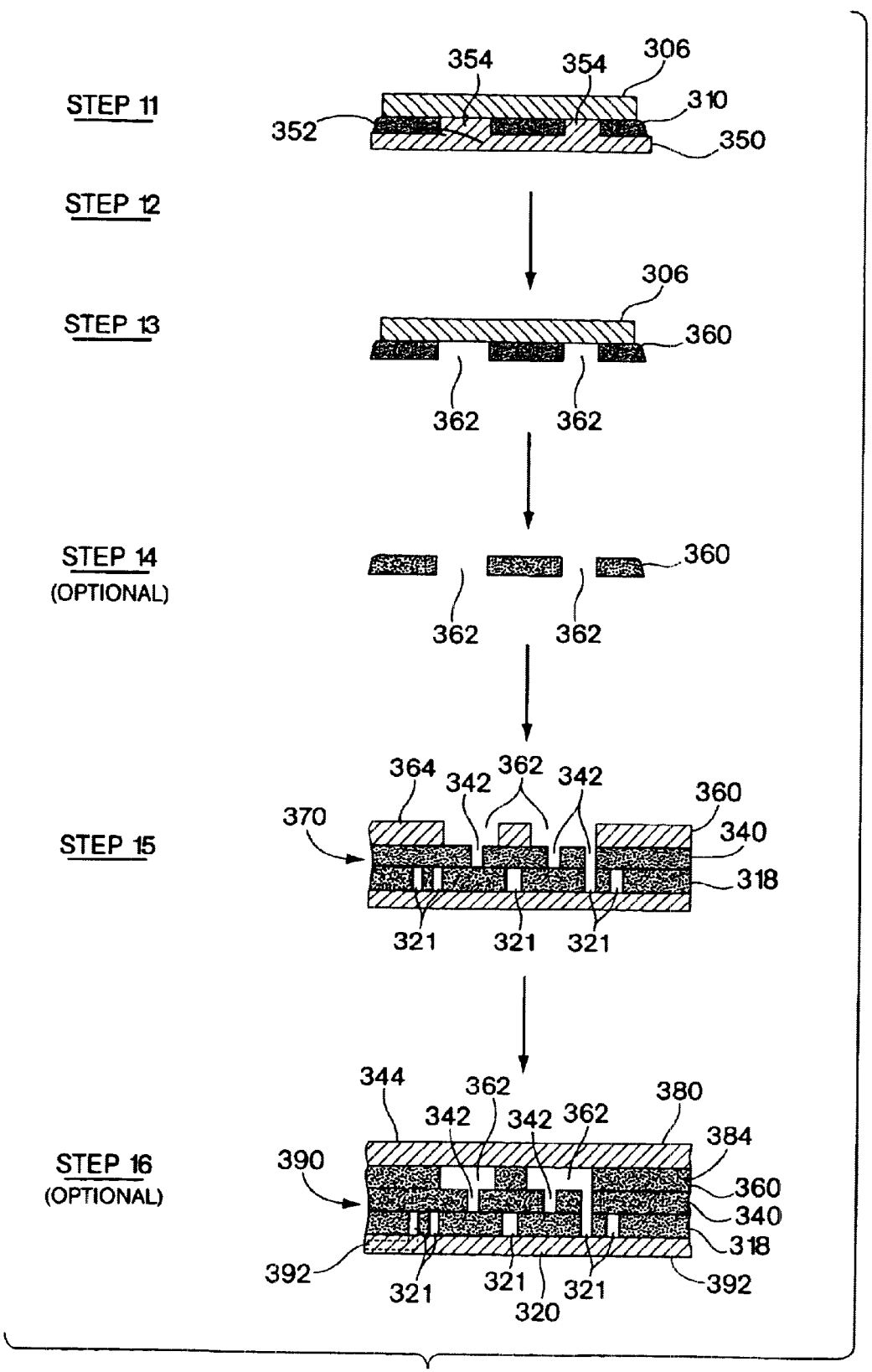

FIGS. 5a–5c illustrate a first embodiment of a method for forming the inventive microfluidic structures by utilizing a replica molding process provided by the invention. The method illustrated by FIGS. 5a–5c involves forming a number of replica molded layers from a hardenable liquid, each of which structures comprises a single level of the overall microfluidic network. Following the fabrication of each of the replica molded structures comprising layers of the overall microfluidic network structure, the layers are stacked upon each other, aligned with respect to each other so that the respective molded features in the layers create the desired and predetermined microfluidic network pattern, and, optionally, the layers can be permanently sealed to each other and/or to one or more substrate layers, which substrate layers do not comprise a level of the overall microfluidic structure, in order to yield a finished microfluidic network structure having a desired configuration.

Step 1 as illustrated in FIG. 5a involves forming a first layer of the structure comprising, for example, a first, lower level of the microfluidic network. Of course, in other embodiments, layers comprising an upper or intermediate level of the structure can be molded before or at the same time a lower layer is molded. In general, the order of the molding steps is not particularly critical and the various layers of the overall structure can be molded in any order that is desired or convenient. In the illustrated embodiment, a lower mold master 300 is provided having a series of topological features 302 protruding from an upper surface 304 of the lower mold master. A second mold master 306 having a flat, featureless surface 308 facing surface 304 of mold master 300 is provided and placed in contact with an upper surface of topological features 302 of mold master 304. Disposed between mold masters 304 and 306 is a layer of hardenable liquid 310, which upon solidification forms a replica molded layer including therein a plurality of channels, formed by topological features 302 of mold master 304, which, channels, in preferred embodiments, pass completely through the thickness of the entire layer of liquid 310, upon hardening, thus forming a membrane structure comprised of the hardened liquid.

Mold master 300, having positive, high-relief topological features 302 formed on a surface 304 thereof comprises, in some preferred embodiments, a substrate that has been modified, for example, via photolithography or any suitable micromachining method apparent to those of ordinary skill in the art. Topological features 302 are shaped, sized, and positioned to correspond to a desired arrangement of channels in the level of the overall microfluidic network structure being formed by the mold master. In one preferred embodiment, mold master 300 comprises a silicon wafer having a surface 304 that has been via photolithography utilizing a photomask having a pattern therewithin corresponding to a desired pattern of topological features 302. Techniques for forming positive relief patterns of topological features on silicon, or other materials, utilizing photolithography and photomasks, are well known and understood by those of ordinary skill in the art and, for example, are described in Qin, D., et al. "Rapid Prototyping of Complex Structures with Feature Sizes Larger Than 20 microns," *Advanced Materials*, 8(11):pp. 917–919 and Madou, M., *Fundamentals of Microfabrication*, CRC Press, Boca Raton, Fla., (1997), both incorporated herein by reference.

In a particularly preferred embodiment, mold master 300 comprises a silicon or other substrate, which has been spincoated with one or more layers of a commercially available polymeric photoresist material. In such preferred embodiments, topological features 302 can be easily, conveniently, and accurately formed in the layer(s) of photoresist forming surface 304 of substrate 300 via exposure of photoresist to radiation through a photomask and subsequent development of the photoresist material to remove photoresist material from the surface and regions surrounding features 302 thus leaving behind topological features 302 in positive relief. A variety of positive and negative photoresists can be utilized for such purposes and are well known to those of ordinary skill in the art.

One particularly preferred method for forming topological features 302 on a surface of a substrate coated with one or more layers of photoresist is described in more detail below in the context of FIG. 8. The photomask utilized, as described above, provides a pattern therein able to selectively block radiation reaching the layer(s) of photoresist so that, upon development of the layer, a pattern of topological features will be formed, which features correspond to a desired arrangement of channels within the replica molded layer. Such patterns can be designed with the aid of any one of a number of commercially available computer aided design (CAD) programs, as would be apparent to those of ordinary skill in the art.

Mold master 306 can be comprised of the same material as mold master 300; however, in preferred embodiments, mold master 306 is formed of an elastomeric material, for example, an elastomeric polymer. Mold master 306 is, in preferred embodiments, formed of an elastomeric material because the elastomeric nature of the mold master enables an improved seal at the interface of surface 308 of mold master 306 and the upper surfaces of topological features 302 of lower mold master 300 to be formed so as to essentially completely exclude hardenable liquid 310 from the interface between the topological features 302 and surface 308 of mold master 306. This preferred ("sandwich") method enables, upon the hardening of hardenable liquid 310, the production of a membrane comprised of the hardened fluid having channels disposed therein which completely traverse the entire thickness of the membrane and which are not blocked by a thin layer of hardened liquid.

For some embodiments, it is also desirable that upper mold master 306 be transparent in order to be able to visualize topological features 302 during the molding process. Alternatively, in other embodiments, upper mold master 306 can comprise a rigid, non-elastomeric material and lower mold master 300, including topological features 302 forming the channels of the molded structure, can be formed of an elastomeric material. In such an embodiment, the elastomeric mold master having positive relief topological features disposed on its surface is preferably itself formed as a molded replica of a pre-master having a surface including a plurality of negative, low-relief features therein, which form the positive relief features in the elastomeric mold master upon creating a replica mold of the pre-master surface. In yet other embodiments, the upper and lower mold masters of the invention can both comprise elastomeric materials and can be formed of the same, or different elastomeric materials. In addition, although less preferred, upper mold master 306 can be eliminated entirely and hardenable fluid 310 may simply be spuncast onto surface 304 of lower mold master 300 to a thickness corresponding to the height of topological features 302. Such method is generally less preferred for producing molded membranes according to the invention because it is generally desired that the uppermost and lowermost surfaces of the membrane be as flat and smooth as possible to enable conformal sealing and prevention of leakage upon assembly of the layers into the overall microfluidic network structure.

In preferred embodiments, hardenable liquid 310 is placed upon surface 304 of lower mold master 300 in an amount sufficient to form a layer over the region of surface 304 including topological features 302, corresponding to the channel structure in the layer to be formed, which layer having a thickness at least equal to the height of topological features 302 above surface 304. Subsequent to placing liquid 310 on surface 304, the method involves bringing surface 308 of upper mold master 306 into contact with the upper surface of features 302. In alternative embodiments, a lower mold master and upper mold master can be brought into contact prior to addition of the hardenable liquid, and the hardenable liquid can be applied to the region between the facing surfaces of the mold masters by adding a sufficient amount in the region of the space between the upper mold master and lower mold master around their periphery (e.g. periphery 312), and subsequently allowing hardenable liquid 310 to flow into the space surrounding the topological features of the mold master(s) via capillary action. Such method for utilizing capillary action for creating a molded replica structure as described in detail in commonly owned, copending U.S. patent application Ser. No. 09/004,583 entitled "Method of Forming Articles Including Waveguides Via , Capillary Micromolding and Microtransfer Molding," filed Jan. 8, 1998, now U.S. Pat. No. 6,355,198, and International Pat. Publication No. WO 97/33737, each incorporated herein by reference.

Hardenable liquid 310 can comprise essentially any liquid known to those of ordinary skill in the art that can be induced to solidify or spontaneously solidifies into a solid capable of containing and transporting fluids contemplated for use in and with the microfluidic network structures. In preferred embodiments, hardenable liquid 310 comprises a polymeric liquid or a liquid polymeric precursor (i.e. a "prepolymer"). Suitable polymeric liquids can include, for example, thermoplastic polymers, thermoset polymers, or mixture of such polymers heated above their melting point; or a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art.

In preferred embodiments, hardenable liquid 310 comprises a liquid polymeric precursor. Where hardenable liquid 310 comprises a prepolymeric precursor, it can be, for example, thermally polymerized to form a solid polymeric structure via application of heat to mold master 300 and/or mold master 306; or, in other embodiments, can be photopolymerized if either mold master 300 or mold master 306 is transparent to radiation of the appropriate frequency. Curing and solidification via free-radical polymerization can be carried out as well. These and other forms of polymerization are known to those of ordinary skill in the art and can be applied to the techniques of the present invention without undue experimentation. All types of polymerization, including cationic, anionic, copolymerization, chain copolymerization, cross-linking, and the like can be employed, and essentially any type of polymer or copolymer formable from a liquid precursor can comprise hardenable liquid 310 in accordance with the invention. An exemplary, non-limiting list of polymers that are potentially suitable include polyurethane, polyamides, polycarbonates, polyacetylenes and polydiacetylenes, polyphosphazenes, polysiloxanes, polyolefins, polyesters, polyethers, poly (ether ketones), poly(alkaline oxides), poly(ethylene terephthalate), poly(methyl methacrylate), polystyrene, and derivatives and block, random, radial, linear, or teleblock copolymers, cross-linkable materials such as proteinaceous materials and/or blends of the above. Gels are suitable where dimensionally stable enough to maintain structural integrity upon removal from the mold masters, as described below. Also suitable are polymers formed from monomeric alkylacrylates, alkylmethacrylates, alpha-methylstyrene, vinyl chloride and other halogen-containing monomers, maleic anhydride , acrylic acid, acrylonitrile, and the like. Monomers can be used alone, or mixtures of different monomers can be used to form homopolymers and copolymers. The particular polymer, copolymer, blend, or gel can be selected by those of ordinary skill in the art using readily available information and routine testing and experimentation so as to tailor a particular material for any of a wide variety of potential applications.

According to some preferred embodiments of the invention, hardenable liquid 310 comprises a fluid prepolymeric precursor which forms an elastomeric polymer upon curing and solidification. A variety of elastomeric polymeric materials are suitable for such fabrications, and are also suitable for forming mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1, 2-epoxide, or oxirane. For example, diglycidyl ethers of bisphenol A can be used, in addition to compounds based on aromatic amine, triazine, and cycloaliphatic backbones. Another example includes the well-known Novolac polymers. Examples of silicone elastomers suitable for use according to the invention include those formed from precursors including the chlorosilanes such as methylchlorosilanes, ethylchlorosilanes, and phenylchlorosilanes, and the like. A particularly preferred silicone elastomer is polydimethylsiloxane (PDMS). Exemplary polydimethylsiloxane polymers include those sold under the trademark Sylgard by Dow Chemical Co., Midland, Mich., and particularly Sylgard 182, Sylgard 184, and Sylgard 186.

Silicone polymers, for example, PDMS, are especially preferred for use in the invention because they have several desirable beneficial properties simplifying fabrication of the microfluidic network structures, described herein. First, such materials are inexpensive, readily available, and can be solidified from a prepolymeric liquid via curing with heat. For example, PDMSs are typically curable by exposure of the prepolymeric liquid to temperatures of about, for example, 65° C. to about 75° C. for exposure times of about, for example, 1 hour. Second, silicone polymers, such as PDMS, are elastomeric and are thus useful for forming certain of the mold masters used in some embodiments of the invention. In addition, microfluidic networks formed from elastomeric materials can have the advantage of providing structures which are flexible and conformable to the shape of a variety of substrates to which they may be applied, and elastomeric networks can provide reduced resistance to fluid flow for a given applied pressure drop, as compared to non-elastomeric structures, and can also be more easily fabricated to include active elements therein, for example integrated valves and pumping elements, which elements can utilize the flexibility and elasticity of the material for their performance.

Another distinct advantage for forming the inventive microfluidic networks from silicone polymers, such as PDMS, is the ability of such polymers to be oxidized, for example by exposure to an oxygen-containing plasma such as an air plasma, so that the oxidized structures contain at their surface chemical groups capable of cross-linking to other oxidized silicone polymer surfaces or to the oxidized surfaces of a variety of other polymeric and non-polymeric materials. Thus, membranes, layers, and other structures produced according to the invention utilizing silicone polymers, such as PDMS, can be oxidized and essentially irreversibly sealed to other silicone polymer surfaces, or to the surfaces of other substrates reactive with the oxidized silicone polymer surfaces, without the need for separate adhesives or other sealing means. In addition, microfluidic structures formed from oxidized silicone polymers can include channels having surfaces formed of oxidized silicone polymer, which surfaces can be much more hydrophilic than the surfaces of typical elastomeric polymers. Such hydrophilic channel surfaces can thus be more easily filled and wetted with aqueous solutions than can structures comprised of typical, unoxidized elastomeric polymers or other hydrophobic materials.

In addition to being irreversibly sealable to itself, oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention are described in more detail below and also in Duffy et al., *Rapid Prototyping of Microfluidic Systems and Polydimethylsiloxane*, Analytical Chemistry, Vol. 70, pages 474–480, 1998, incorporated herein by reference.

For clarity and simplicity, the discussion below involving the inventive methods for forming microfluidic structures according to the invention in many instances makes specific reference to a preferred embodiment wherein the layers comprising the structure and/or one or more mold masters are formed from a hardenable liquid comprising a fluid prepolymer of PDMS. It should be understood, as the discussion above makes clear, that such reference is pure exemplary, and a wide variety of other materials can be utilized in place of or in addition to PDMS to achieve the various objects, features, and benefits of the present invention, as would be apparent to those of ordinary skill in the art.

Referring again to FIG. 5a, in Step 2, PDMS, comprising hardenable liquid 310, is cured and solidified, for example by application of heat to raise the temperature of the PDMS prepolymer to between about 65° C. to about 75° C. for about 1 hour, as described above. In order to prevent seepage of the PDMS between surface 308 and the upper surface of topological features 302, it is preferred to apply pressure to one or both of lower surface 314 of mold master 300 and upper surface 316 of mold master 306. It has been found, within the context of the invention, that a pressure of approximately between about 10–100 g/mm$^2$ (100–1,000 kPa) or greater is generally sufficient to prevent PDMS prepolymer from seeping between topological features 302 and surface 308 so as to cause blockage of subsequent channels formed within the cured membrane.

Step 3 involves peeling the cured membrane from one or both of mold master 300 and 306. In preferred embodiments, as discussed above, materials are selected for mold master 300, mold master 306, and hardenable liquid 310, which allow removal of the solidified membrane upon solidification of the hardenable liquid without destruction of the molded structure. In especially preferred embodiments, because a solidified layer is typically thin and fragile (for example, layer 318 can vary in thickness from about 20 $\mu$m to about 1 mm), mold master 300 and mold master 306 are selected or treated such that layer 318 adheres to the surface of one of the mold masters more strongly than to the surface of the other mold master. Such differential adhesion allows the mold masters to be peeled apart such that the fragile molded layer 318 remains adherent to and is supported by one or the other of the mold masters. Such differential adhesion of layer 318 can be created by selecting materials comprising mold master 306 and surface 304 of mold master 300 having different chemical properties such that the non-covalent interfacial adhesion between layer 318 and surface 304 differs from that between layer 318 and surface 308. Those of ordinary skill in the art can readily determine appropriate materials for comprising hardenable liquid 310, mold master 300, and mold mater 306 and/or surface treatments which can be applied to either or both of the mold masters that allow for differences in non-covalent interfacial adhesion between layer 318 and the surfaces of the mold masters, enabling layer 318 to be selectively removed from one of the surfaces while remaining adherent to the other. Interfacial free energies for a wide variety of materials are readily available to those of ordinary skill in the art and can be utilized, along with routine screening tests, for example measuring forces required to peel apart various combinations of materials, by those of ordinary skill in the art to readily select a combination of materials, without undue experimentation, for enabling layer 318 to be selectively removed from the surface of one mold master while remaining adherent to and supported by the surface of the other mold master.

For example, in the illustrated embodiment, lower mold master 300 includes an upper surface 304 comprising a negative photopolymer (SU-8-50, Microlithography Chemical Corp., Newton, Mass.), upper mold master 306 comprises oxidized PDMS, and hardenable fluid 310 comprises a PDMS prepolymer. Also in the illustrated embodiment, surfaces 308 and 304, before contact with fluid 310 were silanized to facilitate the removal of PDMS replica layer 318 after curing. In an exemplary embodiment, the masters were silanized by exposing the surfaces to a chlorosilane vapor, for example a vapor containing tridecafluoro-1,1,2,2-tetrahydrooctal-1-trichlorosilane. PDMS replica layer 318 adheres more strongly to silanized PDMS mold master 306 than to silanized surface 304 of mold master 300 and remains supported by and attached to mold master 306 upon applying a peeling force tending to separate the two mold masters, resulting in molded replica layer 318 remaining adherent and supported by mold master 306, as illustrated in Step 3. In an alternative embodiment, instead of utilizing a silanized PDMS layer for mold master 306 in combination with silanized mold master 300, as described above, mold master 306 can comprise a layer or sheet of a material having a very low interfacial free energy, for example Teflon™ (polytetrafluoroethylene (PTFE)). In such an embodiment, replica molded layer 318 will tend to remain adherent to mold master 300 upon applying a peeling force tending to separate mold master 306 and mold master 300.

Step 4 of FIG. 5a illustrates an optional step comprising conformally contacting molded replica layer 318, supported by mold master 306, with a lower substrate layer 320, and, optionally, irreversibly sealing lower surface 319 of layer 318 to the upper surface 322 of substrate 320. In the illustrated embodiment, substrate 320 comprises a PDMS slab having a flat upper surface 322. Both lower surface 319 of layer 318 and upper surface 322 of substrate 320 have been oxidized, for example by exposure to an air plasma in a plasma cleaner, as discussed above and in more detail below, prior to bringing the surfaces into contact, so that when brought into conformal contact, an irreversible seal spontaneously forms between surface 319 and surface 322 providing a fluid-tight seal at the bottom of channels 321 in layer 318. Exposure of the PDMS surfaces to the oxygen-containing plasma is believed to cause the formation of Si—OH groups at the surface of the PDMS, which react with other Si—OH groups to form bridging, covalent siloxane (Si—O—Si) bonds by a condensation reaction between the two oxidized PDMS surfaces.

In alternative embodiments, where it is not desired to permanently seal layer 318 to substrate 320, the surfaces may not be oxidized so that they do not irreversibly seal to each other but rather may simply be brought into conformal contact with each other, which conformal contact between the two essentially flat planar surfaces can be sufficient, for microfluidic applications involving vacuum or low pressures, to form a fluid-tight seal. Also, in some applications, such as microcontact surface patterning with the inventive microfluidic networks as described in more detail below, it may be desirable to provide a "patterning" surface of the microfluidic network having channels therein which are not sealed by a substrate, and which can be brought into contact with a material surface in order to form on the surface a pattern defined by the channels in the "patterning" surface of the microfluidic network.

In yet other embodiments, substrate 320 can comprise a material different from one or both of molded layer 318 and mold master 306, for example, a material other than PDMS. In some such embodiments, substrate 320 can comprise, for example, the surface of a silicon wafer or microchip, or other substrate advantageous for use in certain applications of the microfluidic network provided according to the invention. Molded layer 318 can, as described above, be irreversibly sealed to such alternative substrates or may simply be placed in conformal contact without irreversible sealing. For embodiments where it is desired to irreversibly seal a molded replica layer 318 comprising PDMS to a substrate 320 not comprising PDMS, it is preferred that substrate 320 be selected from the group of materials other than PDMS to which oxidized PDMS is able to irreversibly seal (e.g., glass, silicon, silicon oxide, quartz, silicon nitride, polyethylene, polystyrene, epoxy polymers, and glassy carbon surfaces which have been oxidized). For embodiments involving hardenable liquids other than PDMS prepolymers, which form molded replica layers not able to be sealed via the oxidation methods described above, when it is desired to irreversibly seal such layers to each other or to a substrate, alternative sealing means can be utilized, as would be apparent to those of ordinary skill in the art, including, but not limited to, the use of separate adhesives, thermal bonding, solvent bonding, ultrasonic welding, etc.

Step 5 illustrated in FIG. 5a comprises the removal of upper mold master 306 to expose flat, top surface 317 of molded replica 318 thus yielding a first, lower level of the overall microfluidic network structure having a series of channels 321 disposed in a desired pattern therein. In an alternative embodiment to the illustrated membrane sandwich method for forming membrane layer 318, in Step 1 a molded replica can be formed by placing mold master 300 in the bottom of a dish or other container having a depth in excess of the height of topological features 302 and filling the container to a level in excess of the height of features 302 with a hardenable liquid, such as PDMS prepolymer. Upon curing and removing the cured structured from the container and from mold master 300, a structure similar to that obtained at the end of Step 5 is formed, except comprising channels that do not penetrate through the entire thickness of the molded replica layer. Such an embodiment is described in further detail in the context of the fabrication method illustrated in FIG. 7 below. In addition, as illustrated in FIG. 5, to facilitate the stacking and alignment of additional molded replica layers comprising the second, third, and any higher levels of the microfluidic structure, lower layer 318 can be trimmed such that it is essentially uniform in thickness and has a desired overall size and perimeter shape.

FIG. 5b illustrates the formation of a second molded replica layer comprising the third, intermediate level of a microfluidic network structure containing therein connecting channels as previously described. Steps 6–8 are essentially similar to Steps 1–3 described above in the context of FIG. 5a, except that lower mold master 330 has an upper surface 332 including thereon positive relief topological features 334 protruding above surface 332 that are shaped, sized, and positioned to form channels within the molded replica structure corresponding to a desired arrangement of connecting channels within the third, intermediate level of the microfluidic network structure being fabricated. In addition, if desired, additional features (not shown) can be included on the surface 332 of mold master 330 corresponding to channels that are disposed within (i.e., have longitudinal axis coplanar with) the third, intermediate level of the microfluidic network structure being formed.

Step 7 involves curing PDMS prepolymer 310 (or other hardenable liquid) as previously described for Step 2 above, and Step 8 involves selectively removing molded replica layer 340 from mold master 330 while it remains supported by an adherent to upper mold master 306, as described for Step 3 above. Optional step 9 involves removing molded replica layer 340 from upper mold master 306 and, if desired, trimming layer 340 so that it has an essentially identical overall size and perimeter shape as layer 318 above. Step 10 involves placing molded replica layer 340 into conformal contact with upper surface 317 of molded replica layer 318, aligning the channels 342 in molded replica layer 340 with channels 321 in molded replica layer 318 to provide a desired registration between the channels of the first, lower level of the structure comprised of layer 318 and the third, intermediate level of the structure comprised of layer 340, followed by irreversibly sealing together layers 318 and 340. In alternative embodiments, the alignment and sealing steps can be delayed if desired and performed in one step for all of the layers (i.e., all three channel-forming layers) comprising the overall structure which have been formed and stacked upon each other (e.g. see FIG. 5c below). In addition, for embodiments wherein upper mold master 306 is transparent, for example for embodiments where upper mold master comprises PDMS, and especially for embodiments including replica layers having a large number of channels disposed completely through the entire thickness of the membrane layer or having channels shaped so that the molded replica membrane layer is not free-standing when removed from a support surface (e.g., channels comprising continuous, closed geometric shapes, spiral shaped channels, etc.), layer 340 is preferably not removed from mold master 306 as illustrated in Step 9, but instead, mold master 306, with molded replica layer 340 attached thereto, is placed in contact with upper surface 317 of molded replica layer 318 and aligned and sealed as described in step 10 prior to removing mold master 306, so that the molded replica layer remains attached to and supported by a mold master during each of the manipulation steps and is never free-standing.

Alignment of the molded replica features comprising the channels of layers 318 and 340 can be accomplished utilizing a microscope, such as a stereo microscope, in combination with an alignment stage and/or micromanipulators for accurately positioning the layers and registering the features with respect to each other. For a preferred embodiment wherein layers 318 and 340 are comprised of PDMS, layers 318 and 340 can be aligned and sealed to each other by either of the preferred methods described directly below. In a first method, layer 340 is placed upon layer 318 and carefully aligned with respect to layer 318 to provide a desired alignment and registration of channels by utilizing a stereo microscope and a micromanipulator. Layers 318 and 340 are then carefully slightly separated from each other (e.g. by a few millimeters), without changing the registered lateral alignment of channels within the layers, to provide a small space between surface 317 of layer 318 and surface 341 of layer 340. The aligned structure having the layers slightly separated is then exposed to an oxygen-containing plasma in order to oxidize surfaces 317 and 341. The layers are then carefully brought together without altering or disturbing the lateral alignment of the channels, so that surfaces 317 and 341 spontaneously seal to each other upon conformal contact.

In the second, especially preferred, embodiment, alignment and sealing of the layers proceeds as follows. The upper surface 317 of layer 318 and lower surface 341 of layer 340 are oxidized utilizing the oxygen-containing plasma exposure method described previously, and a liquid that is essentially non-reactive with the oxidized surfaces is placed upon layer 317 to form a continuous layer of liquid thereupon, upon which, surface 341 of layer 340 is placed. The liquid, in addition to being essentially non-reactive with the oxidized surfaces of the PDMS, also preferably prevents degradation of the active Si—OH groups present on the surfaces for a period of time sufficiently long to enable alignment of the surfaces with respect to each other and removal of the liquid. After placing layer 340 onto the fluid-covered surface of layer 318, layer 340 is aligned with respect to layer 318 to yield a desired registration and alignment of features (channels) for forming the microfluidic network structure. The non-reactive liquid is then removed from between the two surfaces bringing the two surfaces into conformal contact with each other and spontaneously sealing the two surfaces together.

A variety of liquids can potentially be utilized as the non-reactive liquid in the context of the inventive alignment method above described. As previously discussed, appropriate liquids will be essentially non-reactive with the oxidized surfaces and will preferably stabilize and delay degradation of the active chemical groups contained within the oxidized surfaces. It has been found, in the context of the present invention, that polar liquids, and especially those comprising compounds including hydroxyl moieties, are effective for use as the non-reactive liquid. Especially preferred are water, alcohols, and mixtures thereof with alcohols, and alcohol-water mixtures being particularly preferred, especially those including methanol and/or trifluoroethanol. The non-reactive liquid, in preferred embodiments, is removed from between the oxidized surfaces of the layers via evaporation of the liquid, and thus, in such embodiments, as the non-reactive liquid evaporates the oxidized surfaces of the layers are simultaneously brought together in conformal contact whereupon the surfaces react to create an essentially irreversible seal.

While we have described above an embodiment wherein layer 340 comprising the third, intermediate layer of the structure is aligned and sealed with respect to layer 318 comprising a first, lower level of the structure prior to the fabrication of the molded replica layer comprising a second, upper level of the structure, in other embodiments, as mentioned above, the upper layer is formed prior to sealing the lower and intermediate layers together, so that the intermediate and upper layers can be stacked, aligned, and sealed to the lower layer in a single step, eliminating the need to selectively oxidize only lower surface 341 of intermediate layer 340 so as to prevent degradation of an oxidized upper surface 343 of intermediate layer 340 prior to the formation, stacking, and alignment of the upper layer to the intermediate layer (as shown and described in FIG. 5c below).

FIG. 5c illustrates the final steps for forming the overall three-layer, three-level microfluidic network according to this first fabrication method embodiment of the invention. Step 11 and Step 12 of FIG. 5c are analogous to Steps 1 and 2 of FIG. 5a and Steps 6 and 7 of FIG. 5b and involve sandwiching a hardenable liquid 310, such as PDMS, between upper mold master 306 and a lower mold master 350 having an upper surface 352 including thereon topological features 354 in positive relief constructed and positioned for forming channels disposed within the second, upper level of the final overall microfluidic network structure. Hardenable liquid 310 is cured and solidified in Step 12, as previously described, and, in preferred embodiments, molded replica layer 360 is preferentially separated from surface 352 of lower mold master 350 while remaining in contact with and supported by upper mold master 306, as previously described. Molded replica layer 360, which comprises the second, upper level of the overall structure, includes molded channels 362 disposed within layer 360. Step 14 involves optionally removing molded replica membrane layer 360 from upper mold master 306, as previously described for Step 9 discussed in the context of FIG. 5b. In step 15, molded replica layer 360, formed in Step 12 above, is stacked upon intermediate layer 340, produced as described in the context of FIG. 5b above, and is subsequently aligned with respect to lower layers 340 and 318 such that channels 362 are registered and arranged in a desired alignment with respect to channels 342 of layer 340 and channels 321 of layer 318 to provide a desired overall three-dimensional fluidic network structure. Layer 360 is preferably sealed to layer 340 by utilizing one of the aligning and sealing methods previously described in the context of Step 10 of FIG. 5b above.

As previously mentioned, in some preferred embodiments, layer 340 is aligned with respect to layer 318 and layer 360 is aligned with respect to layer 340 and the layers are sealed together in a single step after alignment, which step, for such embodiments, can take place at Step 15 of FIG. 5c. In such embodiments, layer 340 would not be irreversibly sealed to layer 318 prior to the addition of layer 360 to the stack and alignment of layer 360 with respect to layer 340 and 318. In such embodiments, wherein layers 340 and 360 are both aligned and sealed in a single step, the alignment and sealing methods utilized can be essentially the same as those previously described for aligning and sealing layer 340 to layer 318 in the context of Step 10 of FIG. 5b. In addition, in some embodiments where it is desired to irreversibly seal together some portions of the surfaces of the layers of the structures while leaving non-irreversibly sealed other portions, such portions which are not desired to be irreversibly sealed can be coated with a protective coating (e.g. petroleum jelly) prior to oxidation in order to prevent oxidation of that portion of the surface so that it will not irreversibly seal to other oxidized surfaces upon contact.

Also provided, according to the invention, is a method for self-aligning layers 318, 340, and 360 with respect to each other to provide a desired alignment and registration of the channels within each of the layers, without the need for manual alignment with the aid of a microscope and/or micromanipulator. The self-alignment method provided according to the invention can be utilized for the embodiments described above wherein the layers are oxidized and separated from each other by a layer of liquid during alignment of the layers. Details of this self-alignment method are described below in the context of FIG. 6 and rely on the interaction between the surface tension of the liquid between the layers and specific alignment features provided within the layers being aligned.

Microfluidic network structure 370 obtained at the conclusion of Step 15 of FIG. 5c can comprise, for some embodiments, a complete structure, useful, for example, for applications wherein it is desired that channels 362 in layer 360 remain uncovered and exposed to the surroundings. For example, one particular embodiment utilizing a microfluidic network structure similar in configuration to structure 370 involves utilizing the microfluidic network structure as a stamping template for selectively applying a fluid to a material surface to create a pattern on the material's surface corresponding to the pattern of channels 362 in layer 360. In such embodiments, surface 364 of layer 360 comprises a stamping surface, which is placeable in contact with a material surface for forming a pattern thereon, and microfluidic network structure 370 comprises a three-dimensional microfluidic stamp. Specific uses and patterns producible by such microfluidic stamps are described in greater detail below.

For other embodiments where it is desired to form a microfluidic network structure having an enclosed network of channels, optional Step 16 of FIG. 5c involves contacting upper surface 364 of layer 360 with an upper substrate layer 380 to form enclosed microfluidic network structure 390. In some preferred embodiments, where layers 318, 360, and 364 comprise PDMS, upper substrate layer 380 is also comprised of PDMS and is irreversibly sealed to surface 364 via the self-sealing method utilizing oxidation of the PDMS surfaces with an oxygen-containing plasma described in detail above. In alternative embodiments, however, upper substrate layer 380 may simply be placed in conformal contact with upper layer 364 and not irreversibly sealed thereto. In addition, upper substrate 380, in some embodiments, is not formed of the same material (e.g., PDMS) as layers 318, 360, and 364 of the structure. Upper substrate 380 can be essentially any of the materials mentioned previously for comprising substrate layer 320 previously described above in the context of FIG. 5a or any other substrate which can contact surface 364 conformally.

In order to provide fluid communication between channels contained within layers 318, 360, and 364 of structure 390 and the surrounding environment, lower substrate layer 320 and/or upper substrate layer 380 can include, formed therein, inlet/outlet conduits 392 providing fluid communication between the channels of the structure and the external environment. Conduits 392 can be formed within substrate layer by a variety of machining and/or molding methods, as would be apparent to those of ordinary skill in the art. In one embodiment, the conduits 392 in substrate 320, comprising PDMS, are formed by carefully boring into layer 320 with a small diameter syringe needle. In other embodiments, substrate layer,392 can itself comprise a replica molded structure with conduits 392 corresponding to and formed by topological features present on a surface of a mold master utilized to form substrate layer 320. In addition, as would be apparent to those of ordinary skill in the art, other features can be machined within, or molded within one or both of substrate layers 320 and 380 to provide various desired structures and functions for particular applications. For example, upper substrate layer 380 as shown includes traversing therethrough a small diameter channel 394, having a characteristic cross sectional dimension on the order of a few microns to a few tens of microns, which conduit 394 serves the function of providing a relief valve to prevent over pressure of the channels contained within the structure defined by layers 318, 340, and 360.

Figure 6A:
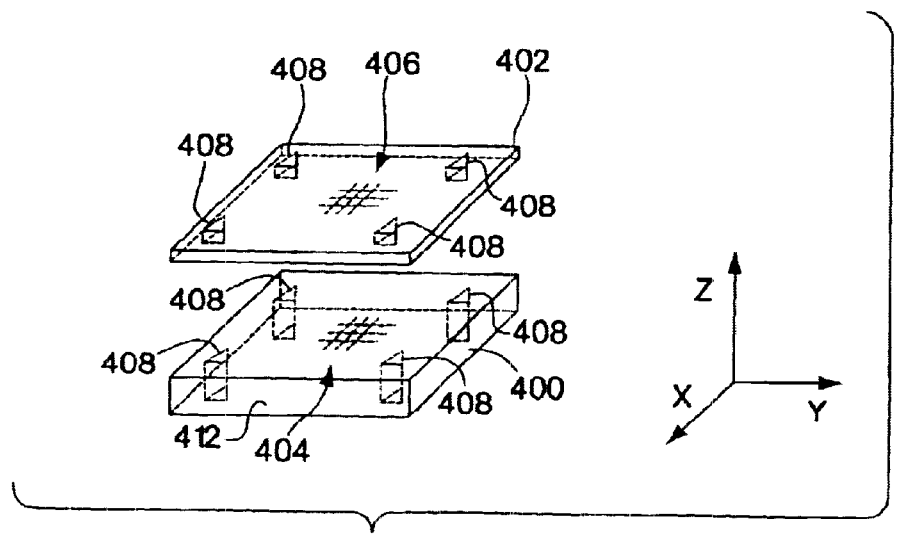
FIGS. 6a–6c are schematic illustrations of one embodiment of a self-aligning method provided by the invention.
Figure 6B:
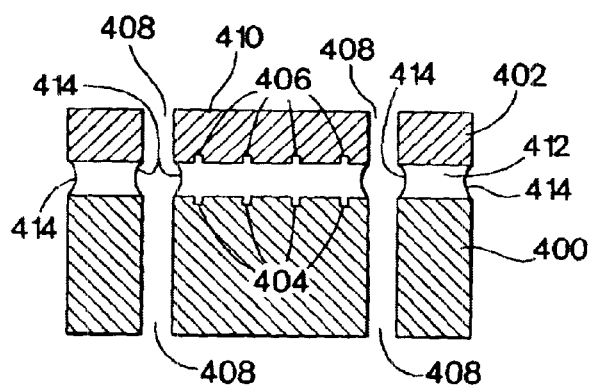
Figure 6C:
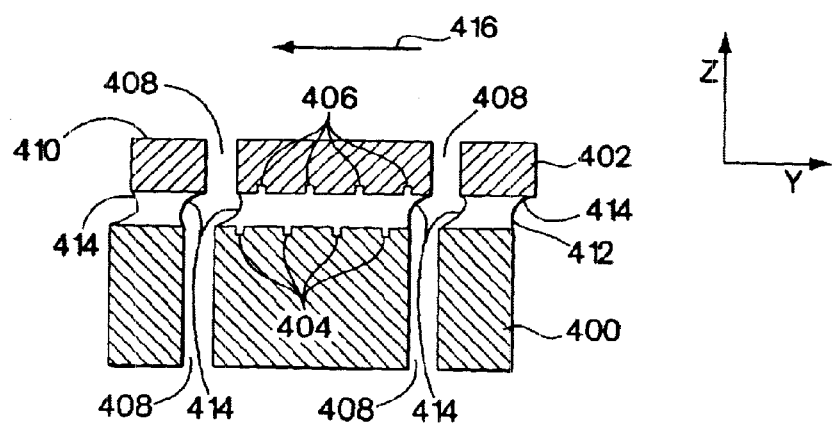

FIGS. 6a–6c illustrate one method for self-aligning various layers of the microfluidic network structures with respect to each other provided by the invention. The self-alignment method outlined in FIGS. 6a–6c can be utilized for embodiments involving the alignment and sealing methods discussed above involving disposing layers of the structure separated from each other by a layer of liquid disposed therebetween. Such a method is useful, for example, for aligning layers 340 and 318 with respect to each other and layers 360 and 340 with respect to each other in the previously described microfluidic network fabrication method. In addition, the self-alignment method described in FIGS. 6a–6c can also be utilized for performing self-alignment in the context of the methods described below in FIG. 7 and FIG. 10.

One embodiment for implementing the self-aligning method provided according to the invention is illustrated in FIG. 6a. FIG. 6a shows a first layer 400 and a second layer 402 including therein replica molded features 404 and 406 respectively, comprising, for example, channels disposed within each of the layers, which channels are desired to be registered and aligned with respect to each other in a certain way. In the illustrated embodiment, a plurality of self-alignment elements 408 are formed at selected, predetermined locations within layer 400 and layer 402. In the illustrated embodiment, self-alignment features 408 comprise vertically disposed channels traversing, in some preferred embodiments, essentially completely through layers 400 and 402 such that upon bringing layer 402 into conformal contact with layer 400 upper surface 410 of layer 402 is in fluid communication with lower surface 412 of layer 400 through vertically disposed channels formed by the alignment of the self-alignment elements contained within layers 400 and 402 respectively. In other embodiments, one or more of the alignment elements may not completely traverse the layer in which it is disposed, but may instead comprise an indentation, bump, or other feature within or on the surface of the layer.

In order to effect proper self-alignment, it is important that layers 400 and 402 be essentially identical in size and perimetric shape, when viewed in the x-y plane along the negative z-axis direction as illustrated, such that the perimeter of layers 402 and 400 essentially identically overlap when the layers are brought together into properly aligned conformal contact. Optionally, in other embodiments, proper self-alignment can also be effected if, instead of being essentially identical in size and perimetric shape, one of the layers is much larger than the other so that the meniscus of liquid formed around the edge of the smaller layer does not change appreciably in total surface area with small movements of the two layers with respect to each other.

Self-alignment elements 408, in preferred embodiments, are formed within layers 400 and 402, during the replica molding process for forming the layers, by topological features provided within the mold masters utilized for molding. Such topological features can be positioned and located within the mold master surface at selected, strategic positions with respect to features within the mold master surface for forming channels 404 and 406 through use of a CAD computer program, such as described above for designing the overall layout of the topological features for forming the various channels within the replica molded layer structures. Topological features forming self-alignment elements 408 are positioned with respect to topological features forming channel structures 404 and 406 so that when layer 400 and layer 402 are superimposed such that alignment holes 408 are precisely aligned with respect to each other, channel features 404 and 406 are also oriented with respect to each other in a desired registered alignment.

FIG. 6b and FIG. 6c illustrate the manner by which alignment holes 408 interact with a fluid layer 412 disposed between layers 400 and 402 to effect self-alignment. When self-alignment holes 408 and features 404 and 406 are properly aligned with respect to each other, as shown in FIG. 6b, the layers are arranged in an equilibrium position in which the interfacial area 414 between fluid layer 412 and the surrounding gaseous environment is minimized and there are no net capillary forces, due to the surface tension of fluid layer 412, tending to change the position of layer 400 or layer 402 with respect to each other.

By contrast, when features 404, 406, and self-alignment holes 408 are misaligned with respect to each other, as illustrated in FIG. 6c, the interfacial area 414 between fluid layer 412 and the surrounding gaseous atmosphere is increased with respect to the interfacial surface area when the system is in its equilibrium position as shown in FIG. 6b above, and there will be a net resulting capillary force in the direction shown by arrow 416, due to surface tension effects of fluid layer 412, tending to bring the system into the equilibrium position illustrated in FIG. 6b.

Figure 6D:
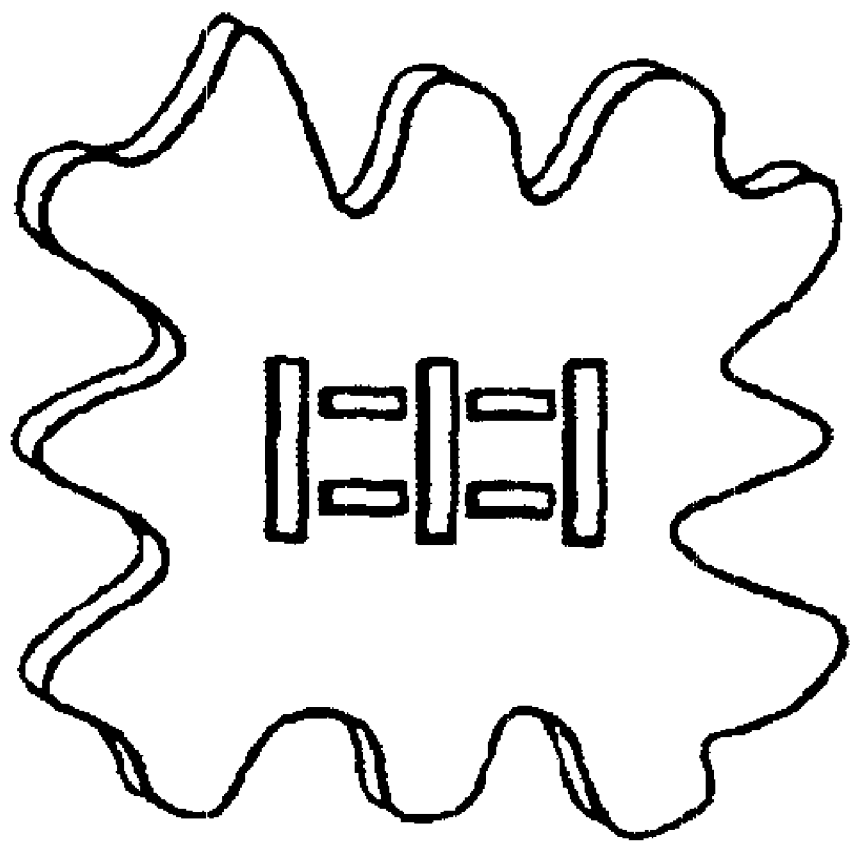
FIG. 6d is a schematic illustration of a replica molded layer of a microfluidic network having a perimetric shape for use in one embodiment of a self-aligning method according to the invention.

In alternative embodiments, an essentially identical self-aligning effect as illustrated in FIGS. 6a–6c can be achieved without the need for forming self-alignment holes or features, such as 408, in the layers which are to be self-aligned with respect to each other. In such alternative embodiments, the layers can be formed without self-alignment holes, such as 408, but instead be formed or trimmed to have perimeter shapes, which are essentially identical to each other, so that the layers when stacked upon one another with a fluid layer therebetween, as illustrated in FIGS. 6b and 6c, will have a minimum free energy equilibrium position defined by an essentially precise and exact overlay of the essentially identical perimetric shapes of the two layers. The features comprising channels within the layers are, in such embodiments, strategically positioned with respect to the peripheral border of the layers, so that, when the layers are aligned in the above-described minimum energy, no net capillary force equilibrium position, the perimeters of the layers are precisely superimposed upon each other and the features comprising the channels within the layers are also similarly aligned with respect to each other in a desired registration. FIG. 6d illustrates one contemplated embodiment of a perimetric shape for enabling the above-described self-alignment of various layers of the structure without the need for alignment holes.

The above-described self-alignment techniques are able to self-align a stack of as many individual layers as is desired, essentially simultaneously and in parallel. The self-alignment technique described herein is also capable of self-aligning elements with respect to each other within a margin of error of approximately +/–10 ||m or less, providing sufficient alignment precision for most of the channel sizes and configurations contemplated for the structures provided according to the invention (e.g., channel structures having a cross-sectional dimension ranging from about 20 $\mu$m to about 500 $\mu$m). The alignment precision obtainable by the above-described self-alignment technique is typically comparable or better than that obtainable via manual alignment techniques utilizing a stereomicroscope and conventional micromanipulation equipment.

The above-described self-alignment techniques are especially well suited for embodiments involving alignment of oxidized PDMS layers utilizing the above-described alignment/sealing method using a non-reactive liquid disposed between and able to wet the oxidized PDMS layers. However, those of ordinary skill in the art will readily realized that the above-described self-alignment technique can be utilized for aligning layers comprised of essentially any of the suitable materials for forming the microfluidic system discussed above and can be utilized for self-aligning layers that are not reactive with respect to each other and do not become essentially irreversibly sealed to each other upon contact but, instead, are simply aligned in conformal, non-sealing contact with each other. Those of ordinary skill in the art can readily select appropriate liquids having desired surface-wetting properties (for use in the self-aligning technique when utilizing the technique to self align surfaces comprised of materials other than oxidized PDMS) using no more than known, published surface wetting properties for various liquids on various surfaces or routine screening tests not requiring undue experimentation. In addition, while the above-described self-alignment technique has been exemplified in the context of aligning two replica molded layers of the overall microfluidic structure with respect to each other. In other embodiments, the technique can be utilized to align a replica molded layer comprising one or more levels of the microfluidic structure to the surface of a substrate, for example a silicon microchip, or the like. Utilization of the self-aligning method for aligning a layer of the microfluidic network to a substrate surface, for example a surface of a silicon microchip, may be important for applications where the microfluidic network is utilized as an on-chip sensor, detector, analyzer, etc.

Figure 7:
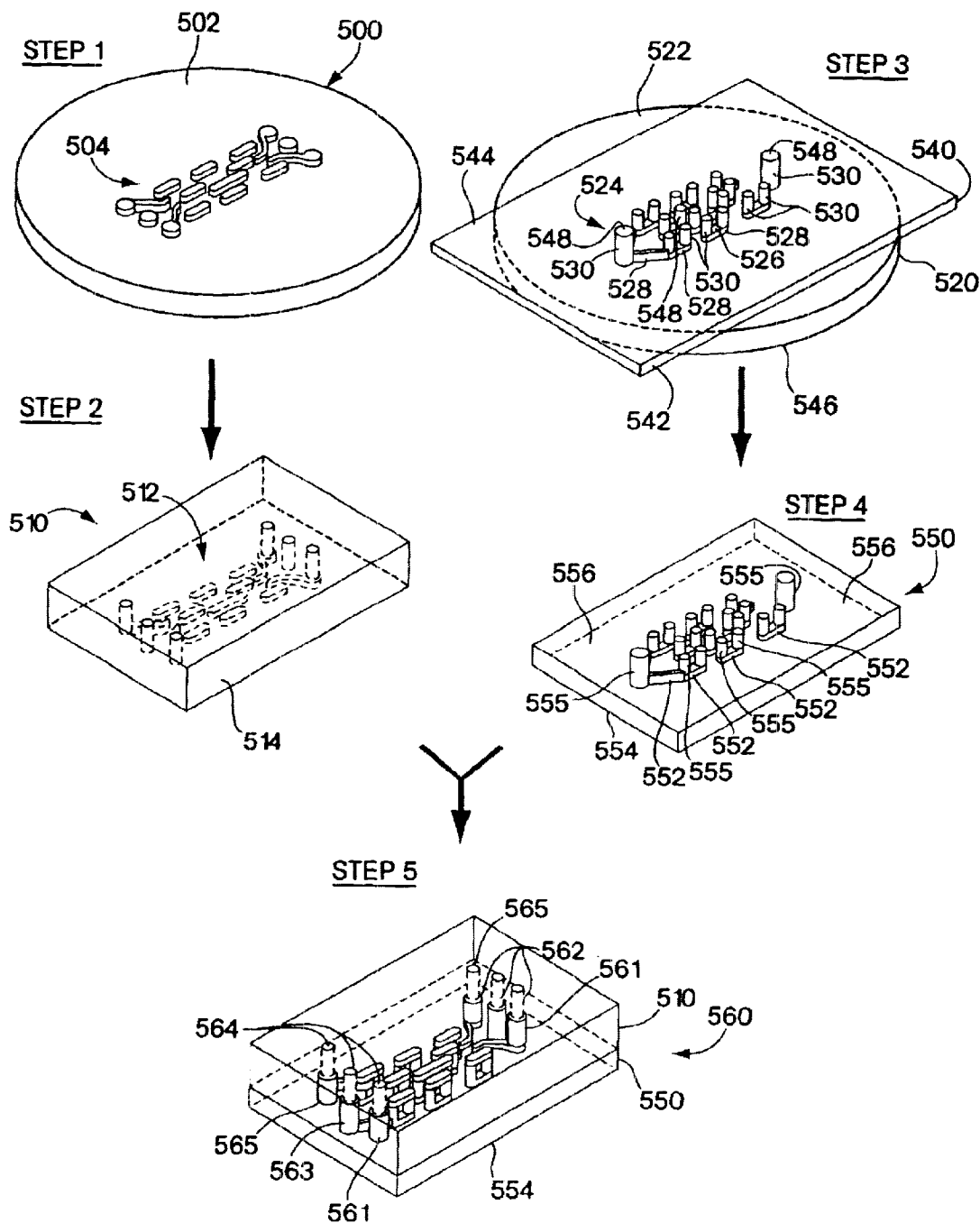
FIG. 7 is a schematic illustration of a second embodiment of a microfluidic network fabrication method according to the invention.

FIG. 7 illustrates an alternative embodiment for fabricating a microfluidic network structure according to the invention. Unlike the method previously described in the context of FIGS. 5a–5c, the fabrication method described in FIG. 7 involves the formation, by replica molding, alignment, and assembly of only two, as opposed to three, discrete layers forming the three levels of the overall microfluidic network structure.

As described above in the context of FIGS. 5a–5c, the method outlined in FIG. 7 can potentially utilize a wide variety of hardenable liquids for forming the replica molded components of the microfluidic network structure. Such hardenable liquids were described previously in the context of FIGS. 5a–5c. As previously, in preferred embodiments, the replica molded structure is formed of a polymeric material, more preferably an elastomeric material, and most preferably a transparent elastomeric material. In a particularly preferred embodiment illustrated and exemplified in FIG. 7, the replica molded structures are formed of PDMS.

In Step 1 of the method illustrated in FIG. 7, a mold master 500 having a surface 502 including a series of topological features 504 thereon protruding from the surface in positive relief is formed in a manner essentially equivalent to that described for forming mold master 300 of FIG. 5a. Topological features 504 are shaped, sized, and laid out on surface 502 in a pattern predetermined to form a desired arrangement of channels disposed in the upper, third level of the overall microfluidic network structure. Mold master 502 is then placed in the bottom of a petri dish or other container having a depth exceeding the height of the upper surfaces of topological features 504 on surface 502.

In Step 2, a hardenable liquid is added to the container containing master 500 in an amount sufficient to completely cover and submerge topological features 504. As discussed in FIG. 5a above, surface 502 of mold master 500, in preferred embodiments, is treated with a release agent, for example a silanizing agent, to permit release of the replica molded structure from the surface without undue damage or distortion of the replica molded structure. Also in Step 2, as described above in the context of FIGS. 5a–5c, the hardenable liquid, for example a PDMS prepolymer solution, is cured and solidified to form a solid molded replica 510 of surface 502 of mold master 500. Molded replica 510 is removed from surface 502 after curing as illustrated in Step 2. In the illustrated embodiment, molded replica 510 comprises a PDMS slab which can, as illustrated, be trimmed to a desired overall size and perimetric shape. Molded replica 510 includes therein, but not completely extending therethrough, a series of indentations 512 in lower surface 514 corresponding to topological features 504 of mold master 500. Indentations 512 form channels disposed within the third, upper level of the overall microfluidic network to be fabricated.

Steps 3 and 4 of the method illustrated in FIG. 7 comprise the formation of a replica molded membrane layer including therein both channels disposed in the first, lower level of the overall microfluidic network structure and connecting channels of the third, intermediate level of the overall microfluidic network structure forming fluidic connections between the channels disposed in the first, lower level and the second, upper level of the structure. The molded replica membrane layer, having two levels of features formed therein, is formed by a membrane sandwich fabrication method (Steps 3 and 4) similar to the method previously described in the context of FIGS. 5a–5c, except that mold master 520 includes a surface 522 having formed thereon a plurality of topological features 524 in positive relief protruding from surface 522, that include features, for example feature 526, that are two-level topological features, which are characterized by a first portion 528 having a first height with respect to a region of surface 522 adjacent to feature 526 and a second portion 530, which is integrally connected to the first portion, having a second height with respect to surface 522 adjacent feature 526, which second height is greater than the height of first portion 528.

The term "integrally connected," as used herein in the context of describing two-level topological features of mold masters, refers to such features having at least a first portion and a second portion, the second portion having a height or depth with respect to the surface of the mold master adjacent the feature different from the first portion, wherein the first and second portion comprise two different regions of a continuous structure or comprise two discrete structures each having at least one surface in direct contact with at least one surface of the other. By providing such two-level topological features on mold master 520, the illustrated method allows simultaneous formation and alignment of channels disposed within two levels of the overall microfluidic network structure. Thus, by forming two levels of the overall structure within a single layer in a single replica molding step, the present method eliminates the need to align two discrete layers comprising the first, lower level of the structure and the third, intermediate level of the structure with respect to each other after formation of the molded replica layers. Thus, as described below, the present method requires only a single alignment step for assembling the molded replica layers into the overall microfluidic network structure.

A variety of photolithography and micromachining methods known to those of ordinary skill in the art, which are capable of forming features on a surface having multiple heights or depths with respect to the surface, can potentially be utilized in the context of the present invention for forming the two-level topological features 526 of mold master 520. A particularly preferred embodiment for forming mold master 520 involves an inventive method for forming two-level topological features in photoresist, and is described in more detail below in the context of FIG. 8.

After formation of mold master 520, a layer of hardenable liquid, for example PDMS, is placed upon surface 522 of mold master 520 and covered with an upper mold master 540, having a lower surface 542 that is essentially flat and featureless, so that surface 542 is in conformal contact with the uppermost surfaces of the two-level topological features 526 on surface 522 of mold master 520. As previously described in the context of FIGS. 5a–5c, mold master 540 can comprise a variety of materials including, for example, an elastomeric polymer slab, for example formed of PDMS, a polymeric sheet, a flat silicon wafer, etc. In preferred embodiments, as previously discussed, it is desirable that the interfacial adhesion strength between surface 522 of mold master 520 and the hardened molded replica differ from the interfacial surface adhesion between surface 542 of mold master 540 and the hardened liquid comprising the molded replica. In the illustrated embodiment, surface 522 of mold master 520 comprises a silanized polymeric negative photoresist layer and mold master 540 comprises a Teflon™ (PTFE) sheet.

In Step 4, pressure is uniformly applied to surface 544 of upper mold master 540 and surface 546 of lower mold master 520 to enable the upper surfaces 548 of topological features 526 to make sealing contact with surface 542 of mold master 540 during the hardening and curing process forming the replica molded membrane layer. In Step 4, the hardenable liquid, for example PDMS prepolymer, is cured to form a two-level replica molded membrane 550. Two-level replica molded membrane 550 includes a plurality of first channels 552, disposed within a lower surface 554 of the membrane, comprising channels disposed within the first level of the overall microfluidic network structure, and also includes vertically oriented connecting channels 554 that completely penetrate the thickness of the membrane and interconnect lower surface 554 and upper surface 556 of the membrane, forming the connecting channels disposed within the third, intermediate level of the overall microfluidic network structure. Channels 552 comprise replica molded features corresponding to first portions 528 of topological features 526 of mold master 520 and connecting channels 555 comprise replica molded features corresponding to second portions 530 of two-level topological features 526 of mold master 520.

In the illustrated embodiment, the PDMS membrane comprising molded replica layer 550 is separated from the mold masters by first peeling PTFE sheet 540 from the upper surface 556 of the membrane and subsequently peeling the membrane from upper surface 522 of mold master 520. In other embodiments, molded replica 550 can remain in contact with upper surface 522 of mold master 520 during the subsequent, and below described, aligning and sealing steps, in order to support membrane 550 and prevent distortion or destruction of the molded features therein. It should be understood, that for more complex structures, additional replica molded membranes such as 550 can be stacked upon each other in the assembly of the microfluidic network structure to yield structures having more than three levels of interconnected microfluidic channels.

In the final step of fabrication, Step 5, replica molded slab 510 and replica molded membrane 550 are aligned with respect to each other to yield the desired microfluidic network structure, brought into conformal contact with each other, and optionally sealed together by methods previously described above in the context of FIGS. 5a–5c to yield the final microfluidic network structure 560. As previously described, the structure 560 can include inlet conduits 562 and outlet conduits 564 for each of the non-interconnected fluid flow paths disposed within the structure, or other interconnections between the flow paths within the structure and the external environment as required or desired for a particular application. In the illustrated embodiment, microfluidic network structure 560 includes three non-fluidically interconnected fluid flow paths therein. The first flow path 561 has an inlet and outlet in the foreground and is shaded light gray; the second flow path 563 has an inlet and outlet that are centrally disposed shaded in black; and the third flow path 565 has an inlet and outlet in the background and is shaded dark gray.

In addition, lowermost surface 554 of structure 560 includes therein a pattern indentations corresponding to the channels of the first, lower level of the microfluidic network structure formed within the bottom surface 554 of the replica molded membrane 550. Thus, microfluidic network structure 560 is useful for embodiments wherein the microfluidic network structure is utilized as a surface patterning stamp for depositing materials onto a material surface in a pattern corresponding to the channels disposed within surface 554, or otherwise creating a patterned surface with a pattern corresponding to the pattern of the channels disposed within surface 554. In alternative embodiments, surface 554 can be placed in conformal contact with, and optionally sealed to, a solid PDMS slab, or other substrate or surface, to form an enclosed microfluidic network structure, as described previously in the context of FIGS. 5a–5c.

Figure 8:
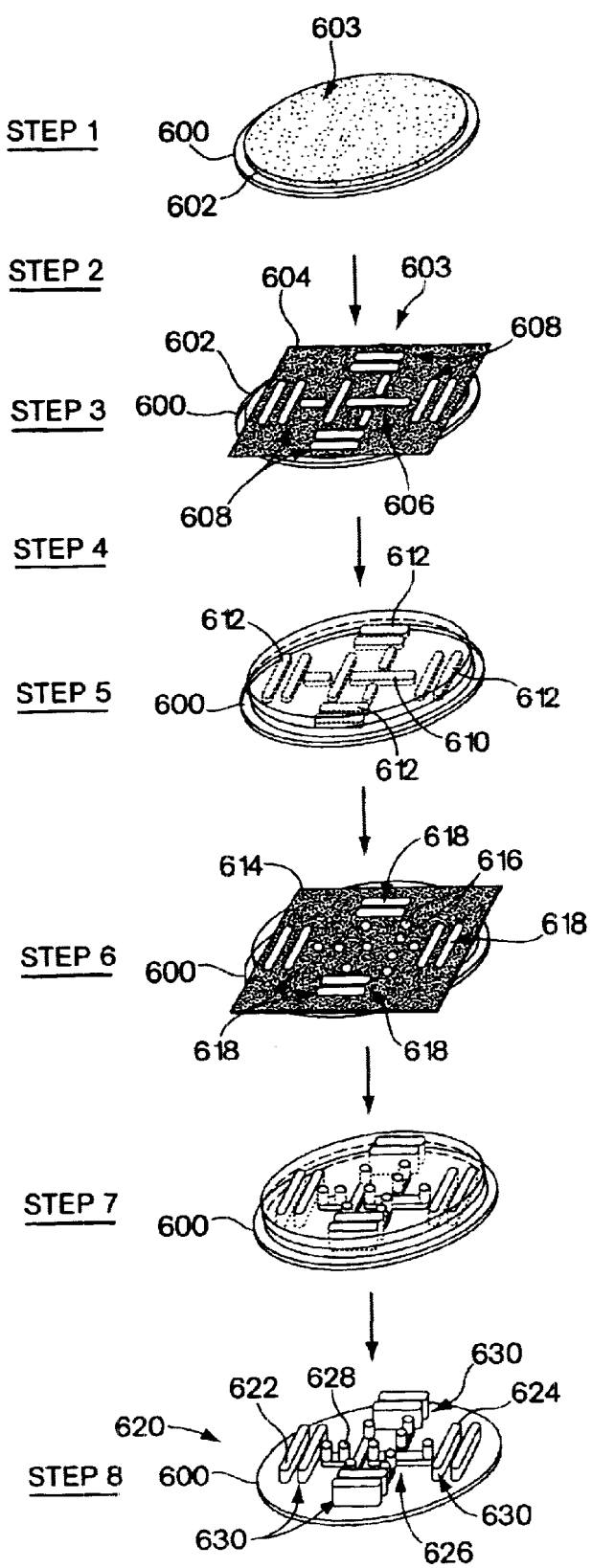
FIG. 8 is a schematic illustration of a method for forming a two-level topological feature on a surface of the substrate by photolithography provided according to the invention.

FIG. 8 illustrates a preferred method for preparing mold masters that have a surface including thereon one or more two-level topological features. While the illustrated method is useful for forming two-level topological features in layers of either negative or positive photoresist materials, in the embodiment illustrated, a negative photoresist material (e.g., SU8-50) is utilized as an example. In addition, while, in the illustrated embodiment, two-level topological features comprising positive, high-relief features protruding from the surface of the mold master are fabricated, it should be understood that the method is also well suited to produce two-level topological features comprising negative, low-relief features characterized by indentations, grooves, or channels within the surface of the mold master. Any variations in the below described technique for producing two-level positive, high-relief features in negative photoresist that are required in order to produce two-level features in positive photoresist and/or to produce two-level features comprising negative, low-relief features involve only simple extensions of the below-described method that would be apparent to those of ordinary skill in the art.

In Step 1 of the method illustrated in FIG. 8, a silicon wafer 600, or other suitable substrate, is coated with a layer of photoresist 602, by a conventional spin-coating technique or other suitable coating technique known to those of ordinary skill in the art. Layer 602 is spin-coated to a depth corresponding to the desired depth of the deepest feature to be formed on the first level of the mold master (e.g. a depth corresponding to the deepest channel to be disposed in the level of the microfluidic channel structure to be replica molded by the first level of the mold master. The thickness of layer 602 will typically range from about 20 $\mu$m to about 500 $\mu$m, and can, in some embodiments, be as thick as about 1 mm.

In Step 2, the photoresist is "soft baked" by being exposed to an elevated temperature for a short period of time to drive off solvent used in the spin-coating process For example, for SU8-50 negative photoresist, the coated substrate is exposed to a temperature of about 95–105° C. for a period of several minutes. In Step 3, a first photomask 604 including thereon a pattern 606 corresponding to features 626 of the first level of the mold master is placed in contact with negative photoresist layer 602. As would be apparent to those of ordinary skill in the art, a wide variety of photomasks can be utilized according to the present inventive method; however, in a preferred embodiment illustrated, photomask 604 comprises a high resolution transparency film having a pattern printed thereon. Designs for the channel system printed upon the high resolution transparency are preferably generated with a CAD computer program. In the illustrated embodiment, a high-resolution (e.g., 3000–5000 dpi) transparency, which acts as photomask 604, is produced by a commercial printer from the CAD program design file. In the illustrated embodiment, essentially the entirety of photomask 604 is rendered opaque to the radiation used to expose the photoresist by a layer of toner, and the fluidic channel-forming features to be formed on the surface of negative photoresist 602 correspond to transparent regions 606 of the photomask surface.

In addition to regions 606 corresponding to features in the mold master for forming fluidic channels within the molded replica structure formed with the mold master, photomask 604 also includes peripheral transparent regions 608, which correspond to topological features for forming alignment tracks useful for aligning the mold masters with respect to each other in certain methods for forming microfluidic structures as described in more detail below in FIGS. 9a and 9b.

In Step 4, upper surface 603 of photoresist layer 602 is exposed to radiation, for example ultraviolet (UV) radiation of a frequency and intensity selected to cross-link exposed areas of the negative photoresist, through the transparent regions of the printed pattern of photomask 604. In Step 5, after exposure to cross-linking radiation, the first photomask 604 is removed from the surface, the photoresist is hard-baked (e.g. at about 95–105° C. for several minutes) and a second layer of photoresist is spin-coated on top of surface 603 of photoresist 602. The second layer of photoresist is spin-coated to a thickness sufficient for forming features in the mold master corresponding to the connecting channels disposed within the third, intermediate level of the replica molded microfluidic network structure formed with the mold master. Typically, the thickness of the second level of photoresist will range from about 20 µm to about 1 mm. Wafer 600, now containing a first, exposed layer of photoresist and a second layer of unexposed photoresist can then be subject to another soft-baked procedure to drive off solvent from the unexposed layer of photoresist, similarly as described in Step 2 above.

As illustrated in Step 5 of FIG. 8, regions of the first layer of photoresist that were exposed to the radiation (e.g., regions 610 and 612) typically exhibit a change in the degree of transparency and/or refractive index of the photoresist, thus rendering them visible through the upper layer of newly spin-cast, unexposed photoresist. This visibility allows a second photomask to be easily aligned with respect to the first exposed pattern by using a standard photomask aligner. In other embodiments, especially where the exposed pattern may not be visually apparent, visible alignment features or elements can be included on the surface of wafer 600 to enable alignment of the second photomask to achieve a desired two-level pattern, as would be apparent to those of ordinary skill in the art.

In Step 6, a second photomask 614 including thereon printed patterns 616, corresponding the second level portions of the two-level topological features of the mold master, which form the connecting channels in the intermediate level of the replica molded microfluidic network structure formed with the mold master, and 618, corresponding to a second level of the optional alignment tracks. It should be understood, that while, in the illustrated embodiment, features 606 corresponding to topological features for forming channels disposed in the first level of the microfluidic network structure comprise linear features, in other embodiments, features 606 can be non-linear, thus forming curved topological features resulting in non-linear, curved channels within the first level of the microfluidic structure. Similarly, any of the previously described structures and methods for forming channels disposed within a particular level of microfluidic network structure can include channels that are non-linear and curved within the plane or curved surface defining the level of the microfluidic network structure in which the channels are disposed in addition to, or instead of, the straight channels previously illustrated.

Printed pattern 616, creating topological features for forming channels within the microfluidic network structure can also, in some embodiments, include features parallel and contiguous with regions 610 formed within the first layer of photoresist and corresponding to printed pattern 606, such that some of the topological features produced on the surface of the mold master by the illustrated method include features that form channels having a longitudinal axis parallel to the first level of the replica molded microfluidic network structure formed with the mold master, and which have an overall depth within the replica molded microfluidic network structure formed with the mold master, which is equal to the combined depth of the first level and the third, intermediate level of the structure (i.e., for forming replica molded microfluidic network structures having deep channels that are disposed within both the first level and the third, intermediate level of the microfluidic network structure).

Photomask 614 is aligned in Step 6 with respect to exposed pattern 610 and the second, unexposed layer of photoresist is exposed, in Step 7, to the cross-linking radiation through photomask 614. Following exposure, mask 614 is removed from the top layer of photoresist, and the photoresist is hard-baked as described above. If desired, the above-mentioned steps can be repeated with additional layers of photoresist and additional photomasks to produce more than two levels of topological features on the surface of wafer 600. After the desired number of layers of photoresist have been coated onto wafer 600 and exposed to cross-linking radiation as described above, the relief pattern is developed in Step 8 by exposing the photoresist to a developing agent that dissolves and removes non-crosslinked photoresist material leaving behind a mold master 620 having a surface 622 including thereon a pattern of two-level high relief features 624 having a first portion 626 with a first height above surface 622 and a second portion 628 having a second height above surface 622, which is greater than height 626. First portion 626 of the topological features forms the channels disposed within the first level of the replica molded microfluidic network structure formed with mold master 620, and second portion 628 of the topological features forms the connecting channels traversing the third, intermediate level of a microfluidic network structure replica molded using mold master 620.

Also formed on surface 622 of mold master 620 by the above-outlined process are alignment tracks 630 having a height corresponding to the height of the second portion 628 of topological features 624. While, in the illustrated embodiment, the second layer of photoresist was spin-coated onto a first layer of exposed photoresist before developing the first layer, in an alternative embodiment, the first layer of photoresist can be developed before spin-coating the second layer of photoresist if desired. Solvents useful for developing the unexposed portions of the photoresist are selected based on the particular photoresist material employed. Such developing agents are well known to those of ordinary skill in the art and are typically specified by the commercial manufacturers of many of the photoresists useful for performing the methods of the invention. For example, for the illustrated embodiment utilizing SU8-50 negative photoresist, uncross-linked photoresist can be removed during development by exposing the photoresist to propylene glycol methyl ether acetate. Two-level old master 620, subsequent to formation as described above, is preferably coated with a release agent, for example by silanizing the surface, in order to facilitate removal of a molded replica from the surface of the mold master.

Figure 9A:
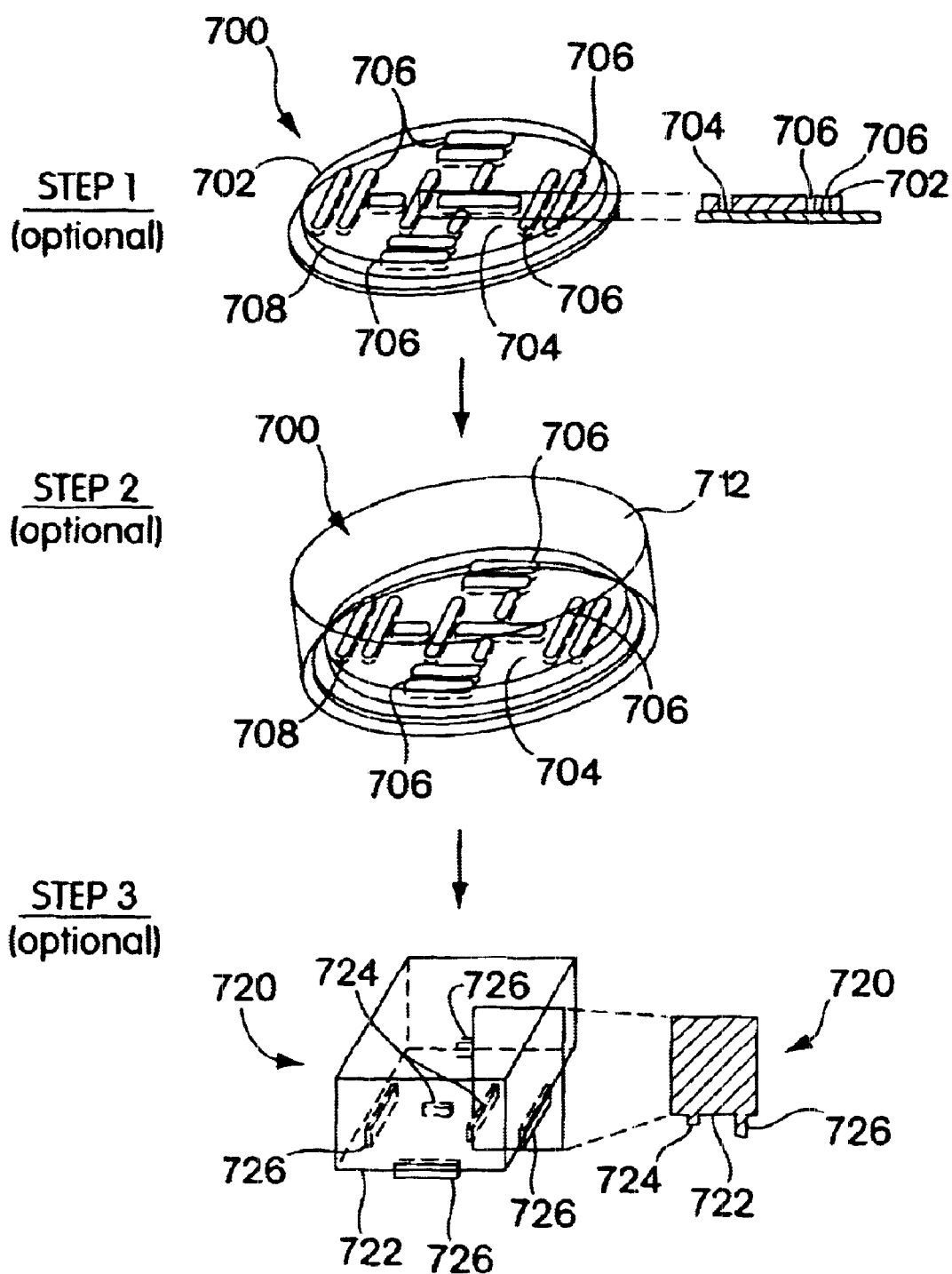
FIGS. 9a–9b are schematic illustrations of a third embodiment for forming a microfluidic network structure according to the invention.
Figure 9B:
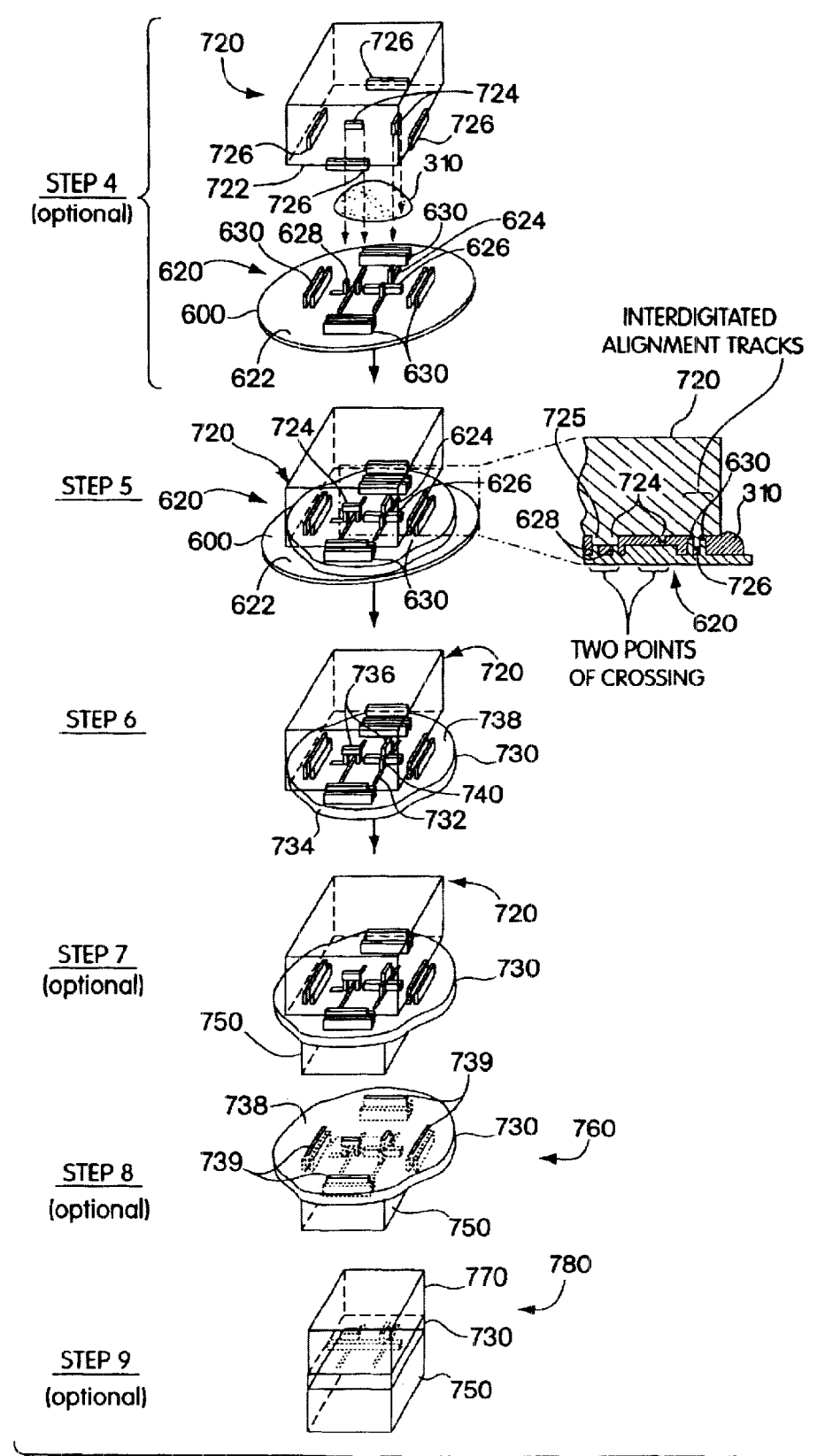

FIGS. 9a and 9b illustrate the steps of a third embodiment of the method according to the invention for fabricating a three-dimensional microfluidic network structure. The method illustrated in FIGS. 9a and 9b comprises a membrane sandwich technique similar to that previously described in Steps 3 and 4 of the method illustrated in FIG. 7, except that instead of forming a replica molded membrane layer between a bottom master including two-level topological features and a top mold master having an essentially flat, planar surface, as was illustrated in the method of FIG. 7, in the method according to FIGS. 9a and 9b, a replica molded membrane layer is formed between two mold masters, both including topological features thereon and at least one including at least one two-level topological feature thereon, thus yielding a replica molded membrane including therein a microfluidic network structure containing all three of the above-discussed levels. In some embodiments, both the upper and lower mold masters utilized for forming the three-level replica molded membrane layer according to the embodiment of FIGS. 9a and 9b can comprise mold masters, for example similar to mold masters 500 and 520 shown in FIG. 7. However, as previously discussed, it is desirable for at least one of the mold masters to be formed of an elastomeric material to improve sealing contact between portions of the surfaces of the mold masters that are in contact during the replica molding process so as to prevent undesirable leakage of hardenable liquid into such regions of contact. Therefore, in preferred embodiments, the upper mold master and/or lower mold master are formed from an elastomeric material having a surface with topological features thereon.

In some particularly preferred embodiments, elastomeric mold masters are formed using a replica molding procedure, similar to that used to form the various layers of the microfluidic structure, to form topological features on the elastomeric mold master that are formed during replica molding from topological features on a pre-master prepared by photolithography or micromachining. The method illustrated in FIGS. 9a and 9b correspond to such a preferred embodiment. In the illustrated embodiment, the top mold master, as well as the replica molded membrane layer, are formed from an elastomeric material comprising PDMS. As referred to and discussed extensively above, PDMS, while being preferred for forming many of the structures and mold masters according to the invention, comprises only one example of a material formable from a hardenable liquid useful for forming the mold masters and microfluidic networks according to the invention. A wide variety of alternative materials and hardenable liquids have been previously discussed in the context of the methods illustrated in FIGS. 5 and 7, and such materials, or other materials apparent to those of ordinary skill in the art, can be substituted for PDMS in the method illustrated in FIGS. 9a and 9b below.

FIG. 9a illustrates one preferred method for forming an elastomeric top mold master for use in forming a three-level replica molded membrane layer. In Step 1, a pre-master mold is fabricated by forming topological features on a surface of a substrate 700, for example as previously illustrated in the context of FIG. 8. Since, in the illustrated embodiment, it is desired that the topological features formed in the replica molded top mold master comprise positive, high-level relief features protruding from the surface of the mold master, the topological features formed on surface 702 of substrate 700 comprise negative, low-level relief features characterized by grooves or channels 704, 706 seen more clearly in the cross-sectional view. In the illustrated embodiment, pre-master mold 700 is fabricated using a two-level photolithography technique similar to that described in FIG. 8. Topological features 706 have a greater depth than topological features 704 and essentially traverse the entire thickness of photoresist layer 708. In the illustrated embodiment, topological features 706 correspond to and form topological features in the replica molded elastomeric mold master which are alignment tracks, whose function is explained in more detail below. Topological features 704 correspond to and form topological features in the replica molded mold master which are responsible for forming channels ultimately disposed in the second, upper level of the replica molded three-level membrane layer. It should be understood that in alternative embodiments, one or more of topological features 704 can comprise two-level topological features having a first portion with a first depth with respect to surface 702 and a second portion with a second, greater depth (e.g. corresponding to the depth of topological features 706) with respect to surface 702. For such embodiments, a replica molded top mold master would include two-level topological features in positive relief for forming channels disposed in the second, upper level of the replica molded membrane as well as connecting channels traversing the membrane. In such embodiments, the lower mold master can include channel-forming topological features having a single, uniform height or can include channel-forming topological features that are also two-level topological features.

In Step 2, pre-master mold 700 is placed into the bottom of container 712. The container is then filled with a hardenable liquid, such as PDMS prepolymer, to a level at least covering upper surface 702 of pre-master mold 700. Subsequently, the hardenable liquid is cured or solidified, as previously discussed, and, in Step 3, is removed from the pre-master mold, optionally trimmed, and treated with a release agent, for example by silanization or oxidation followed by silanization. The resulting structure 720 comprises a replica molded mold master including a surface 722 having disposed thereon topological features 724 at a first height with respect to surface 722 and corresponding to topological features 704 of pre-master 700, and topological features 726 having a second, greater height with respect to surface 722 and corresponding to topological features 706 on pre-master 700. Topological features 724 comprise channel-forming features and topological features 726 comprise alignment tracks.

FIG. 9b illustrates steps for forming the replica molded three-level membrane layer with the upper mold master 720 produced according to the steps outlined in FIG. 9a above and a lower mold master 620 produced according to the method outlined previously in FIG. 8. In Step 4, a quantity of hardenable liquid 310, for example PDMS prepolymer, is placed in contact with upper surface 622 of lower mold master 620 in an amount sufficient to form a layer having a thickness at least equal to the height of topological features 628 and 630. Upper mold master 720 is then brought into contact with lower mold master 620 in Step 5 and is manually manipulated until topological features 726 comprising alignment tracks in the upper mold master mate and interdigitate with topological features 630 comprising alignment tracks in the lower mold master. Upon mating and interdigitating of alignment tracks 726 and 630, the alignment and relative position of channel-forming topological features 724 of the upper mold master and channel-forming topological features 624 of the lower mold master is such that they are properly positioned and aligned with respect to each other to form the desired three-dimensional microfluidic network channel structure within the replica molded membrane layer. The interface between the upper mold master 720 and lower mold master 620 during the replica molding process in Step 5 is seen more clearly in the cross-sectional view. The cross-sectional view illustrates that, upon proper alignment, alignment tracks 726 of upper mold master 720 mate and interdigitate with alignment tracks 630 in lower mold master 620. In addition, the cross-sectional view also clearly illustrates the conformal, sealing contact made between channel-forming feature 725 in upper mold master 720 and the upper surface of second portions 628 of the topological features on the surface of the lower mold master.

In Step 6, hardenable liquid 310, for example PDMS prepolymer, is cured, as previously described and upper mold master 720 is peeled away from lower mold master 620. In the illustrated embodiment, where upper mold master 720 comprises silanized PDMS, lower mold master 620 has an upper surface 622 comprising polymeric photoresist and hardenable liquid 310 comprises PDMS prepolymer, the replica molded PDMS membrane layer 730 formed upon curing will adhere more strongly to surface 722 of upper mold master 720 than to surface 622 of lower mold master 620 and, upon peeling away of upper mold master 720, will remain adhered to and supported by upper mold master 720, thus preventing damage to the membrane.

Replica molded membrane layer 730 includes therein channels 732 disposed within lower surface 734 of membrane 730, formed by first portion 626 of topological features 624 of lower mold master 620; upper channels 736 disposed within upper surface 738 of the membrane, formed by topological features 724 of the upper mold master; and connecting channels 740 traversing the membrane and interconnecting surface 734 and surface 738, which interconnecting channels are formed by second portions 628 of two-level topological features 624 of lower mold master 620. Thus, in the presently described method, a single replica molded layer is formed that includes therein all three levels required to form a three-dimensional microfluidic network structures according to the invention. In addition, because of the provision of alignment tracks 726 and 630, the entire three-dimensional network structure was formed without the need for performing an alignment of features or channels requiring the use of a microscope or micromanipulator. Because the present method does not require visual alignment of features or channels, it can be especially useful for forming microfluidic membrane structures from materials that are opaque to visible light.

Replica molded polymeric membrane 730 can be removed from upper mold master 720 and can be utilized as a stand-alone structure or can be stacked with other such structures to form more complex networks. Optionally, and as shown in Step 7, before removal from upper mold master 720, lower surface 734 of membrane 730 can be brought into conformal contact with a lower substrate layer 750, for example, a flat piece of PDMS, silicon wafer, microchip, or other substrate, and can optionally be sealed thereto as previously described. Substrate layers, instead of having flat smooth surfaces as illustrated, can, in other embodiments, include topological features thereon that are matable with topological features on the surface of the replica molded membrane, for example, alignment tracks 739, so that, upon interdigitation of the matable topological features on the substrate layer and one or more topological features on the surface of the replica molded membrane, the membrane is aligned and oriented in a desired configuration with respect to the substrate. After contacting the membrane with the substrate layer and, optionally, essentially irreversibly sealing the membrane to the substrate layer, upper mold master 720 can then be removed from upper surface 738 of membrane 730 as illustrated in step 8. The resulting microfluidic network structure 760 can be utilized as shown or after trimming away the regions of the membrane including alignment tracks 739. Structure 760 is useful, for example, as a microfluidic membrane stamp for patterning a material surface, the stamping surface comprising upper surface 738 of membrane 730, which has channels 736 disposed therein. Structure 760 is also useful for embodiments wherein the microfluidic network structure is utilized as a mold in which to form three-dimensional networks of materials having a structure corresponding to the channel structure in membrane 730, as described in more detail below.

For embodiments where it is desired to provide an enclosed series of microfluidic channels, upper surface 738 of membrane 730 is subsequently placed in conformal contact with and, optionally sealed to, an upper substrate layer 770. Upper substrate layer 770 can comprise a slab of PDMS or other substrate layer desirable for a particular application, as previously discussed. Also, as previously discussed, inlet and outlet conduits can be formed within either or both of substrate layers 770 and 750 in order to interconnect the fluid flow paths of the microfluidic channel structure to the external environment.

Figure 10:
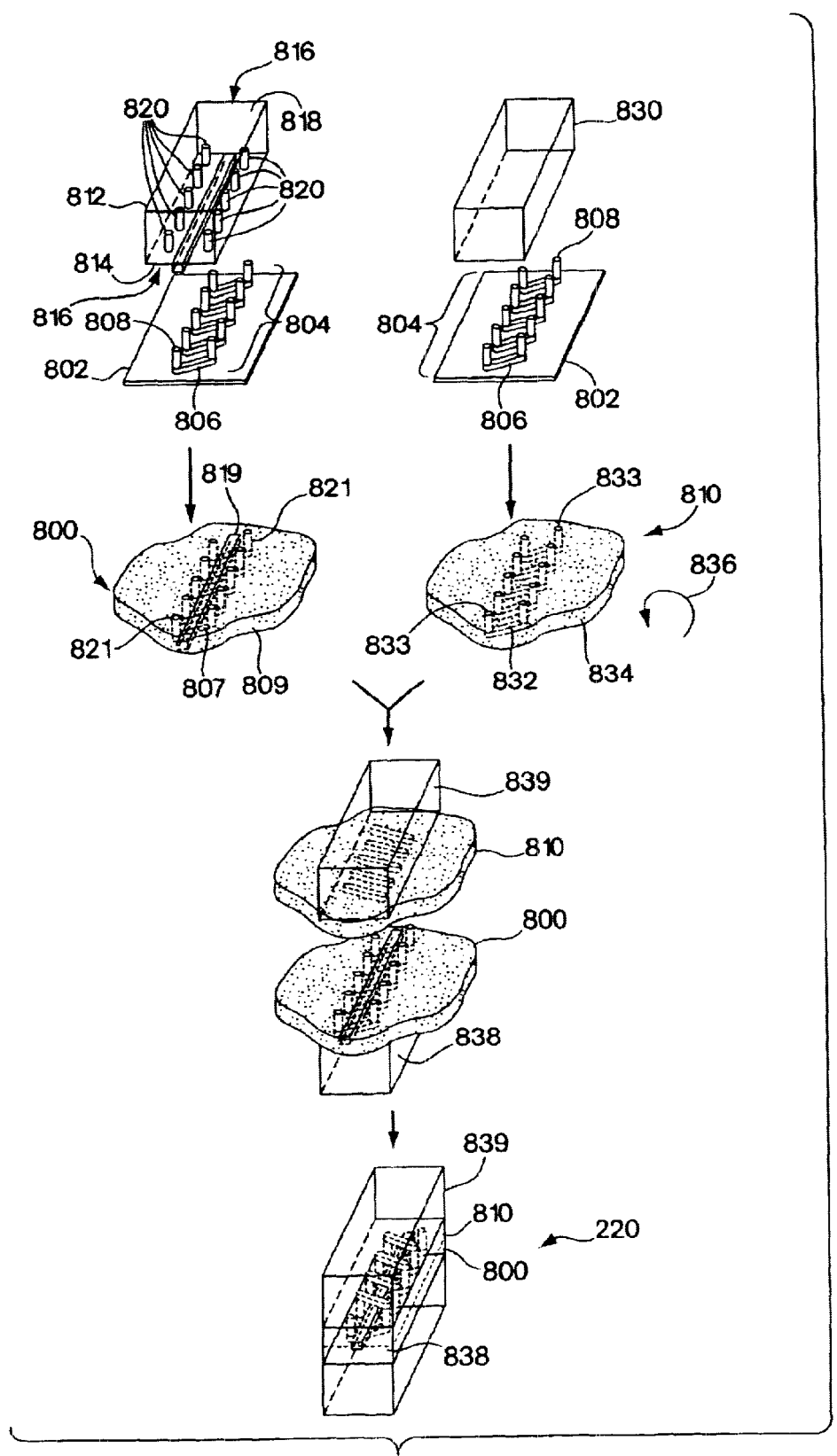
FIG. 10 is a schematic illustration of a method for forming a five-level microfluidic network structure including a straight channel surrounded by a coiled series of interconnected channels.

FIG. 10 illustrates a method for forming the five-level microfluidic network structure, shown previously in FIG. 4a, comprising a coiled network of interconnected channels forming a first fluid flow path surrounding a straight channel forming a second fluid flow path. The method in FIG. 10 is based upon the methods previously described in FIGS. 8, 9a, and 9b discussed above. In the method shown in FIG. 10, two separate molded replica membrane layers are formed, which are subsequently aligned with respect to each other and sealed together to form the final, overall, five-level coiled network structure 220. The first molded replica membrane layer 800 comprises three levels of the overall structure and a second molded replica membrane layer 810 comprises the remaining two levels of the overall microfluidic network structure. Molded replica layer 800 comprising three levels is formed by the membrane sandwich method previously discussed in the context of FIG. 9b and utilizing a lower mold master 802 having formed thereon a plurality of two-level topological features 804 having first portions 806, forming channels 807 disposed within the first, lowermost level of the overall microfluidic network structure, and second portions 808 forming connecting channels traversing the level adjacent to and positioned immediately above the lowermost level of the microfluidic network structure upon replica molding.

Upper mold master 812 is preferably a replica molded elastomeric material (e.g. like mold master 720) and includes a bottom surface 814 having a plurality of single-level topological features 816 protruding therefrom including a centrally disposed feature 818, forming the straight channel 819 disposed on the second, upper level of membrane layer 800, and a plurality of features 820, aligned with second portions 808 of topological features 804 of lower mold master 802, forming a continuation of connecting channels 821 through the second, upper level of replica molded layer 800 upon replica molding. Molded replica layer 810, comprising the two uppermost levels of the overall structure, is formed by the same membrane sandwich method utilizing lower mold master 802 and an upper mold master 830, which comprises a flat slab of preferably elastomeric material. Two-level topological features 804, having first portions 806 and second portions 808, form a series of channels 832 disposed within lower surface 834 of molded replica layer 810 and form connecting channels 833 traversing the thickness of molded replica layer 810, upon replica molding of layer 810.

In order to complete the assembly and form the overall coiled microfluidic network structure 220, molded replica layer 810 is rotated 180° in the direction of arrow 836, stacked on top of molded replica layer 800, aligned so that the replica molded channels are registered to form the desired coiled channel network structure, brought into conformal contact with, and optionally sealed to molded replica layer 800. Optionally, surface 834 of molded replica layer 810 and/or surface 809 of molded replica layer 800 can be brought into conformal contact with, and optionally sealed to, a substrate layer (e.g., 838, 839) prior to or subsequent to stacking, aligning, and, optionally, sealing layers 800 and 810 to each other. If desired, excess material comprising layers 800 and 810 can be trimmed from the structure as illustrated in the final step of FIG. 10. The resulting structure 220 includes the coiled, two fluid flow path microfluidic network previously described in detail in the context of FIG. 4a above.

In addition to being useful as fluid flow directing networks for applications requiring fluid management in very small scale devices, for example, in micro total analysis systems (μTAS), the microfluidic network structures provided according to the invention are also useful for a variety of other uses. For example, microfluidic channel systems fabricated according to the invention can be used to fabricate a variety of microstructures having three-dimensional structures corresponding to a three-dimensional network of channels within a microfluidic network structure. Such microstructures can be formed by filling the channel network of the microfluidic systems with a hardenable liquid, solidifying the hardenable liquid within the network channels, and, optionally, removing the surrounding microfluidic network structure to yield a free-standing microstructure comprised of the solidified hardenable liquid. The hardenable liquid utilized for form microstructures that are replica molded within the inventive microfluidic network systems can comprise essentially any of the hardenable liquids described above as being useful for forming the microfluidic network structures themselves. The hardenable liquids chosen to form the replica molded microstructures should be chemically compatible with the microfluidic network structure and, for embodiments where it is desired to selectively remove a surrounding microfluidic network structure, should be resistant, once hardened, to whatever treatment is required to dissolve or otherwise remove the surrounding microfluidic network structure. In one particular illustrative example, a microfluidic network structure produced according to the invention and composed of PDMS can be filled with an epoxy prepolymer, so that the epoxy prepolymer essentially completely fills the microfluidic channel structure of the microfluidic network. The epoxy prepolymer can then be cured, for example by exposure to ultraviolet light through the surrounding PDMS microfluidic channel structure, in order to cure the epoxy prepolymer and form a solid microstructure within the channels. The surrounding PDMS microfluidic network can then be dissolved, for example with tetrabutylammonium fluoride (1.0 M in tetrahydrofuran) leaving behind a free-standing microstructure, comprised of epoxy polymer, having a three-dimensional structure corresponding to the three-dimensional network of channels in the PDMS microfluidic channel structure.

In another illustrative application for certain microfluidic channel structures provided by the invention, the microfluidic channel structure is used as a three-dimensional microfluidic applicator or "stamp" for forming a pattern on a material surface corresponding to a pattern of channels disposed in one level of the microfluidic network structure. The "stamping surface" of such structures includes disposed therein a series of channels forming indentations, which channels can deliver material to a substrate surface in contact with the "stamping surface" in order to form a pattern thereon corresponding to the pattern of channels in the stamping surface. Examples of structures discussed previously having "stamping surfaces" are microfluidic channel structure 560 illustrated in FIG. 7 having a stamping surface 554, and microfluidic channel structure 760 illustrated in FIG. 9b having a stamping surface 738.

The method for patterning a material surface with a microfluidic network structure provided according to the invention comprises contacting a stamping surface of the microfluidic network structure with a material surface to be stamped, and, while maintaining the stamping surface in contact with the material surface being stamped, at least partially filing one or more flow paths of the microfluidic channel structure with a fluid so that at least a portion of the fluid contacts the material surface. Subsequently, if desired, the stamping surface can be removed from the material surface, yielding a pattern on the material surface, according to the pattern of channels disposed within the stamping surface, formed by contact of the material surface with the fluid.

Figure 11:
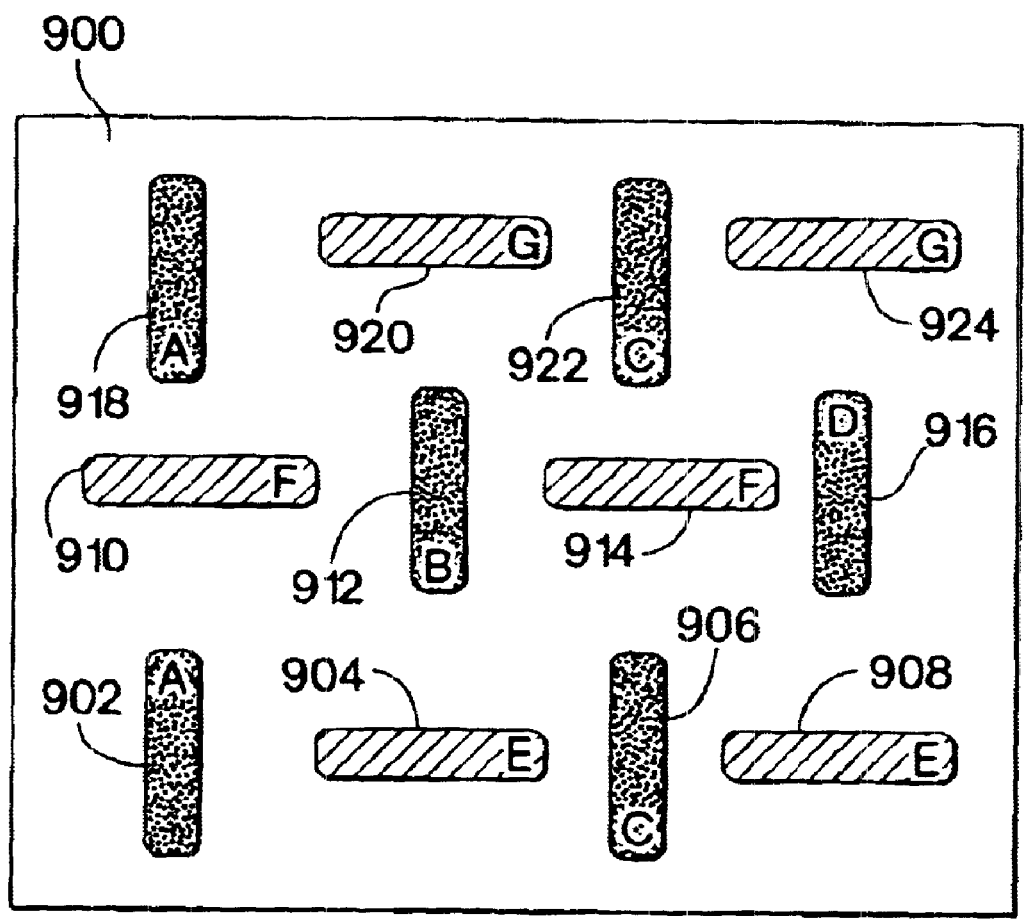
FIG. 11 is a schematic illustration of a pattern on a material surface formed with a microfluidic stamp provided according to the invention.

One example of such a stamped pattern is illustrated in FIG. 11. The microfluidic stamp utilized for forming the pattern in FIG. 11 was previously illustrated in FIG. 1a. In forming the pattern in FIG. 11, microfluidic network 100 (FIG. 1a) is formed so that lower surface 134 is configured as a stamping surface, with the channels disposed therein comprising indentations within the surface exposed to the external environment. For embodiments wherein the microfluidic network structures are utilized as stamps/applicators, it is especially preferred that the microfluidic network structures be formed of an elastomeric material, so that the stamping surface of the stamp is able to make a fluid-tight conformal seal with a wide variety of shapes and textures of material surfaces.

The microfluidic stamps provided according to the invention can be utilized to form patterns on material surfaces comprised of an extremely wide variety of materials, as would be apparent to those of ordinary skill in the art. The structures provided according to the invention, when used as stamps, can be utilized, for example: to form patterned self-assembled monolayers (SAMs) on material surfaces; to form patterns of inorganic materials on surfaces; to form patterns of organic and/or biological materials on surfaces; to form patterns on surfaces via contacting the surfaces with a material that chemically reacts with and/or degrades/etches the material surface; etc. Essentially any material able to be printed via conventional microcontact printing techniques can be patterned onto a surface using the inventive microfluidic stamping structures provided by the invention. A variety of such materials and applications is described in detail in U.S. Pat. Nos. 5,512,131; 5,620,850; 5,776,748; 5,900,160; 5,951,881; and 5,976,826, each of which is incorporated herein by reference.

The microfluidic stamping structures provided according to the invention have several advantages over traditional two-dimensional microfluidic stamps. For example, the microfluidic stamping structures provided according to the invention have the ability to simultaneously form a plurality of patterns onto a material surface, each of which patterns is comprised of a different material or "ink". In general, the number of different patterns and materials which can be patterned onto a material surface simultaneously by the stamps provided according to the invention is equal to the number of independent, non-fluidically interconnected fluid flow paths disposed within the microfluidic stamping structure.

In order to form multiple patterns with different "inks" utilizing traditional two-dimensional microcontact printing stamps, individual stamps each having a separate pattern thereon must be utilized, with each stamp being inked with a different fluid, and with each pattern being carefully overlaid upon the previous pattern and aligned thereto. By utilizing the three-dimensional microfluidic channel structures provided according to the invention, the inventive stamps are able to form, simultaneously, essentially any desired number of arbitrarily complex patterns on a material surface using a single stamp in a single stamping step.

For example, referring again to FIG. 11, the microfluidic channel system of FIG. 1a having a stamping surface 134 is able to simultaneously form an overall pattern on material surface 900 corresponding to seven discrete subpatterns (A–G), each subpattern corresponding to channels disposed within stamping surface 134 of one of the seven fluid flow paths (102, 104, 106, 108, 110, 112, 114) of the microfluidic channel system shown in FIG. 1a. As illustrated, each of subpatterns A–G includes discrete pattern features (902, 904, 906, 908, 910, 912, 914, 916, 918, 920, 922, and 924) which are non-continuous, and which are non-intersecting with each other. In general, the micrbfluidic stamps provided according to the invention are capable of forming patterns comprised of discrete regions, wherein the discrete regions are non-continuous with each other, and wherein discrete regions corresponding to and formed by channels within the stamping surface of the structure corresponding to two different non-fluidically interconnected fluid flow paths are non-intersecting with each other.

In the illustrated pattern shown in FIG. 11, it is possible to pattern up to seven different materials ("inks") onto material surface 900 simultaneously using microfluidic stamp 100 by filling each of the separate flow paths of the microfluidic network with a different fluid after contacting stamping surface 134 with material surface 900. For example, patterned regions labeled "A" in FIG. 11 can comprise a first patterned material, regions labeled "B" can comprise a second patterned material, regions labeled "C" can comprise a third patterned material, regions labeled "D" can comprise a fourth patterned material, regions labeled "E" can comprise a fifth patterned material, regions labeled "F" can comprise a sixth patterned material, and regions labeled "G" can comprise a seventh patterned material. The overall pattern that results on material surface 900 corresponds to each of the seven individual subpatterns (A–G) formed by contact of material surface 900 with the particular fluids contained within each of the individual flow paths forming subpatterns A–G.

In some embodiments, regions of stamping surfaces disposed between channel indentations that make conformal contact with the material surface being stamped can also, if desired, be coated with another material or, "ink". In such embodiments, in addition to forming patterns corresponding to the channel structures in the stamping surface as described above, the regions surrounding, contiguous with, and separating the patterns formed by the channel structures ("printing regions") can also contain a deposited material, carried by the printing regions, which material is printed on the material surface upon conformal contact of the "printing regions" of the stamping surface with the material surface. The above technique enables an operator to essentially simultaneously perform a conventional microcontact printing step and a step of depositing material in a predetermined pattern on the material surface via the channels disposed in the stamping surface of the microfluidic stamp.

Because it is possible to create arbitrarily complex patterns comprising a large number of patterned regions containing different patterned materials, the stamps provided according to the invention potentially have an extremely wide range of use for a wide variety of applications. For example, in one preferred application, the inventive stamps can be utilized to pattern cells and/or proteins onto surfaces. For example, proteins can be selectively patterned onto a surface which are adhesive to cells, non-adhesive to cells, or selectively adhesive to certain cells while non-adhesive to other cells. By forming patterns with such proteins, complex patterns of one cell type or a variety of cell types can be selectively patterned onto surfaces for various applications, for example, for forming biosensors or performing drug screening tests. With the microfluidic stamps provided according to the invention it is possible, in principle, to pattern a large number, for example in excess of 200 or 300, different cell types, each separated from each other and arranged in a patterned array format. Such patterning can be accomplished, according to the invention, by, for example, selectively patterning proteins onto a surface adherent to particular cell types followed by contact of the patterned material surface with one or more cell suspensions, or by selectively patterning a plurality of different cell types onto a surface directly using a microfluidic stamp and filling particular fluid flow paths within the stamp with suspensions containing a discrete cell type or mixture of cell types desired to be patterned onto the surface. The ability to form patterns comprising arrays of regions, with each region including a particular cell type or mixture of cell types, can enable the creation of material surfaces for use in biosensors or drug screening devices having cells patterned thereon that can be easily and readily identified by their spatial locations on the surface.

Proteins can also be deposited, using the inventive microfluidic stamps, that tend to prevent or inhibit cell adhesion to a material surface. Such proteins are well known to those of ordinary skill in the art and include for example bovine serum albumin (BSA). In addition, proteins can be patterned according to the invention that tend to promote cell adhesion to the material surface. Such proteins include, for example, fibrinogen, collagen, laminin, integrins, antibodies, antigens, cell receptor proteins, cell receptor antagonists, and mixtures of the above.

As described above, the microfluidic stamping structures provided according to the invention, can be utilized to deposit a patterned layer of cells on a material surface. Cells which can be patterned on material surface comprise essentially the entire range of biological cells including, but not limited to, bacterial cells, algae, ameba, fungal cells, cells from multi-cellular plants, and cells from multi-cellular animals. In some preferred embodiments, the cells comprise animal cells, and in some such embodiments comprise mammalian cells, such as human cells.

In one preferred embodiment, the mammalian cells comprise anchorage dependent cells, which can attach and spread onto material surfaces. In one preferred embodiment, the microfluidic network stamping stamp provided according to the invention is placed with its stamping surface in conformal contact with the material surface to be patterned with a plurality of cells, and, after filling one or more fluid flow paths of the microfluidic stamp with one or more suspensions of cells and before removing the stamp from the material surface, the cells are allowed to incubate within the channel structure of the microfluidic stamp for a period of time sufficient to allow the cells to attach and spread onto the material surface. In such an embodiment, the shape or pattern of channels can be specifically designed to have a predetermined architecture or pattern selected to simulate a desired tissue micro-architecture in order to study the relationship between cell shape and/or position and cell function.

In other embodiments, two or more different cell types can be patterned onto a material surface, as described above, and, subsequent to removing the microfluidic stamp, can be allowed to grow upon the surface and spread such that cells of the two or more different cells types spread together and come into contact on the surface after a period of time has elapsed. Such a patterning and incubation method can be useful as part of an in vitro assay, which is able to determine and/or study interactions between different cell types. For example, such method can form part of an in vitro assay able to determine an angiogenic potential of a particular type of tumor cell. In one particular application contemplated, two different cell types comprising capillary endothelial cells and tumor cells are patterned onto a material surface and allowed to grow and spread upon the surface after patterning, as described above, in order to simulate and study angiogenesis during tumor formation. In vivo, tumor cells tend to attract and direct the growth of capillary endothelial cells to form new blood vessels to supply nutrients and oxygen for tumor growth. By forming a defined pattern of capillary endothelial cells and tumor cells utilizing the microfluidic stamps provided according to the invention, it can be possible to enable assays able to study the differential and competitive attraction of capillary endothelial cells to different tumor cell lines. This technique, enabled by the present invention, can lead to the development of a simple, standardized, and quantitative in vitro assay for comparing the angiogenic potential of different tumor cells.

In addition, as discussed above, the present microfluidic network stamps enable two or more different cell types to be patterned onto a material surface in a wide variety of patterns of arbitrary complexity and in a predetermined arrangement, which arrangement can be selected to simulate a distinct micro-architecture defined by the topological relationship between the different cell types patterned on the surface. The ability to pattern and selectively deposit different cell types in well-defined patterned structures, enabled by the present invention, can enable assays designed to study the functional significance of tissue architecture at the resolution of individual cells, and can enable assays designed to study the molecular interactions between different cell types that underlie processes such as embryonic morphogenesis, formation of the blood-brain barrier, and tumor angiogenesis.

The function and advantage of these and other embodiments of the present invention will be more fully understood from the examples below. The following examples are intended to illustrate the benefits of the present invention, but do not exemplify the full scope of the invention.

EXAMPLE 1

Fabrication of a Mold Master by Multi-Level Photolithography

A mold master of photoresist on silicon having two levels of features in positive, high relief (i.e., protruding above the surface of the silicon wafer) was fabricated using the two-level photolithography technique outlined in FIG. 8. Designs for the channel systems for the first and second levels were generated with a CAD computer program (Free-Hand 8.0, MacroMedia, San Francisco, Calif.). High resolution (3386 dpi) transparencies were made by printing with a commercial printer (Linotype, Hercules Computer Technology, Inc., Freemont, Calif.) from the CAD computer files. Two transparencies were produced, the first comprising the photomask for producing features in the first level of the mold master and the second comprising photomask for producing the features in the second level of the mold master.

Negative photoresist (SU8-50, Microlithography Chemical Corp., Newton, Mass.) was spin-coated (at about 5,000 rpm for 20 sec) on a silicon wafer to a depth of about 50 $\mu$m and soft-baked at about 105° C. for about 5 min to drive off solvent from the spin-cast photoresist. The first transparency was then used as a photomask and the photoresist was exposed to UV radiation for about 45 sec (wavelength of spectral lines about: 365 nanometers, 406 nanometers, and 436 nanometers at an intensity of about 10 mW/cm$^2$).

Without developing the uncrosslinked photoresist, a second layer of photoresist was spin-cast to a depth of about 100 $\mu$m on top of the first layer. The second transparency comprising the second photomask was aligned to the exposed features of the photoresist of the first layer using a Karl Suss mask aligner and exposed to the UV radiation for about 1 min. The silicon wafer containing the exposed photoresist layers was then hard-baked for about 5 min. at about 105° C. The second photomask contained the pattern corresponding to the interconnecting channels that would eventually link channels of the first, lower level formed by the features exposed through the first photomask, and channels of the upper levels of the replica molded structure ultimately molded with the mold master. As illustrated in FIG. 8, each of the photomasks also included a pattern for forming alignment tracks surrounding the channel system.

Both layers of photoresist were developed at the same time to remove uncrosslinked photoresist with propylene glycol methyl ether acetate. The resulting bottom master included tall alignment features and channel features comprising two-level topological features in positive relief. The surface of the bottom mold master including the topological features was then silanized by placing the mold master in a vacuum chamber with a few drops of tridecafluoro-1,1,2,2-tetrahydrooctyl-1-trichlorosilane (United Chemical Technologies, Inc., Bristol, Pa.) for about 2 hours. Silanization of the master facilitates the removal of a PDMS replica after molding.

EXAMPLE 2

Figure 12A:
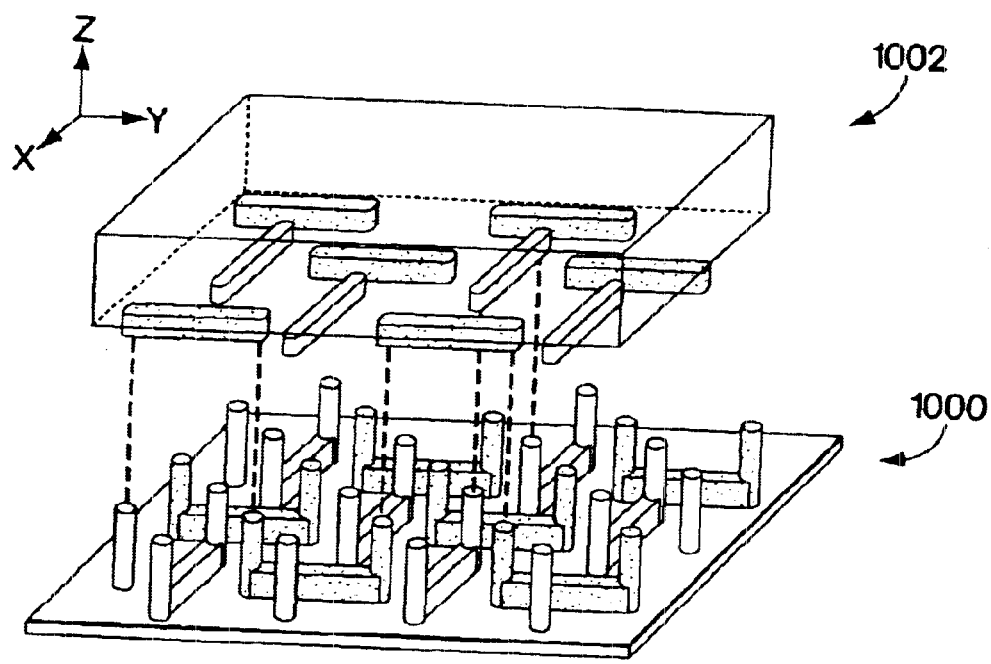
FIG. 12a is a perspective view of a schematic illustration of a lower and an upper mold master for forming a basketweave microfluidic network structure provided by the invention.

Fabrication of a Three-Dimensional Microfluidic Network Including a System of Channels in a "Basketweave" Configuration In the following example, the method outlined in FIGS. 9a and 9b was utilized to produce a microfluidic network structure including a channel pattern therein having a basketweave structure similar to that illustrated in FIG. 1a. First, a bottom master was produced as described above in Example 1 having disposed thereon two-level topological features for forming channels within the molded replica arranged similarly to those shown schematically in FIG. 12a by bottom master 1000. The second step of the process comprised formation of a top master including features for forming channels in the uppermost level of the replica molded membrane. A similar schematic arrangement of features for producing the channels, and the way in which the channels of the upper mold master and lower mold master fit together to mold the overall structure, is also illustrated in FIG. 12a, making specific reference to upper mold master schematic 1002.

The top mold master was made by first fabricating a two-level structure in photoresist on silicon comprising a pre-master by a method similar to that discussed above in Example 1. The pre-master contained features in negative, low-relief (i.e., comprising indentations below the level of the bulk surface) so that replica molding the upper mold master with the pre-master produced features in positive, high-relief on the upper mold master, as shown schematically in FIG. 12a and as shown and discussed earlier in the context of FIG. 9a. The topological features of the pre-master corresponding to the channel system extended to a level below the surface of the photoresist, but did not traverse it completely; these features were all on one level. Alignment tracks (not shown in FIG. 12a) that were shaped and positioned to form alignment tracks in the replica molded top mold master that fit between alignment tracks on the bottom master (not shown in FIG. 12a) during replica molding of the microfluidic membrane with the mold masters were fabricated in deeper, negative relief and went all the way through the photoresist to the silicon wafer. The pre-master was then silanized as described above in Example 1. The pre-master was then covered with PDMS prepolymer (Sylgard 184™ silicone elastomer with about a 1:10 ratio of curing agent to elastomeric silicone polymer) and cured at about 75° C. for about 1 hour. The PDMS replica, comprising a top mold master, was then peeled from the pre-master, trimmed, and oxidized in a plasma cleaner (PDC-23G, Harrick, Ossining, N.Y.) for 1 min, and then was silanized by placing it in a vacuum chamber with a few drops of tridecafluoro-1,1,2,2-tetrahydrooctyl-1-trichlorosilane (United Chemical Technologies, Inc., Bristol, Pa.) for about 8 hours.

The upper mold master was then placed facedown on top of the surface of the bottom mold master including topological features, with a drop of PDMS prepolymer in between. The features of the masers were aligned quickly and without magnification by manually sliding the top master over the prepolymer and bottom master until its tall alignment tracks slipped between the tall alignment tracks of the bottom master. Utilizing PDMS for the top master enabled visual observation of the features of the masters and made alignment straightforward. A microscope was not necessary because the alignment tracks were macroscopic. In addition to facilitating the alignment of the segments of the channel system quickly and without magnification, the alignment tracks also balanced the top master and prevented the registered masters from shifting in position in response to physical disturbances or the application of pressure during molding.

A pressure of about 100 g/mm² (1000 kPa) was then applied to the top master so that prepolymer did not seep between features that were in contact, and the PDMS was heated to about 75° C. and cured in place for about 1 hour. In addition, two flat pieces of PDMS comprising an upper and lower substrate layer were formed by casting the PDMS prepolymer against a flat, silanized silicon wafer and curing, as described above. To transfer the membrane, the membrane and top master were peeled off as a single unit from the bottom master; the surface of the membrane and the flat pieces of PDMS were oxidized in an air plasma for 1 min, as described above; and the oxidized surfaces were then brought together immediately. The oxidized PDMS surface remains reactive for a few minutes after plasma treatment. Reactivity of the surface can be prolonged by covering the surface, if desired, with a hydrophilic liquid such as water, methanol, trifluoroethanol, or mixture thereof. A protected surface will still seal more than 30 min after oxidation.

After contacting the membrane with the bottom PDMS slab, the top master was peeled off, and the top surface of the membrane was sealed to the second oxidized flat slab to enclose the channel system. The entire structure was then trimmed to a convenient size. The resulting structure included a microfluidic network incorporating eight channels in the x-direction and eight in the y-direction, each having a width of about 100 μm and a height of about 70 μm, and each alternating between crossing over and under channels oriented perpendicular to themselves. The entire structure had a total area in the x-y plane of about 30 mm² and contained 64 crossovers.

Figure 12B:
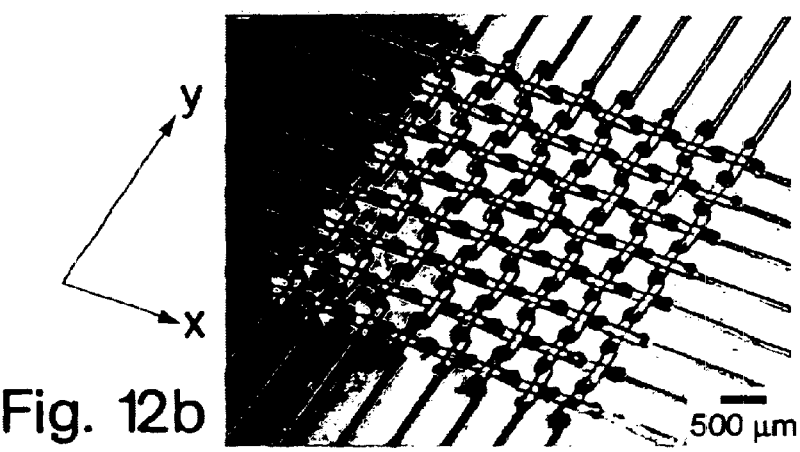
FIGS. 12b–12c provide photocopies of photomicrographs of a microfluidic network characterized by a network of channels arranged in a basketweave configuration in accordance with one embodiment of the present invention.

FIG. 12b is a photocopy of an optical photomicrograph showing an enface phase contrast image of the structure as viewed in the negative z-axis direction. The optical micrograph illustrated in FIG. 12b was taken of the replica molded membrane alone prior to sealing the membrane between the upper and lower PDMS substrate layers. The optical photomicrograph clearly shows the basketweave microfluidic channel structure and the crossover points of the channels, appearing as intersections in photographed the x-y plane.

Figure 12C:
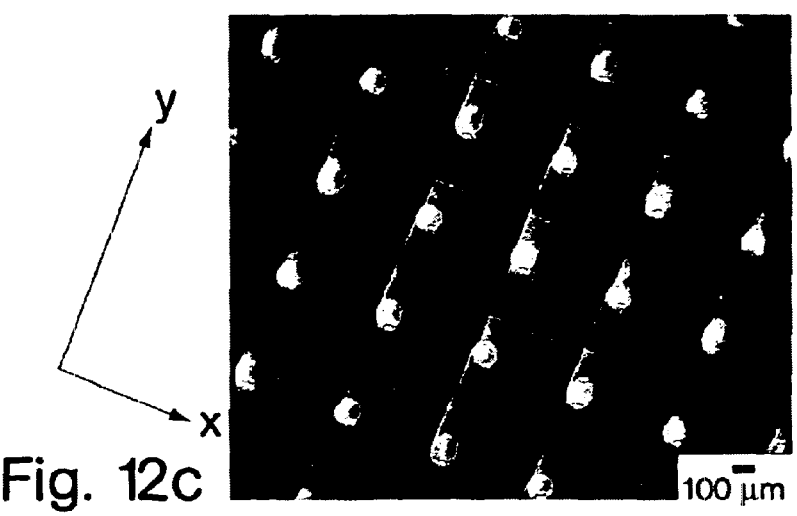

After enclosing the membrane between an upper and lower PDMS support layer as described above, flow paths extending in the y direction were filled with a solution of fluorescein and flow paths extending in the x direction were filled with a solution of Meldola's Blue Dye. FIG. 12c is a photocopy of a photomicrograph of the microfluidic channel system filled as described above, with the observer viewing the system enface in the negative z-axis direction. FIG. 12c shows, without ambiguity, which channels cross over and which cross under each other, and also demonstrates that the channels do not intersect, as would be evidenced by mixed colors at any point.

EXAMPLE 3

Figure 12D:
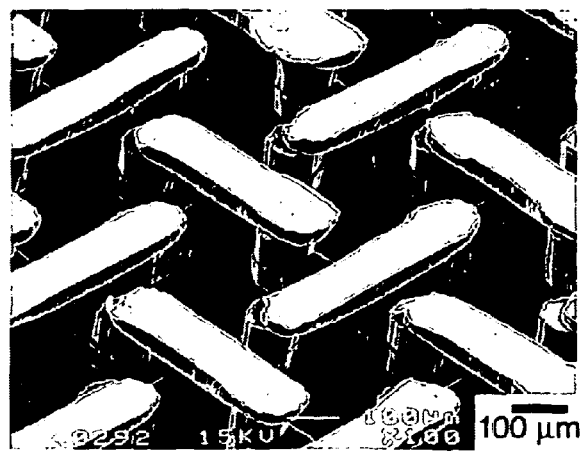
FIG. 12d is a photocopy of an SEM image of a micromolded structure produced according to one embodiment of the invention.

Fabrication of Microstructures by Replica Molding With a Microfluidic Network Structure A microfluidic membrane including a three-level channel system in a basketweave pattern was produced as described in Example 2. The microfluidic membrane was placed upon a flat PDMS slab so that the upper surface of the PDMS slab and the lower surface of the membrane were in conformal contact but were not irreversibly sealed to each other. The upper surface of the membrane was left open to the atmosphere. An epoxy prepolymer (EP-TEK, Epoxy Technology, Billerica, Mass.) was then placed at the channel openings and allowed to fill the channel structure by capillary action. After approximately 1 hour standing at ambient pressure, the epoxy had degassed and filled the channels completely. The filled channels were then exposed to UV light (as described above in Example 1) for about 20 min through the PDMS. The surrounding PDMS microfluidic membrane was then dissolved in tetrabutylammonium fluoride (1.0 M in tetrahydrofuran). FIG. 12d is a photocopy of a scanning electron photomicrograph of the resulting microstructure produced by the cured epoxy polymer.

EXAMPLE 4

Fabrication of a Microfluidic Network Structure Including a Coiled Fluid Flow Path Surrounding a Straight Channel To demonstrate the capability of stacking, registering, and sealing membranes to each other to make structures having more than three levels of channels, a structure was fabricated including a straight channel surrounded by a coiled fluid flow path comprising a series of interconnected channels. The flow path comprising the straight channel was separated from the channels comprising the coiled flow path by a thin, about 65–100 μm, PDMS layer. Examples of microfluidic systems that benefit from such a configuration include heat exchange elements or countercurrent extraction system taking advantage of the diffusion of small molecules across the PDMS layer separating the straight channel and the coiled fluid flow path. Multi-layer fabrication techniques such as the one in the current example also have utility for devices for sorting and binding particles, and for complex channel network systems that have specific size constraints.

The method used for producing the five-level channel system by stacking and aligning two replica molded multi-level membranes was illustrated above in FIG. 10. Referring to FIG. 10, first, bottom master 802 was fabricated as described above in Example 1. Upper mold masters 820 and 830 were fabricated as described in Example 2. Replica molded membranes 800 and 810 were fabricated of cured PDMS prepolymer, also as described above in Example 2. Bottom master 802 was removed from each of the membranes and flat slabs of PDMS were sealed in their place, as described above in Example 2. The top masters were then peeled off and the two membranes were aligned face-to-face on the stages of micromanipulators. This orientation required that the two-level membrane 810 be flipped over. The membranes were brought together and aligned, and were then backed apart by about 3 to about 5 mm without disturbing the previous alignment. The separated membranes were then oxidized in an air plasma, as described above, and then brought into conformal contact.

Figure 13:
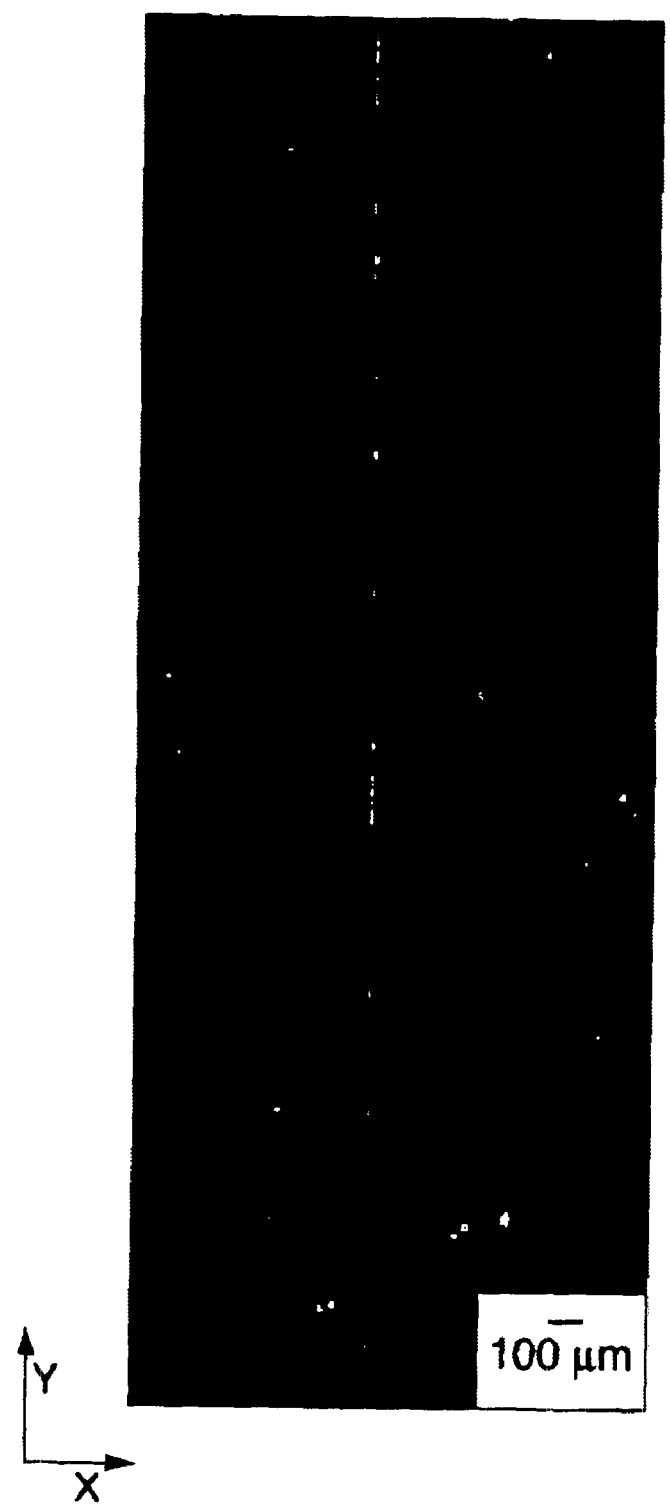
FIG. 13 is a photocopy of a photomicrograph of a microfluidic network comprising a straight channel surrounded by a coiled fluid flow path comprising a series of interconnected channels, according to one embodiment of the invention.

FIG. 13 shows a photocopy of an optical photomicrograph of the resulting channel system as viewed enface along the negative z-axis direction. Prior to the photomicrograph being taken, the two fluid flow paths of the system were filled with a fluorescein solution, as described in Example 2, to aid visualization of the channel system.

EXAMPLE 5

Fabrication of a Microfluidic Stamp and Etching of a Si/SiO$_2$ Surface and Visualization of the Etched Surface Using Optical Interference Colors For the present example, a three-dimensional microfluidic stamp was produced according to the method outlined in FIG. 7. Referring to FIG. 7, two-level lower mold master was prepared as previously described in Example 1 and one-level mold master 500 was prepared also as described in Example 1, except utilizing only a single layer of photoresist and a single photomask to produce only one level of topological features. The top PDMS slab 510 was fabricated by placing mold master 500 in a container with surface 502 facing up, covering the mold master with PDMS prepolymer, curing the PDMS prepolymer, as described above in Example 2, and removing and trimming the molded replica to form PDMS slab 510.

PDMS membrane 550 was fabricated by sandwiching a drop of PDMS prepolymer between master 520 and a PTFE sheet. Pressure of between about 10 and about 50 kpa was applied tending to force the PTFE sheet and mold master 520 together. The PDMS prepolymer was then cured, as described in Example 2. After curing, PTEE sheet 540 was peeled away, leaving the membrane remaining attached to mold master 520 by van der Waals interactions.

To align and seal the PDMS slab to the PDMS membrane a micromanipulator stage was used. The slab and membrane were mounted on the micromanipulator stage so that surface 514 was facing surface 556. The surfaces were brought into close proximity and aligned. After alignment, the surfaces were backed away from each other by a few millimeters using the micromanipulator. The entire alignment stage was then placed in a plasma cleaner (Anatech, Model SP100 Plasma System, Springfield, Va.) and oxidized for about 40 sec in an oxygen plasma. The power level of the plasma cleaner was about 60 watts and the oxygen pressure was about 0.2 Torr. Sealing of the two layers was accomplished by removing the assembly from the plasma cleaner and immediately bringing the two aligned and oxidized PDMS surfaces into contact.

Figure 14B:
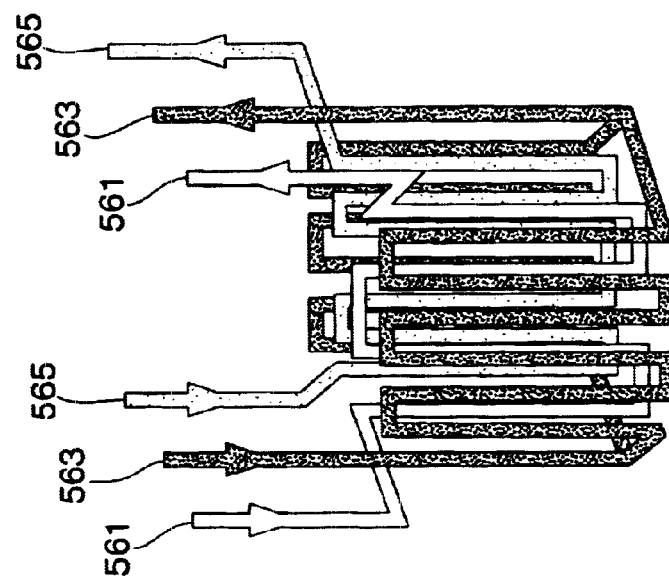
Figure 14A:
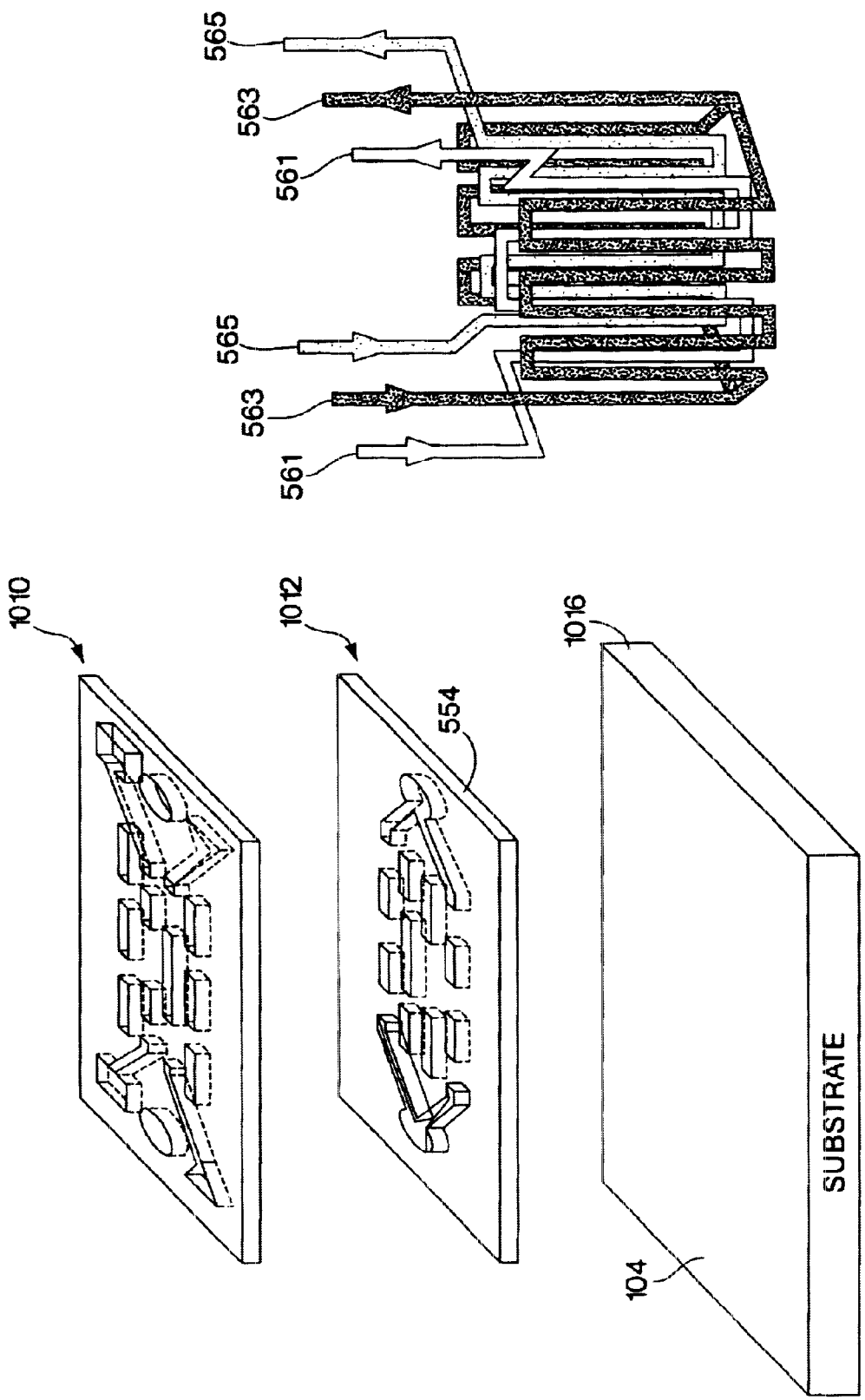
FIG. 14a is a schematic illustration of a microfluidic stamping process according to one embodiment of the invention.

FIG. 14a illustrates schematically the channel system disposed in the upper level 1010 of the microfluidic stamp and the lower level 1012 of the microfluidic stamp, which lower level having a lower surface 554 comprising the stamping surface. Surface 554 was brought into conformal contact with material surface 1014 of substrate 1016. FIG. 14b is a schematic diagram illustrating the layout and interconnectivity of the three-level channel system within microfluidic stamp 560 and the configuration of each of the three non-fluidically interconnected fluid flow paths 561, 563, and 565.

Figure 14C:
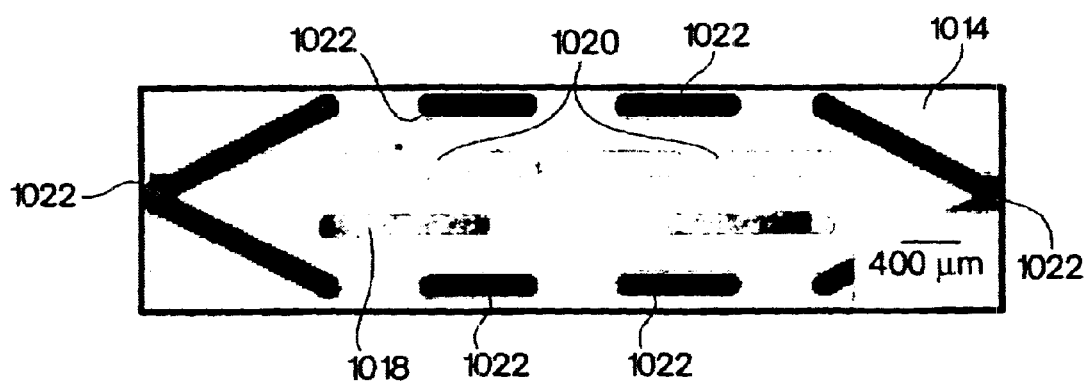

To create the etched pattern on surface 1014 shown in FIG. 14c, surface 554 of the microfluidic stamp was brought into conformal contact with surface 1014 (comprising a Si/SiO$_2$ surface) and gentle pressure was applied to the stamp. Three aqueous solutions containing three different concentrations of hydrofluoric acid (10%, 5%, and 3% hydrofluoric acid, buffered at about pH 5 with a 6:1 ratio of NH$_4$F/HF) were allowed to flow (~1 cm/sec), with each solution confined to one of the non-fluidically interconnected flow paths in the structure. Each of the channels in the structure had a cross-sectional area, measured in a plane perpendicular to the channel's longitudinal axis, of about 500 $\mu$m$^2$. Where the hydrofluoric acid solutions came into contact with the surface, they etched away the SiO$_2$. The rate of etching of SiO$_2$ for 10% hydrofluoric acid is about 20 nm/min. The lower concentrations etched at a rate proportionally less than the most concentrated solution. The hydrofluoric acid solutions were flowed through the channels for a period of about 26 min before removing the stamp from the surface and visualizing the pattern.

The optical interference color of an SiO$_2$ layer is very sensitive to the thickness of the layer; a difference of about 30 nm, for example, can change the color from, for example, light green to blue. Thus, patterns etched to different depths within surface 1014 appear as different colors. Referring to FIG. 14c, patterned features 1018, corresponding to fluid flow path 561, which contained the 10% hydrofluoric acid solution, were etched into surface 1014 to a depth of about 520 nm and appear green. Etched patterned features 1020, corresponding to fluid flow path 565, which contained the 5% hydrofluoric acid solution, were etched into surface 1014 to a depth of about 390 nm and appear yellow. Patterned features 1022, corresponding to fluid flow path 563, which contained the 3% hydrofluoric acid solution, were etched into surface 1014 to a depth of about 70 nm and appear brown.

EXAMPLE 6

Figure 15A:
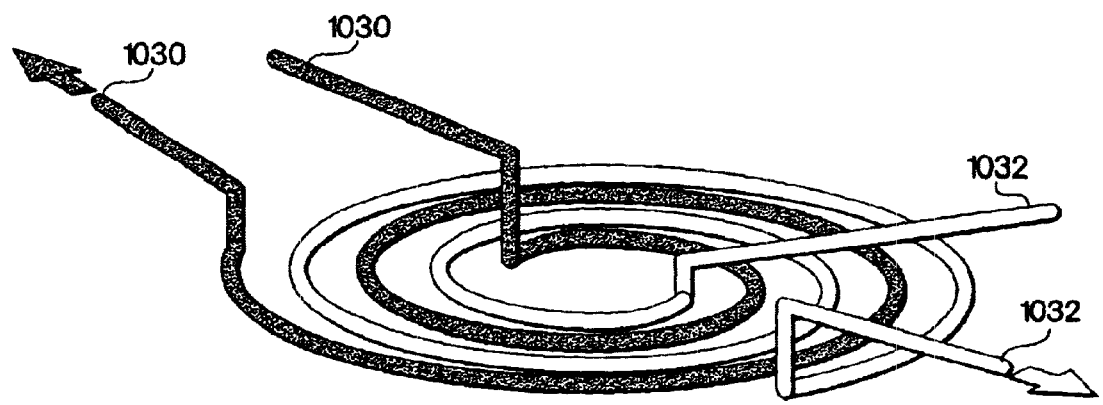
FIG. 15a is a schematic illustration of the layout of fluid flow paths in one embodiment of a microfluidic stamp provided according to the invention.

Patterned Deposition of Proteins Onto a Surface Using a Three-Dimensional Microfluidic Stamp A microfluidic stamp having a stamping surface with spirally arranged channels therein was produced by a method similar to that described above in Example 5. The microfluidic stamp had a microfluidic channel system shown schematically in FIG. 15a. The stamp included two non-fluidically interconnected fluid flow paths 1030 and 1032. The channels of fluid flow paths 1030 and 1032 are disposed in the stamping surface of the microfluidic stamp in a nested spiral arrangement as illustrated in FIG. 15a.

The stamping surface of the microfluidic stamp was placed in conformal contact with a polystyrene surface of a petri dish. Spiral flow paths 1030 was then filled with a FITC-labeled bovine serum albumin (BSA) solution having a labeled BSA concentration of 1 mg/ml in phosphate buffer (pH 7.4). Fluid flow path 1032 was filled with a FITC-labeled fibrinogen solution containing 0.1 mg/ml labeled fibrinogen in phosphate buffer (pH 7.4). The proteins were allowed to absorb onto the polystyrene surface for about 45 min. The channels were then flushed thoroughly with phosphate buffer; the stamp was peeled off; and the surfaces were observed en face with fluorescence microscopy.

Figure 15B:
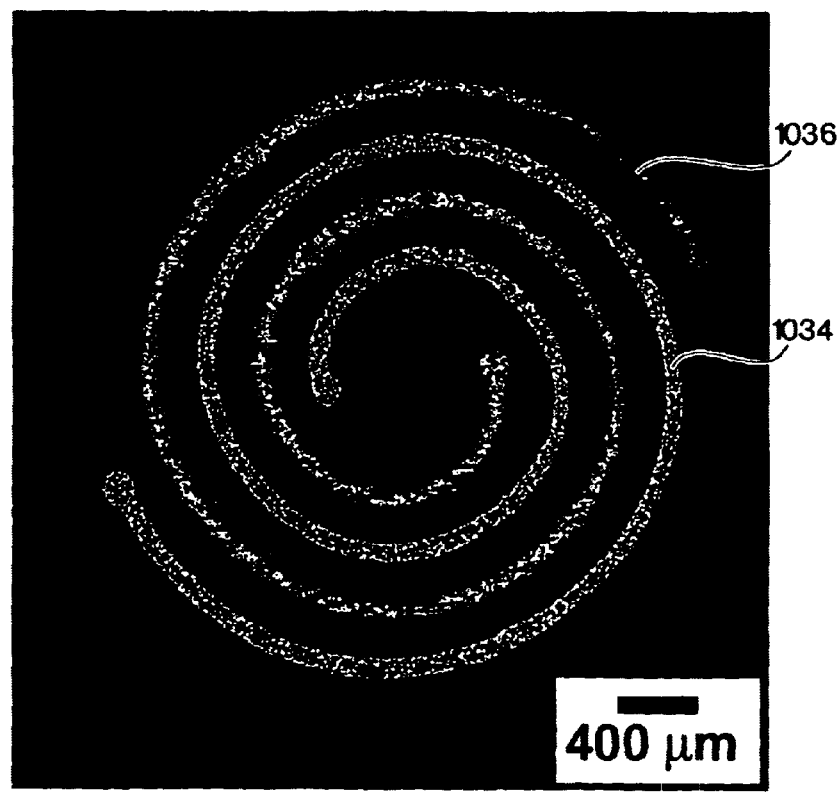

FIG. 15b is a photocopy of a photomicrograph taken of the surface of the petri dish as viewed utilizing fluorescence microscopy. Spiral pattern 1034 comprises a layer of deposited labeled BSA and spiral pattern 1036 comprises a layer of deposited labeled fibrinogen. Spiral pattern 1034 is brighter and more fluorescent because the concentration of BSA used was about 10 times higher than the concentration of fluorescently labeled fibrinogen.

EXAMPLE 7

Patterned Deposition of Cells Onto Surfaces Using Two Different Microfluidic Systems Cell cultures: Bovine adrenal capillary endothelial cells (BCEs) were cultured as described in J. Folkman, C. C. Haudenschild, B. R. Zetter, *Proc. Natl. Acad. Sci. USA*, Vol. 76, pp. 5217–5221, 1982. In brief, BCEs were grown in low glucose DMEM cell culture medium supplemented with 10% calf serum and 2 ng/ml basic fibroblast growth factor (bFGF), and kept in a 10% $CO_2$ atmosphere. Human bladder cancer cells (ECVs) from the ECV304 cell line were cultured in DMEM supplemented with 10% fetal bovine serum (FBS) and kept in a 5% $CO_2$ atmosphere. Cells from both cell types were labeled fluorescently before harvest at 37° C. in the $CO_2$ incubator. BCEs were incubated with 1,1'-dioctadecyl-3,3,3',3'-tetramethylindocarbocyanine (DiI)-conjugated acetylated low-density lipoprotein at 4 $\mu$g/ml, which is actively taken up by BCEs and stored in endosomal granula. ECV304 cells were incubated with 5 $\mu$M 5-chloromethylfluorescein diacetate (CMFDA), which reacts with intracellular glutathione. Before patterning, cells were washed with PBS, dissociated from the culture plates to which they were attached during culture with typsin/EDTA, washed with DMEM, and resuspended in the respective culture media at a density of about $10^6$ cells/ml. For culturing patterned cells (both BCEs and ECVs) after removal of the PDMS stamp, DMEM supplemented with 5% calf serum, 5% FBS, and 2 ng/ml bFGF was used, and the cells were kept in a 10% $CO_2$ atmosphere.

Figure 16A:
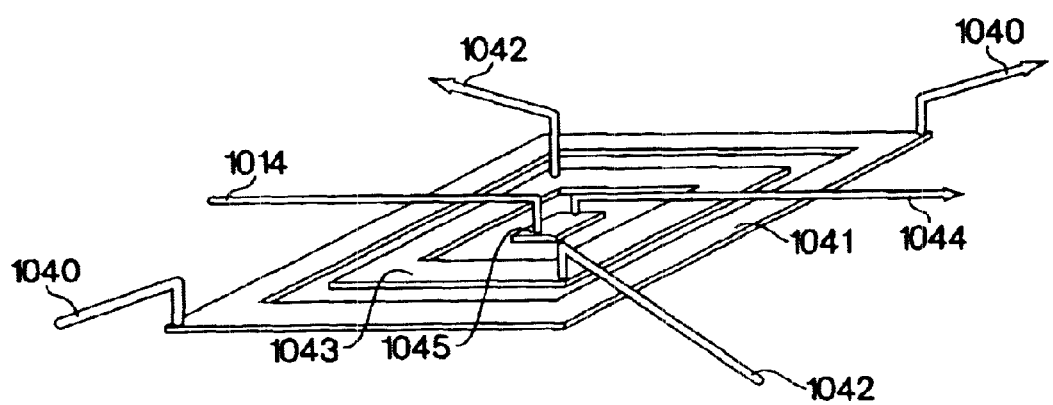
FIG. 16a is a schematic illustration of the layout of fluid flow paths in one embodiment of a microfluidic stamp provided according to the invention.

Pattering: To form the first pattern of deposited cells, a microfluidic stamp having the channel network structure illustrated schematically in FIG. 16a was fabricated by a method similar to that described above in Example 5. A stamping surface of the microfluidic stamp included disposed therein channels comprising a concentric square pattern. The microfluidic stamp included three non-fluidically interconnected fluid flow paths 1040, 1042, and 1044, fluid flow path 1040 in fluid communication with outermost concentric square pattern 1041, fluid flow path 1042 in fluid communication with the intermediate concentric square pattern 1043, and fluid flow path 1044 in fluid communication with the innermost concentric square pattern 1045.

Before use, the PDMS microfluidic stamp was autoclaved at about 121° C. for about 20 min, and the walls of the channels were coated with BSA by filling the channels with a 0 mg/ml BSA solution in pH 7.4 phosphate buffer for about 1 hour before removing the solution and flushing with BSA-free phosphate buffer. The stamping surface was then brought into conformal contact with the surface of a polystyrene tissue culture dish. Suspensions of cells (at a concentration of about $5 \times 10^6$ cells/ml) were introduced into the three fluid flow paths and were allowed to sediment and attach to the surface of the tissue culture dish. The cells used were BCEs and an ECV cell line (ECV-304). Before being deposited, the BCEs were labeled with DiI-conjugated acetylated low-density lipoprotein, which was actively taken up by the BCEs and stored in their endosomal granula, and the ECVs with CMFDA, which reacted with their intracellular glutathione. The BCE cell solutions were introduced into fluid flow paths 1040 and 1044, and the ECV cell solution was introduced into fluid flow path 1042. After introducing the cell suspension into the fluid flow paths of the microfluidic stamp, the cells were cultured for about 24 hours with the microfluidic stamp in place on the tissue culture dish surface, so as to form a confluent layer of cells on the surface of the tissue culture dish. After culture, the microfluidic stamp was removed from the surface, and the surface, having cells attached thereto, was immersed in tissue culture media, as previously described.

Figure 16B:
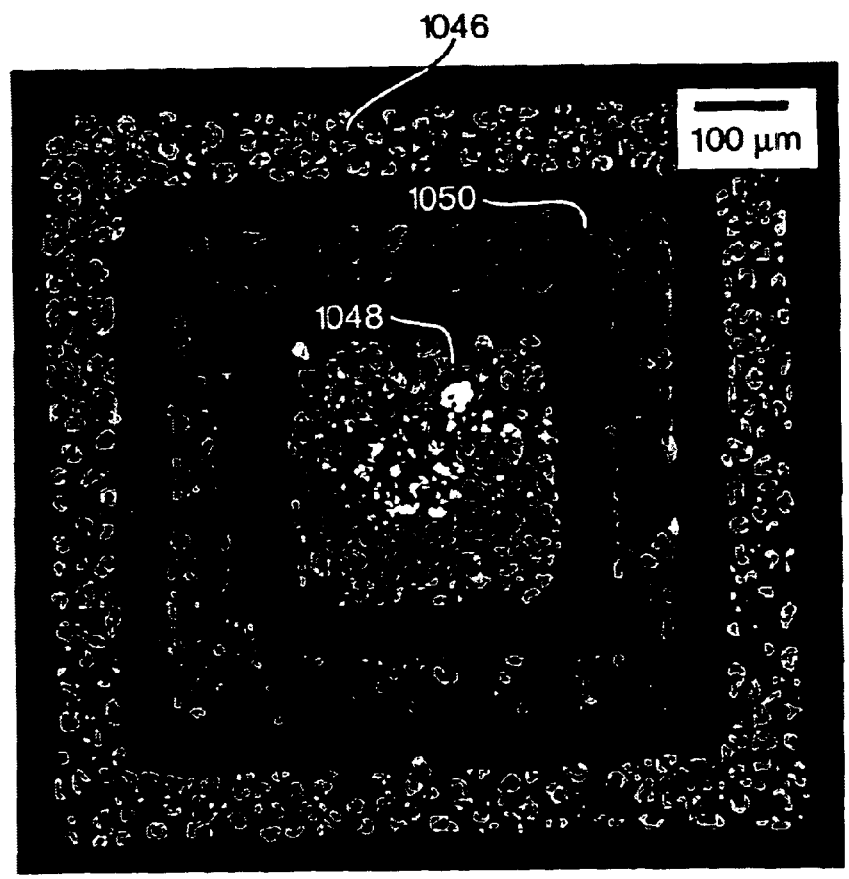
Figure 16C:
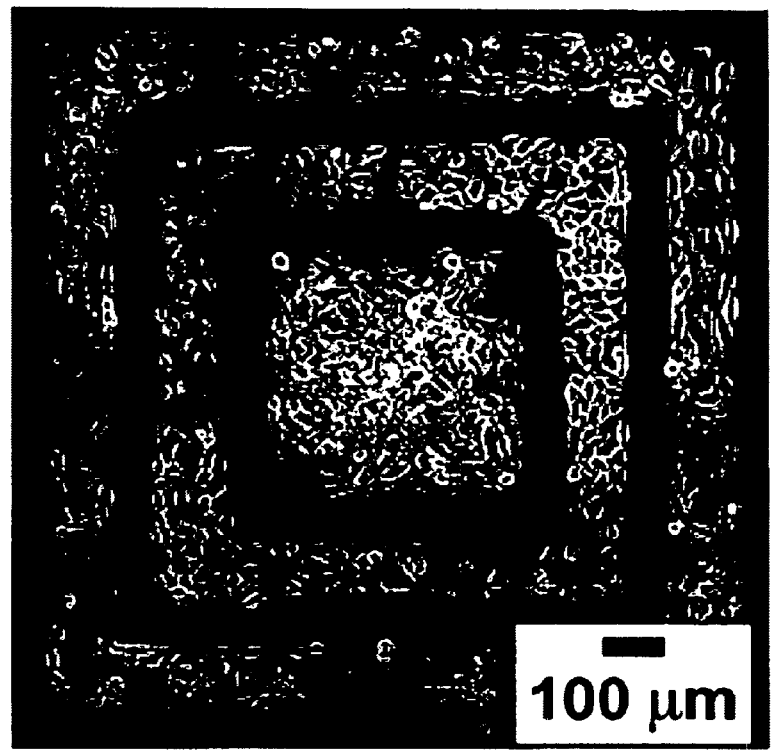
Figure 16D:
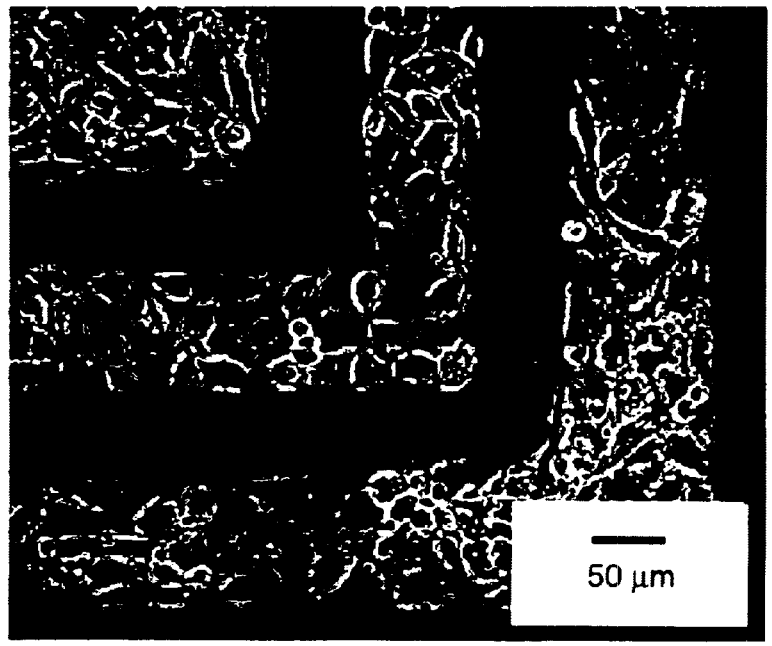

FIG. 16b is a photocopy of a photomicrograph of surface of the petri dish as observed by fluorescence microscopy. The deposited BCE cells are attached to the surface in the outermost concentric square pattern 1046 and the innermost concentric square pattern 1048. Such cells, when viewed with the fluorescence microscope appear red in color. The ECV cells are deposited on the surface in concentric square pattern 1050 and fluoresce green when viewed with the fluorescence microscope. FIGS. 16c and 16d are photocopies of photomicrographs of the patterned surface as viewed with phase-contrast microscopy, illustrating the morphology and arrangement of the cells within each of the patterns on the surface.

Figure 17A:
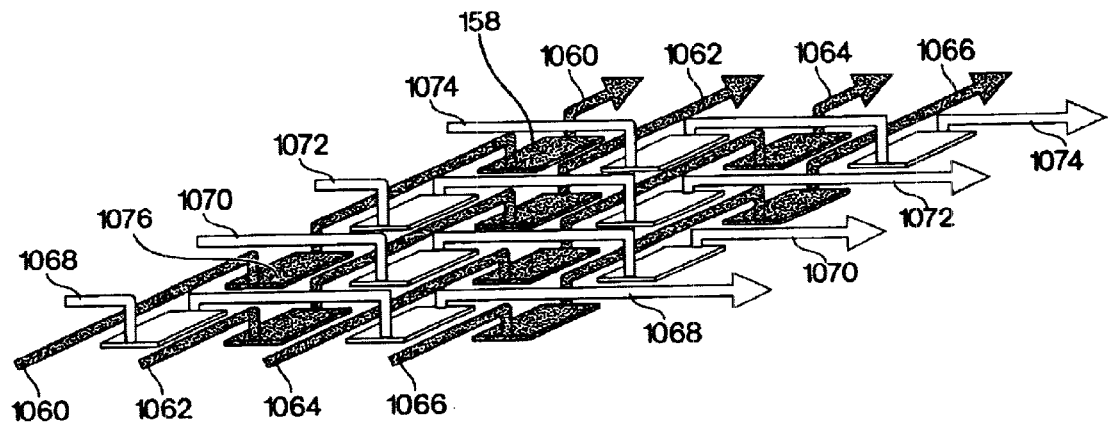
FIG. 17a is a schematic illustration of the layout of fluid flow paths in one embodiment of a microfluidic stamp provided according to the invention.
Figure 17B:
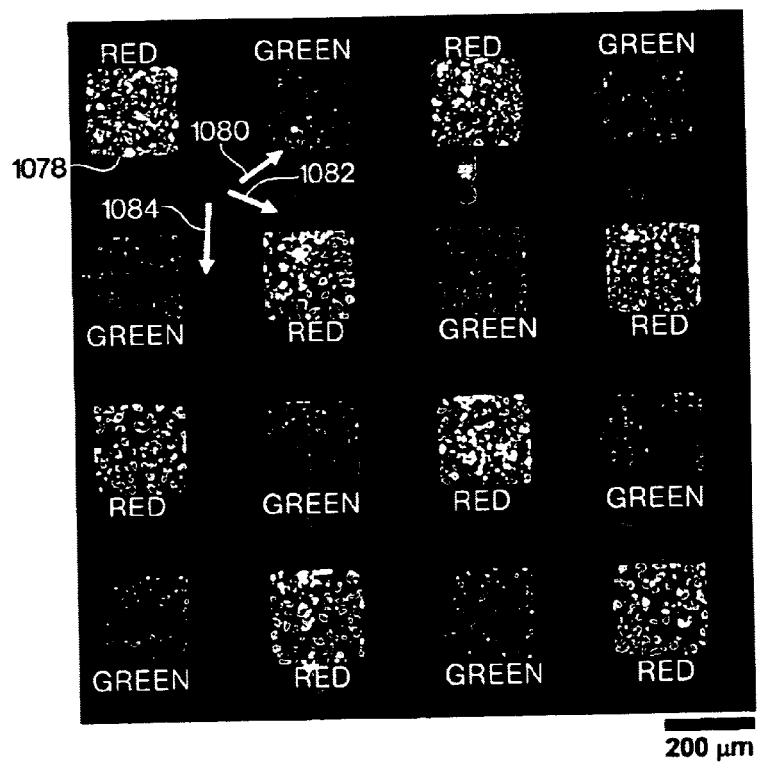

FIGS. 17a and 17b show the results of a similar cell patterning experiment wherein two types of cells were deposited in a chessboard-like pattern. The chessboard-like pattern was designed as a demonstration of the potential of the microfluidic stamping system and method of the invention to deposit multiple cell types in an array format appropriate for a biosensor or drug screening applications. In such an array, the responding cells could be identified by their spatial location. A microfluidic stamp having fluid flow paths shown schematically in FIG. 17a was prepared by a method similar to that described above in Example 5. The microfluidic stamp included eight non-fluidically interconnected independent flow paths 1060, 1062, 1064, 1066, 1068, 1070, 1072, and 1074. Each of the flow paths is in fluid communication with two square channels disposed in the stamping surface of the microfluidic stamp. For example, fluid flow path 1060 is in fluid communication with square channels 1076 and 1078 disposed within the stamping surface of the microfluidic stamp.

A chessboard pattern of cells is shown in FIG. 17b, which is a photocopy of a fluorescence photomicrograph. The patterned surface was produced using the same procedures used for patterning the concentric square pattern of FIGS. 16b–16d. The two cell types used, BCEs and ECVs, were fluorescently labeled, as described above, before being deposited onto the surface of a tissue culture plate. Solutions of fluorescently labeled ECV cells were used to fill fluid flow paths 1060, 1062, 1064, and 1066, and solutions of fluorescently labeled BCE cells were used to fill fluid flow paths 1068, 1070, 1072, and 1074. The cells were cultured with the stamp in place on the surface for 42 hours until a confluent layer of cells were formed on the surface of the tissue culture plate. The fluorescence photomicrograph (a photocopy of which is shown in FIG. 17b) was taken with the PDMS microfluidic stamp still in place on the tissue culture plate surface in order to show the overlaying weaving channel structures. The color of each of the confluent layers of cells as viewed by fluorescence microscopy, is indicated on the figure above each square pattern feature. The blurred red spots 1080, 1082 and the blurred green spot 1084 comprise cells located in the channel structure of the top level of the microfluidic stamp above the focal plane of the microscope.

Figure 17C:
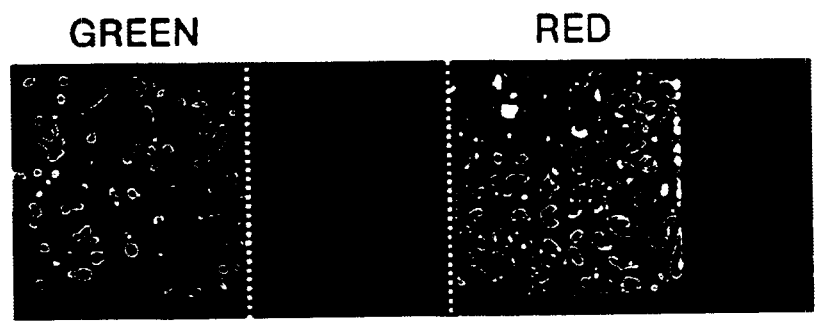
Figure 17D:
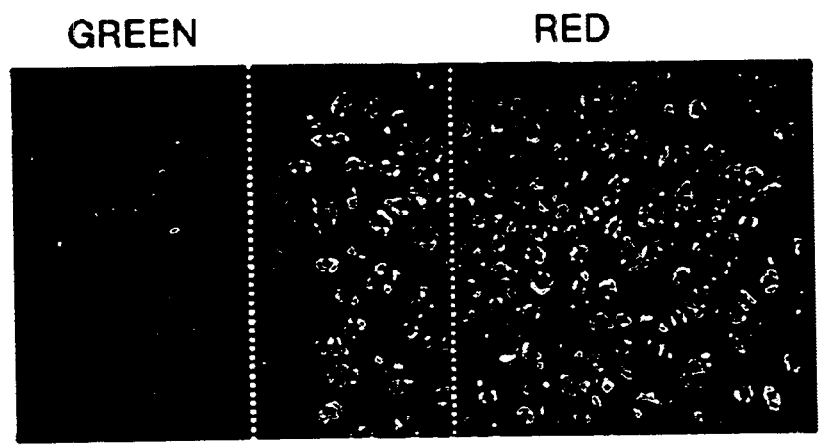
Figure 17E:
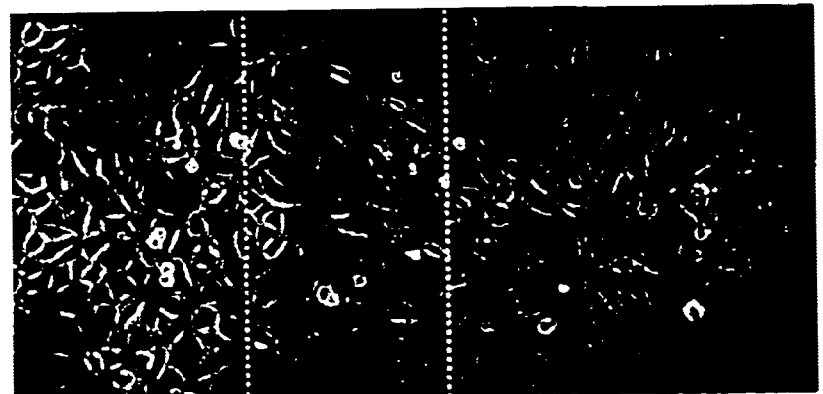

After removing the microfluidic stamp from the surface of the tissue culture plate, the surface was placed in tissue culture medium, as previously described, and cultured, as previously described, to allow the two cell types to grow and spread together. FIG. 17c shows a portion of the image of FIG. 17b illustrating a patterned feature comprising green deposited ECV cells and red deposited BCE cells. The two regions containing cells are separated by an intermediate region of the tissue culture plate surface (set off by dotted white lines), which is free of cells. FIG. 17d shows a photocopy of a fluorescence photomicrograph taken of the identical region of the tissue culture plate surface taken 20 hours after removal of the stamp and subsequent culture of the plate. FIGS. 17c and 17d are registered, and the dotted intermediate region of FIG. 17d comprises the region in FIG. 17c that was initially cell free. As can be seen, after 20 hours of culture subsequent to removal of the microfluidic stamp, both cell types have divided, grown, and spread together within the region that was initially cell free. FIG. 17e shows the same region as shown FIG. 17d, also after 20 hours of culture subsequent to removing the stamp, except as viewed with phase contrast light microscopy.

Those skilled in the art would readily appreciate that all parameters listed herein are meant to be examples and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed:

1. A method of patterning a material surface comprising: providing a stamp having a structure including at least one flow path comprising a series of interconnected channels within the structure, the series of interconnected channels including at least one first channel disposed within an interior region of the structure, at least one second channel disposed within a stamping surface of the structure defining a first pattern therein, and at least one connecting channel fluidically interconnecting the first channel and the second channel;

contacting the stamping surface with a portion of the material surface; while maintaining the stamping surface in contact with the portion of the material surface, at least partially filling the flow path with a fluid so that at least a portion of the fluid contacts the material surface.

2. The method of patterning a material surface as in claim 1, further comprising:

removing the stamping surface to provide a pattern on the material surface according to the first pattern and formed by contact of the material surface with the fluid.

3. The method of patterning a material surface as in claim 1, wherein the stamp is fabricated from an elastomeric material.

4. The method of patterning a material surface as in claim 3, wherein the elastomeric material comprises a silicone polymer.

5. The method of patterning a material surface as in claim 4, wherein the silicone polymer comprises poly (dimethylsiloxane).

6. The method of patterning a material surface as in claim 2, wherein the stamp has a structure including at least two non-fluidically interconnected flow paths therein including a first fluid flow path defining the first pattern of channels disposed within the stamping surface of the structure, and a second fluid flow path defining a second pattern of channels disposed within the stamping surface of the structure, with each of the first and second patterns of channels disposed within the stamping surface being non-continuous, and with channels defining the first pattern being non-intersecting with channels defining the second pattern.

7. The method of patterning a material surface as in claim 6, wherein during the while maintaining step, the first flow path is at least partially filled with a first fluid so that at least a portion of the first fluid contacts the material surface, and the second fluid flow path is at least partially filled with a second fluid so that at least a portion of the second fluid contacts the material surface.

8. The method of patterning a material surface as in claim 7, wherein after the removing step, an overall pattern that results on the material surface corresponds to both the first pattern, which is formed by contact of the material surface and the first fluid, and to the second pattern, which is formed by contact of the material surface and the second fluid.

9. The method of patterning a material surface as in claim 2, wherein the fluid comprises a liquid solution, mixture, or suspension of at least one protein, and wherein the pattern provided on the material surface is comprised of a deposited layer of the protein.

10. The method of patterning a material surface as in claim 9, wherein the at least one protein comprises a protein tending to inhibit cell adhesion to the material surface.

11. The method of patterning a material surface as in claim 10, wherein the at least one protein comprises bovine serum albumin.

12. The method of patterning a material surface as in claim 9, wherein the at least one protein comprises a protein tending to promote cell adhesion to the material surface.

13. The method of patterning a material surface as in claim 12, wherein the at least one protein comprises a protein selected from the group consisting of: fibrinogen; collagen; laminin; integrins; antibodies; antigens; cell receptor proteins; and cell receptor antagonists.

14. The method of patterning a material surface as in claim 2, wherein the fluid comprises a liquid containing an inorganic material, and wherein the pattern provided on the material surface is comprised of a deposited layer of the inorganic material.

15. The method of patterning a material surface as in claim 1, wherein the fluid is chemically reactive with the material surface.

16. The method of patterning a material surface as in claim 15, wherein the fluid etches at least a portion of the material surface.

17. The method of patterning a material surface as in claim 2, wherein the fluid comprises a liquid suspension of a plurality of cells of at least one cell type, and wherein the pattern provided on the material surface is comprised of a deposited layer of cells.

18. The method of patterning a material surface as in claim 17, wherein the plurality of cells comprises a plurality of mammalian cells.

19. The method of patterning a material surface as in claim 18, wherein the mammalian cells are anchorage dependent cells.

20. The method of patterning a material surface as in claim 19, wherein the mammalian cells comprise cells selected from the group consisting of capillary endothelial cells and tumor cells.

21. The method of patterning a material surface as in claim 17, further comprising be fore the removing step, the steps of: incubating the plurality of cells within the at least one flow path; and allowing the cells to attach and spread onto the material surface.

22. The method of patterning a material surface as in claim 21, wherein the method forms part of an in vitro assay able to determine interactions between different cell types.

23. The method of patterning a material surface as in claim 22, wherein the method forms part of an in vitro assay able to determine an angiogenic potential of tumor cells.

24. The method of patterning a material surface as in claim 21, wherein a predetermined pattern of cells is formed on the material surface, the predetermined pattern selected to simulate a desired tissue micro-architecture.

25. A method of patterning a material surface comprising: providing a stamp having a structure including at least two non-fluidically interconnected flow paths therein including a first fluid flow path defining a first pattern of channels disposed within a stamping surface of the structure and a second fluid flow path defining a second pattern of channels disposed within the stamping surface of the structure, with each of the first and second patterns of channels being non-continuous, and with channels defining the first pattern being non-intersecting with channels defining the-second pattern;

contacting the stamping surface with a portion of the material surface; while maintaining the stamping surface in contact with the portion of the material surface, at least partially filling the first flow path with a first fluid so that at least a portion of the first fluid contacts the material surface and at least partially filling the second flow path with a second fluid so that at least a portion of the second fluid contacts the material surface; and removing the stamping surface to provide a pattern on the material surface according to the first pattern, which is formed by contact of the material surface with the first fluid, and according to the second pattern, which is formed by contact of the material surface with the second fluid.

* * * * *

UNITED STATES PATENT AND TRADEMARK OFFICE
CERTIFICATE OF CORRECTION

| | | |
|---|---|---|
| PATENT NO. | : 6,686,184 B1 | Page 1 of 1 |
| APPLICATION NO. | : 09/578562 | |
| DATED | : February 3, 2004 | |
| INVENTOR(S) | : Janelle R. Anderson et al. | |

It is certified that error appears in the above-identified patent and that said Letters Patent is hereby corrected as shown below:

In the Specification

At Column 1, Lines 7-11, please change the paragraph:
"This invention was made with government support: Grant Nos. GM51559; GM30367 from the National Institutes of Health, and Grant No. ECS9729405 from the National Science Foundation. The government has certain rights to the invention."

To:
--This invention was made with government support under GM030367, and GM051559 awarded by the National Institutes of Health, and 9729405 awarded by the National Science Foundation. The government has certain rights in the invention.--

Signed and Sealed this
Twenty-seventh Day of August, 2024

Katherine Kelly Vidal
*Director of the United States Patent and Trademark Office*